US008394777B2

(12) United States Patent
Sitbon et al.

(10) Patent No.: US 8,394,777 B2
(45) Date of Patent: Mar. 12, 2013

(54) TREATING IMMUNODEFICIENCIES BY INTRATHYMIC INJECTION OF NUCLEOTIDE SEQUENCES

(75) Inventors: Naomi Sitbon, Montpellier (FR); David Klatzmann, Paris (FR); Cedric Mongellaz, Montpellier (FR); Oumeya Adjali, Montpellier (FR); Chantal Jacquet, Lunel (FR); Marcos Steinberg, San Diego, CA (US); Gilles Marodon, Paris (FR)

(73) Assignees: Centre National de la Recherche Scientifique, Paris (FR); Universite Pierre et Marie Curie, Paris (FR); Universite Montpellier II, Montpellier (FR)

( * ) Notice: Subject to any disclaimer, the term of this patent is extended or adjusted under 35 U.S.C. 154(b) by 708 days.

(21) Appl. No.: 11/597,892

(22) PCT Filed: Jun. 3, 2005

(86) PCT No.: PCT/EP2005/005992
§ 371 (c)(1),
(2), (4) Date: Feb. 25, 2008

(87) PCT Pub. No.: WO2005/117989
PCT Pub. Date: Dec. 15, 2005

(65) Prior Publication Data
US 2008/0206210 A1 Aug. 28, 2008

Related U.S. Application Data

(60) Provisional application No. 60/576,613, filed on Jun. 4, 2004.

(51) Int. Cl.
*A61K 48/00* (2006.01)
(52) U.S. Cl. .................................... 514/44 R; 424/93.2
(58) Field of Classification Search .................. None
See application file for complete search history.

(56) References Cited

FOREIGN PATENT DOCUMENTS
WO WO03105874 * 12/2003

OTHER PUBLICATIONS

DeMatteo et al. Long-Lasting Adenovirus Transgene Experssion in Mice through Neonatal Intrathymic Tolerance Induction without the Use of Immunosuppression. Jouranl of Virology, Jul. 1997, vol. 71, pp. 5330-5335.*
Wong et al. Retroviral Gene Transfer of a Donor Class I MHC GEne to Recipient Bone Marrow CElls INduces Tolerance to Alloantigens In Vivo. Transplantation Proceedings, 1997, vol. 29, p. 1130.*
VandenDriessche. Long-Term Expression of Human Coagulation Factor VIII and Correction of Hemophilia A after In Vivo Retroviral Gene Transfer in Factor VIII-deficient Mice. Proc. Natl. Acad. Sci., 1999, vol. 96, pp. 10373-10384.*
Stegmann et al. Synthetic HLA-A2 Derived Peptides are Recognized and Presented in Renal Graft Recipients. Human Immunology, 2000, vol. 61, pp. 1363-1369.*
Steinberg et al. Retrovirus-mediated transduction of primary ZAP-70-deficient human T cells results in the selective growth advantage of gene-corrected cells: implications for gene therapy. Gene Therapy, 2000, vol. 7, pp. 1392-1400.*
Taylor et al. Reconstitution of T Cell Receptor Signaling in ZAP-70-deficient Cells by Retroviral Transduction of the ZAP- 70 Gene J. Experimental Med., 1996, vol. 184, pp. 2031-2036.*
Travers et al. Protocols for high efficiency, stage-specific retroviral transduction of murine fetal thymocytes and thymic epithelial cells. J. Immun. Methods, 2001, vol. 253, pp. 209-222.*
Seppen et al. Apical Gene Transfer into Quiescent Human and Canine Polarized Intestinal Epithelial Cells by Lentivirus Vectors J. Virol., 2000, vol. 74, pp. 7642-7645.*
Tiberghien et al. Administration of herpes simplex—thymidine kinase—expressing donor T cells with a T-cell-depleted allogeneic marrow graft Blood, 2001, vol. 97, pp. 63-72.*
Marodon Gilles et al: "Specific transgene expression in human and mouse CD4+ cells using lentiviral vectors with regulatory sequences from the CD4 gene." Blood, vol. 101, No. 9, May 2003, pp. 3416-3423, XP002342653 ISSN: 006-4971, p. 3421-p. 3422; figure 1.
Zhao-Emonet J C et al: "T cell-specific expression from Mo-MLV retroviral vectors containing a CD4 mini-promoter/enhancer." The Journal of Gene Medicine. Nov.-Dec. 2000, vol. 2, No. 6, Nov. 2000, pp. 416-425, XP008051622 ISSN: 1099-498X, figure 1, the whole document.
Delenda Christophe: "Lentiviral vectors: optimization of packaging, transduction and gene expression." The Journal of Gene Medicine. Feb. 2004, vol. 6 Suppl 1, pp. S125-S138, XP008051607 ISSN: 1099-498X, figure 3.
Rooke Ronald et al: "Targeted complementation of MHC class II deficiency by intrathymic delivery of recombinant adenoviruses" Immunity, vol. 7, No. 1, 1997, pp. 123-134, XP002342778, ISSN: 1074-7613 the whole document.
Adjali Oumeya et al: "In vivo correction of ZAP-70 immunodeficiency by intrathymic gene transfer." The Journal of Clinical Investigation. Aug. 2005, vol. 115, No. 8, pp. 2287-2295, XP002342655 ISSN: 0021-9738, figure 1-4, the whole document.
Seggewiss Ruth et al: "A new direction for gene therapy: intrathymic T cell-specific lentiviral gene transfer." The Journal of Clinical Investigation. Aug. 2005, vol. 115, No. 8, pp. 2064-2067, ISSN: 0021-9738, the whole document.
Marodon Gilles and Klatzmann David: "In situ transduction of stromal cells and thymocytes upon intrathymic injection of lentiviral vectors." BMC Immunology 'Electronic Resource!. Aug. 19, 2004, vol. 5, No. 1, p. 18, XP008051658, ISSN: 1471-2172, figure 1-3, the whole document.

*Primary Examiner* — Deborah Crouch
(74) *Attorney, Agent, or Firm* — Young & Thompson

(57) ABSTRACT

The invention relates to the use of viral vectors able to stably integrate into the genome of thymic stromal cells, or of intrathymic lymphocytes or lymphocytes precursors, for the manufacture of a medicine intended for intrathymic administration in the frame of the prevention or treatment of genetic immunodeficiencies, acquired immunodeficiencies, or for the induction of immune tolerance of the organism to self or non-self gene products, cells or tissues, or for the prevention or treatment of autoimmune diseases.

7 Claims, 14 Drawing Sheets

SEQUENCE LISTING

<160> NUMBER OF SEQ ID NOS: 7

<210> SEQ ID NO 1
<211> LENGTH: 4695
<212> TYPE: DNA
<213> ORGANISM: Artificial Sequence
<220> FEATURE:
<223> OTHER INFORMATION: Description of Artificial Sequence: Synthetic
      lentiviral vector containing a mammalian insulin
      coding sequence

<400> SEQUENCE: 1

```
ttaatgtagt cttatgcaat actcttgtag tcttgcaaca tggtaacgat gagttagcaa      60
catgccttac aaggagagaa aaagcaccgt gcatgccgat tggtggaagt aaggtggtac     120
gatcgtgcct tattaggaag gcaacagacg ggtctgacat ggattggacg aaccactgaa     180
ttgccgcatt gcagagatat tgtatttaag tgcctagctc gatacaataa acgggtctct     240
ctggttagac cagatctgag cctgggagct ctctggctaa ctagggaacc cactgcttaa     300
gcctcaataa agcttgcctt gagtgcttca agtagtgtgt gcccgtctgt tgtgtgactc     360
tggtaactag agatccctca gacccttta gtcagtgtgg aaaatctcta gcagtggcgc      420
ccgaacaggg acctgaaagc gaaagggaaa ccagagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcggggagaa     600
attagatcgc gatgggaaaa aattcggtta aggccagggg gaaagaaaaa atataaatta     660
aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggccgctgat cttcagacct ggaggaggag atatgaggga     960
caattggaga agtgaattat ataaatataa agtagtaaaa attgaaccat taggagtagc    1020
acccaccaag gcaaagagaa gagtggtgca gagagaaaaa agagcagtgg gaataggagc    1080
tttgttcctt gggttcttgg gagcagcagg aagcactatg ggcgcagcct caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620
agtttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcggtt    1800
aacttttaaa agaaaagggg ggattggggg gtacagtgca ggggaaagaa tagtagacat    1860
aatagcaaca gacatacaaa ctaaagaatt acaaaaacaa attacaaaaa ttcaaaattt    1920
```

```
tatcgatcac gagactagcc tcgagaagct tgatatcgaa ttcccacggg gttggggttg    1980
cgccttttcc aaggcagccc tgggtttgcg cagggacgcg gctgctctgg gcgtggttcc    2040
gggaaacgca gcggcgccga ccctgggtct cgcacattct tcacgtccgt tcgcagcgtc    2100
acccggatct tcgccgctac ccttgtgggc ccccggcga cgcttcctgc tccgccccta    2160
agtcgggaag gttccttgcg gttcgcggcg tgccggacgt gacaaacgga agccgcacgt    2220
ctcactagta ccctcgcaga cggacagcgc cagggagcaa tggcagcgcg ccgaccgcga    2280
tgggctgtgg ccaatagcgg ctgctcagcg gggcgcgccg agagcagcgg ccgggaaggg    2340
gcggtgcggg aggcggggtg tggggcggta gtgtgggccc tgttcctgcc cgcgcggtgt    2400
tccgcattct gcaagcctcc ggagcgcacg tcggcagtcg gctccctcgt tgaccgaatc    2460
accgacctct ctccccaggg ggatcctaga caacatggcc ctgtggatgc gcttcctgcc    2520
cctgctggcc ctgctcttcc tctgggagtc ccaccccacc caggcttttg tcaagcagca    2580
cctttgtggt tcccacctgg tggaggctct ctacctggtg tgtggggagc gtggcttctt    2640
ctacacaccc atgtcccgcc gtgaagtgga ggacccacaa gtggcacaac tggagctggg    2700
tggaggcccg ggagcaggtg accttcagac cttggcactg gaggtggccc agcagaagcg    2760
tggcattgta gatcagtgct gcaccagcat ctgctccctc taccagctgg agaactactg    2820
caactagaca ctagtccggc gggtttctga catccggcgg gtttctgaca tccggcgggt    2880
ttctgacatc cggcgggttt ctgacatccg gcgggtgaat tcttctgaca tccggcgggt    2940
ttctgacatc cggcgggttt ctgacatccg gcgggttct gacatccggc gggtttctga    3000
catccggcgg gtgactcaca accccagaaa cagacatcca tggtgagcaa gggcgaggag    3060
ctgttcaccg gggtggtgcc catcctggtc gagctggacg gcgacgtaaa cggccacaag    3120
ttcagcgtgt ccggcgaggg cgagggcgat gccacctacg gcaagctgac cctgaagttc    3180
atctgcacca ccggcaagct gcccgtgccc tggcccaccc tcgtgaccac cctgacctac    3240
ggcgtgcagt gcttcagccg ctaccccgac cacatgaagc agcacgactt cttcaagtcc    3300
gccatgcccg aaggctacgt ccaggagcgc accatcttct tcaaggacga cggcaactac    3360
aagacccgcg ccgaggtgaa gttcgagggc gacaccctgg tgaaccgcat cgagctgaag    3420
ggcatcgact tcaaggagga cggcaacatc ctggggcaca gctggagta caactacaac    3480
agccacaacg tctatatcat ggccgacaag cagaagaacg gcatcaaggt gaacttcaag    3540
atccgccaca acatcgagga cggcagcgtg cagctcgccg accactacca gcagaacacc    3600
cccatcggcg acggccccgt gctgctgccc gacaaccact acctgagcac ccagtccgcc    3660
ctgagcaaag accccaacga gaagcgcgat cacatggtcc tgctggagtt cgtgaccgcc    3720
gccgggatca ctctcggcat ggacgagctg tacaagtaaa gcgtcttcga agtcggatcc    3780
gtcgacaatc aacctctgga ttacaaaatt tgtgaaagat tgactggtat tcttaactat    3840
gttgctcctt ttacgctatg tggatacgct gctttaatgc ctttgtatca tgctattgct    3900
tcccgtatgg ctttcatttt ctcctccttg tataaatcct ggttgctgtc tctttatgag    3960
gagttgtggc ccgttgtcag gcaacgtggc gtggtgtgca ctgtgtttgc tgacgcaacc    4020
cccactggtt gggcattgc caccacctgt cagctccttt ccgggacttt cgctttcccc    4080
ctccctattg ccacggcgga actcatcgcc gcctgccttg cccgctgctg dacagggct    4140
cggctgttgg gcactgacaa ttccgtggtg ttgtcgggga agctgacgtc ctttccatgg    4200
ctgctcgcct gtgttgccac ctggattctg cgcgggacgt ccttctgcta cgtcccttcg    4260
gccctcaatc cagcggacct tccttcccgc ggcctgctgc cggctctgcg gcctcttccg    4320
```

-continued

```
cgtcttcgcc ttcgccctca gacgagtcgg atctcccttt gggccgcctc cccgcctgga    4380
attcgagctc ggtaccttta agaccaatga cttacaaggc agctgtagat cttagccact    4440
ttttaaaaga aaagggggga ctggaagggc taattcactc ccaacgaaga caagatctgc    4500
tttttgcttg tactgggtct ctctggttag accagatctg agcctgggag ctctctggct    4560
aactagggaa cccactgctt aagcctcaat aaagcttgcc ttgagtgctt caagtagtgt    4620
gtgcccgtct gttgtgtgac tctggtaact agagatccct cagacccttt tagtcagtgt    4680
ggaaaatctc tagca    4695
```

<210> SEQ ID NO 2
<211> LENGTH: 6660
<212> TYPE: DNA
<213> ORGANISM: Artificial Sequence
<220> FEATURE:
<223> OTHER INFORMATION: Description of Artificial Sequence: Synthetic lentiviral vector containing a mammalian ZAP-70 coding sequence

<400> SEQUENCE: 2

```
ttaatgtagt cttatgcaat actcttgtag tcttgcaaca tggtaacgat gagttagcaa      60
catgccttac aaggagagaa aaagcaccgt gcatgccgat tggtggaagt aaggtggtac     120
gatcgtgcct tattaggaag gcaacagacg ggtctgacat ggattggacg aaccactgaa     180
ttgccgcatt gcagagatat tgtatttaag tgcctagctc gatacaataa acgggtctct     240
ctggttagac cagatctgag cctgggagct ctctggctaa ctagggaacc cactgcttaa     300
gcctcaataa agcttgcctt gagtgcttca agtagtgtgt gcccgtctgt tgtgtgactc     360
tggtaactag agatccctca gaccctttta gtcagtgtgg aaaatctcta gcagtggcgc     420
ccgaacaggg acctgaaagc gaaagggaaa ccagagctct ctcgacgcag gactcggctt     480
gctgaagcgc gcacggcaag aggcgagggg cggcgactgg tgagtacgcc aaaaattttg     540
actagcggag gctagaagga gagagatggg tgcgagagcg tcagtattaa gcggggggaga     600 attagatcgc gatgggaaaa aattcggtta aggccagggg gaagaaaaa atataaatta     660 aaacatatag tatgggcaag cagggagcta gaacgattcg cagttaatcc tggcctgtta     720
gaaacatcag aaggctgtag acaaatactg ggacagctac aaccatccct tcagacagga     780
tcagaagaac ttagatcatt atataataca gtagcaaccc tctattgtgt gcatcaaagg     840
atagagataa aagacaccaa ggaagcttta gacaagatag aggaagagca aaacaaaagt     900
aagaccaccg cacagcaagc ggccgctgat cttcagacct ggaggaggag atatgaggga     960
caattggaga agtgaattat ataaatataa gtagtaaaa attgaaccat taggagtagc    1020
acccaccaag gcaaagagaa gagtggtgca gagagaaaaa agagcagtgg gaataggagc    1080
tttgttcctt gggttcttgg gagcagcagg aagcactatg ggcgcagcct caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620
```

```
agtttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcggtt    1800
aactttaaa agaaaagggg ggattggggg gtacagtgca ggggaaagaa tagtagacat    1860
aatagcaaca gacatacaaa ctaaagaatt acaaaaacaa attacaaaaa ttcaaaattt    1920
tatcgataag ctgcatgctg ttggggttca aatttgagcc ccagctgtta gccctctgca    1980
aagaaaaaaa aaaaaaaaaa agaacaaagg gcctagattt cccttctgag ccccacccta    2040
agatgaagcc tcttctttca agggagtggg gttggggtgg aggcggatcc tgtcagcttt    2100
gctctctctg tggctggcag tttctccaaa gggtaacagg tgtcagctgg ctgagcctag    2160
gctgaaccct gagacatgct acctctgtct tctcatggct ggaggcagcc tttgtaagtc    2220
acagaaagta gctgaggggc tctgaaaaaa agacagccag ggtggaggta gattggtgca    2280
tgcagcttct gcagccccgc gtgctagaga tttaagcctg attctgctta acttttccc    2340
ttgactttgg cattttcact ttgacatgtt ccctgagagc ctgggggtg gggaaccagc    2400
tccagctggt gacgtttggg gccggccag gcctagggtg tggaggagcc ttgccatcgg    2460
gcttcctgtc tctcttcatt taagcacgac tctgcaggtc gagatctaag taagcttgat    2520
catgccagac cccgcggcgc acctgccctt cttctacggc agcatctcgc gtgccgaggc    2580
cgaggagcac ctgaagctgg cgggcatggc ggacgggctc ttcctgctgc gccagtgcct    2640
gcgctcgctg ggcggctatg tgctgtcgct cgtgcacgat gtgcgcttcc accactttcc    2700
catcgagcgc cagctcaacg gcacctacgc cattgccggc ggcaaagcgc actgtggacc    2760
ggcagagctc tgcgagttct actcgcgcga ccccgacggg ctgccctgca acctgcgcaa    2820
gccgtgcaac cggccgtcgg gcctcgagcc gcagccgggg gtcttcgact gcctgcgaga    2880
cgccatggtg cgtgactacg tgcgccagac gtggaagctg gagggcgagg ccctggagca    2940
ggccatcatc agccaggccc cgcaggtgga gaagctcatt gctacgacgg cccacgagcg    3000
gatgccctgg taccacagca gcctgacgcg tgaggaggcc gagcgcaaac tttactctgg    3060
ggcgcagacc gacggcaagt tcctgctgag gccgcggaag gagcagggca catacgccct    3120
gtccctcatc tatgggaaga cggtgtacca ctacctcatc agccaagaca aggcgggcaa    3180
gtactgcatt cccgagggca ccaagtttga cacgctctgg cagctggtgg agtatctgaa    3240
gctgaaggcg gacgggctca tctactgcct gaaggaggcc tgccccaaca gcagtgccag    3300
caacgcctca ggggctgctg ctcccacact cccagcccac ccatccacgt tgactcatcc    3360
tcagagacga atcgacaccc tcaactcaga tggatacacc cctgagccag cacgcataac    3420
gtccccagac aaaccgcggc cgatgcccat ggacacgagc gtgtatgaga gcccctacag    3480
cgacccagag gagctcaagg acaagaagct cttcctgaag cgcgataacc tcctcatagc    3540
tgacattgaa cttggctgcg gcaactttgg ctcagtgcgc cagggcgtgt accgcatgcg    3600
caagaagcag atcgacgtgg ccatcaaggt gctgaagcag ggcacggaga aggcagacac    3660
ggaagagatg atgcgcgagg cgcagatcat gcaccagctg acaacccct acatcgtgcg    3720
gctcattggc gtctgccagg ccgaggccct catgctggtc atggagatgg ctggggcgg    3780
gccgctgcac aagttcctgg tcggcaagag ggaggagatc cctgtgagca atgtggccga    3840
gctgctgcac caggtgtcca tggggatgaa gtacctggag gagaagaact tgtgcaccg    3900
tgacctggcg gcccgcaacg tcctgctggt taaccgcac tacgccaaga tcagcgactt    3960
tggcctctcc aaagcactgg gtgccgacga cagctactac actgcccgct cagcagggaa    4020
```

```
gtggccgctc aagtggtacg cacccgaatg catcaacttc cgcaagttct ccagccgcag    4080
cgatgtctgg agctatgggg tcaccatgtg ggaggccttg tcctacggcc agaagcccta    4140
caagaagatg aaagggccgg aggtcatggc cttcatcgag cagggcaagc ggatggagtg    4200
cccaccagag tgtccacccg aactgtacgc actcatgagt gactgctgga tctacaagtg    4260
ggaggatcgc cccgacttcc tgaccgtgga gcagcgcatg cgagcctgtt actacagcct    4320
ggccagcaag gtggaagggc ccccaggcag cacacagaag gctgaggctg cctgtgcctg    4380
atacgtaaat tccgcccctc tccctccccc cccctaacg ttactggccg aagccgcttg     4440
gaataaggcc ggtgtgcgtt tgtctatatg ttattttcca ccatattgcc gtcttttggc    4500
aatgtgaggg cccggaaacc tggccctgtc ttcttgacga gcattcctag gggtctttcc    4560
cctctcgcca aaggaatgca aggtctgttg aatgtcgtga aggaagcagt tcctctggaa    4620
gcttcttgaa gacaaacaac gtctgtagcg accctttgca ggcagcggaa ccccccacct    4680
ggcgacaggt gcctctgcgg ccaaaagcca cgtgtataag atacacctgc aaaggcggca    4740 caacccagt gccacgttgt gagttggata ttgtggaaa gagtcaaatg gctctcctca       4800
agcgtattca acaaggggct gaaggatgcc cagaaggtac cccattgtat gggatctgat    4860
ctggggcctc ggtgcacatg ctttacatgt gtttagtcga ggttaaaaaa cgtctaggcc    4920
ccccgaacca cggggacgtg gttttccttt gaaaaacacg atgataatat ggccacaacc    4980
atggtgagca agggcgagga gctgttcacc ggggtggtgc ccatcctggt cgagctggac    5040
ggcgacgtga acggccacaa gttcagcgtg tccggcgagg gcgagggcga tgccacctac    5100
ggcaagctga cccctgaagtt catctgcacc accggcaagc tgcccgtgcc ctggcccacc    5160
ctcgtgacca cctgacctta cggcgtgcag tgcttcagcc gctaccccga ccacatgaag    5220
cagcacgact tcttcaagtc cgccatgccc gaaggctacg tccaggagcg caccatcttc    5280
ttcaaggacg acggcaacta caagacccgc gccgaggtga agttcgaggg cgacaccctg    5340
gtgaaccgca tcgagctgaa gggcatcgac ttcaaggagg acggcaacat cctggggcac    5400
aagctggagt acaactacaa cagccacaac gtctatatca tggccgacaa gcagaagaac    5460
ggcatcaagg tgaacttcaa gatccgccac aacatcgagg acggcagcgt gcagctcgcc    5520
gaccactacc agcagaacac ccccatcggc gacggccccg tgctgctgcc cgacaaccac    5580
tacctgagca cccagtccgc cctgagcaaa gaccccaacg agaagcgcga tcacatggtc    5640
ctgctggagt tcgtgaccgc cgccgggatc actcacggca tggacgagct gtacaagtaa    5700
agcggccgcc agcacagtgg tcgacggtac cgcgggcccg gtcgagcgac aatcaacctc    5760
tggattacaa aatttgtgaa agattgactg gtattcttaa ctatgttgct ccttttacgc    5820
tatgtggata cgctgcttta atgcctttgt atcatgctat tgcttcccgt atggctttca    5880
ttttctcctc cttgtataaa tcctggttgc tgtctcttta tgaggagttg tggcccgttg    5940
tcaggcaacg tggcgtggtg tgcactgtgt ttgctgacgc aacccccact ggttgggca    6000 ttgccaccac ctgtcagctc ctttccggga ctttcgcttt cccctccct attgccacgg    6060 cggaactcat cgccgcctgc cttgcccgct gctggacagg ggctcggctg ttgggcactg    6120
acaattccgt ggtgttgtcg gggaagctga cgtccttcc atggctgctc gcctgtgttg    6180
ccacctggat tctgcgcggg acgtccttct gctacgtccc ttcggccctc aatccagcgg    6240
accttccttc ccgcggcctg ctgcggctc tgcggcctct tccgcgtctt cgccttcgcc    6300
ctcagacgag tcggatctcc ctttgggccg cctccccgcc tggaattcga gctcggtacc    6360
tttaagacca atgacttaca aggcagctgt agatcttagc cactttttaa aagaaaaggg    6420
```

```
gggactggaa gggctaattc actcccaacg aagacaagat ctgcttttg cttgtactgg     6480 gtctctctgg ttagaccaga tctgagcctg ggagctctct ggctaactag ggaacccact     6540
gcttaagcct caataaagct tgccttgagt gcttcaagta gtgtgtgccc gtctgttgtg     6600
tgactctggt aactagagat ccctcagacc cttttagtca gtgtggaaaa tctctagcag     6660

<210> SEQ ID NO 3
<211> LENGTH: 559
<212> TYPE: DNA
<213> ORGANISM: Artificial Sequence
<220> FEATURE:
<223> OTHER INFORMATION: Description of Artificial Sequence: Synthetic
      minimal proximal CD4 promoter and murine enhancer

<400> SEQUENCE: 3
tgttggggtt caaatttgag ccccagctgt tagccctctg caaagaaaaa aaaaaaaaa      60 aaagaacaaa gggcctagat ttcccttctg agccccaccc taagatgaag cctcttcttt    120
caagggagtg gggttggggt ggaggcggat cctgtcagct ttgctctctc tgtggctggc    180
agtttctcca aagggtaaca ggtgtcagct ggctgagcct aggctgaacc ctgagacatg    240
ctacctctgt cttctcatgg ctggaggcag cctttgtaag tcacagaaag tagctgaggg    300
gctctggaaa aaagacagcc agggtggagg tagattggtg catgcagctt ctgcagcccc    360
gcgtgctaga gatttaagcc tgattctgct aacttttc ccttgacttt ggcatttca     420 ctttgacatg ttccctgaga gcctgggggg tggggaacca gctccagctg gtgacgtttg    480
gggccggccc aggcctaggg tgtggaggag ccttgccatc gggcttcctg tctctcttca    540
tttaagcacg actctgcag                                                559

<210> SEQ ID NO 4
<211> LENGTH: 4220
<212> TYPE: DNA
<213> ORGANISM: Artificial Sequence
<220> FEATURE:
<223> OTHER INFORMATION: Description of Artificial Sequence: Synthetic
      T-cell specific lentiviral vector

<400> SEQUENCE: 4
agcttaatgt agtcttatgc aatactcttg tagtcttgca acatggtaac gatgagttag      60
caacatgcct tacaaggaga gaaaaagcac cgtgcatgcc gattggtgga agtaaggtgg    120
tacgatcgtg ccttattagg aaggcaacag acgggtctga catggattgg acgaaccact    180
gaattgccgc attgcagaga tattgtattt aagtgcctag ctcgatacaa taaacgggtc    240
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagaccctt ttagtcagtg tggaaaatct ctagcagtgg    420
cgcccgaaca gggacctgaa agcgaaaggg aaaccagagc tctctcgacg caggactcgg    480
cttgctgaag cgcgcacggc aagaggcgag gggcggcgac tggtgagtac gccaaaaatt    540
ttgactagcg gaggctagaa ggagagagat gggtgcgaga gcgtcagtat taagcggggg    600
agaattagat cgcgatggga aaaaattcgg ttaaggccag ggggaagaa aaatataaa     660 ttaaaacata tagtatgggc aagcaggag ctagaacgat tcgcagttaa tcctggcctg    720
ttagaaacat cagaaggctg tagacaaata ctgggacagc tacaaccatc ccttcagaca    780
ggatcagaag aacttagatc attatataat acagtagcaa ccctctattg tgtgcatcaa    840
aggatagaga taaaagacac caaggaagct ttagacaaga tagaggaaga gcaaaacaaa    900
```

```
agtaagacca ccgcacagca agcggccgct gatcttcaga cctggaggag gagatatgag    960
ggacaattgg agaagtgaat tatataaata taaagtagta aaaattgaac cattaggagt   1020
agcacccacc aaggcaaaga gaagagtggt gcagagagaa aaaagagcag tgggaatagg   1080
agctttgttc cttgggttct tgggagcagc aggaagcact atgggcgcag cctcaatgac   1140
gctgacggta caggccagac aattattgtc tggtatagtg cagcagcaga acaatttgct   1200
gagggctatt gaggcgcaac agcatctgtt gcaactcaca gtctgggca tcaagcagct    1260
ccaggcaaga atcctggctg tggaaagata cctaaaggat caacagctcc tggggatttg   1320
gggttgctct ggaaaactca tttgcaccac tgctgtgcct tggaatgcta gttggagtaa   1380
taaatctctg aacagattt ggaatcacac gacctggatg gagtgggaca gagaaattaa    1440
caattacaca agcttaatac actccttaat tgaagaatcg caaaaccagc aagaaaagaa   1500
tgaacaagaa ttattggaat tagataaatg ggcaagtttg tggaattggt ttaacataac   1560
aaattggctg tggtatataa aattattcat aatgatagta ggaggcttgg taggtttaag   1620
aatagttttt gctgtacttt ctatagtgaa tagagttagg cagggatatt caccattatc   1680
gtttcagacc cacctcccaa ccccgagggg acccgacagg cccgaaggaa tagaagaaga   1740
aggtggagag agagacagag acagatccat tcgattagtg aacggatctc gacggtatcg   1800
gttaactttt aaaagaaaag gggggattgg ggggtacagt gcaggggaaa gaatagtaga   1860
cataatagca acagacatac aaactaaaga attacaaaaa caaattacaa aaattcaaaa   1920
ttttatcgat aagctgcatg ctgttggggt tcaaatttga gccccagctg ttagccctct   1980
gcaaagaaaa aaaaaaaaa aaagaacaa agggcctaga tttcccttct gagccccacc    2040
ctaagatgaa gcctcttctt tcaagggagt ggggttgggg tggaggcgga tcctgtcagc   2100
tttgctctct ctgtggctgg cagtttctcc aaagggtaac aggtgtcagc tggctgagcc   2160
taggctgaac cctgagacat gctacctctg tcttctcatg gctggaggca gccttttgtaa   2220
gtcacagaaa gtagctgagg ggctctggaa aaaagacagc cagggtggag gtagattggt   2280
gcatgcagct tctgcagccc cgcgtgctag agatttaagc ctgattctgc ttaacttttt   2340
cccttgactt tggcattttc actttgacat gttccctgag agcctggggg gtggggaacc   2400
agctccagct ggtgacgttt ggggccggcc caggcctagg gtgtggagga gccttgccat   2460
cgggcttcct gtctctcttc atttaagcac gactctgcag gtcgagatct aagtaagctt   2520
gatatcgaat tctgcagtcg acggtaccgc gggcccggga tccaccggtc gccaccatgg   2580
tgagcaaggg cgaggagctg ttcaccgggg tggtgcccat cctggtcgag ctggacggcg   2640
acgtaaacgg ccacaagttc agcgtgtccg gcgagggcga gggcgatgcc acctacggca   2700
agctgaccct gaagttcatc tgcaccaccg gcaagctgcc cgtgccctgg cccaccctcg   2760
tgaccaccct gacctacggc gtgcagtgct tcagccgcta ccccgaccac atgaagcagc   2820
acgacttctt caagtccgcc atgcccgaag gctacgtcca ggagcgcacc atcttcttca   2880
aggacgacgg caactacaag acccgcgccg aggtgaagtt cgagggcgac accctggtga   2940
accgcatcga gctgaagggc atcgacttca aggaggacgg caacatcctg ggcacaagc    3000
tggagtacaa ctacaacagc cacaacgtct atatcatggc cgacaagcag aagaacggca   3060
tcaaggtgaa cttcaagatc cgccacaaca tcgaggacgg cagcgtgcag ctcgccgacc   3120
actaccagca gaacacccc atcggcgacg gccccgtgct gctgcccgac aaccactacc    3180
tgagcaccca gtccgccctg agcaaagacc ccaacgagaa gcgcgatcac atggtcctgc   3240
tggagttcgt gaccgccgcc gggatcactc tcggcatgga cgagctgtac aagtaaaggc   3300
```

```
ggcctcgagc gacaatcaac ctctggatta caaaatttgt gaaagattga ctggtattct   3360
taactatgtt gctccttta cgctatgtgg atacgctgct ttaatgcctt tgtatcatgc    3420
tattgcttcc cgtatggctt tcattttctc ctccttgtat aaatcctggt tgctgtctct   3480
ttatgaggag ttgtggcccg ttgtcaggca acgtggcgtg gtgtgcactg tgtttgctga   3540
cgcaaccccc actggttggg gcattgccac cacctgtcag ctcctttccg ggactttcgc   3600 tttcccctc cctattgcca cggcggaact catcgccgcc tgccttgccc gctgctggac     3660
aggggctcgg ctgttgggca ctgacaattc cgtggtgttg tcggggaagc tgacgtcctt   3720
tccatggctg ctcgcctgtg ttgccacctg gattctgcgc gggacgtcct tctgctacgt   3780
cccttcggcc ctcaatccag cggaccttcc ttcccgcggc ctgctgccgg ctctgcggcc   3840
tcttccgcgt cttcgccttc gccctcagac gagtcggatc tccctttggg ccgcctcccc   3900
gcctggaatt cgagctcggt acctttaaga ccaatgactt acaaggcagc tgtagatctt   3960
agccactttt taaaagaaaa ggggggactg aagggctaa ttcactccca acgaagacaa    4020
gatctgcttt ttgcttgtac tgggtctctc tggttagacc agatctgagc ctgggagctc   4080
tctggctaac tagggaaccc actgcttaag cctcaataaa gcttgccttg agtgcttcaa   4140
gtagtgtgtg cccgtctgtt gtgtgactct ggtaactaga gatccctcag acccttttag   4200
tcagtgtgga aaatctctag                                               4220
```

<210> SEQ ID NO 5
<211> LENGTH: 4647
<212> TYPE: DNA
<213> ORGANISM: Artificial Sequence
<220> FEATURE:
<223> OTHER INFORMATION: Description of Artificial Sequence: Synthetic T-cell specific lentiviral vector

<400> SEQUENCE: 5

```
agcttaatgt agtctatgc aatactcttg tagtcttgca acatggtaac gatgagttag      60
caacatgcct tacaaggaga gaaaaagcac cgtgcatgcc gattggtgga agtaaggtgg    120
tacgatcgtg ccttattagg aaggcaacag acgggtctga catggattgg acgaaccact    180
gaattgccgc attgcagaga tattgtattt aagtgcctag ctcgatacaa taaacgggtc    240
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagaccctt ttagtcagtg tggaaaatct ctagcagtgg    420
cgcccgaaca gggacctgaa agcgaaaggg aaaccagagc tctctcgacg caggactcgg    480
cttgctgaag cgcgcacggc aagaggcgag gggcggcgac tggtgagtac gccaaaaatt    540
ttgactagcg gaggctagaa ggagagagat gggtgcgaga gcgtcagtat taagcggggg   600
agaattagat cgcgatggga aaaaattcgg ttaaggccag ggggaaagaa aaatatataaa   660 ttaaaacata tagtatgggc aagcaggag ctagaacgat tcgcagttaa tcctggcctg    720
ttagaaacat cagaaggctg tagacaaata ctgggacagc tacaaccatc ccttcagaca    780
ggatcagaag aacttagatc attatataat acagtagcaa ccctctattg tgtgcatcaa    840
aggatagaga taaaagacac caaggaagct ttagacaaga tagaggaaga gcaaaacaaa    900
agtaagacca ccgcacagca agcggccgct gatcttcaga cctggaggag gagatatgag    960
ggacaattgg agaagtgaat tatataaata taaagtagta aaaattgaac cattaggagt   1020
agcacccacc aaggcaaaga gaagagtggt gcagagagaa aaaagagcag tgggaatagg   1080
```

```
agctttgttc cttgggttct tgggagcagc aggaagcact atgggcgcag cctcaatgac   1140
gctgacggta caggccagac aattattgtc tggtatagtg cagcagcaga acaatttgct   1200
gagggctatt gaggcgcaac agcatctgtt gcaactcaca gtctggggca tcaagcagct   1260
ccaggcaaga atcctggctg tggaaagata cctaaaggat caacagctcc tggggatttg   1320
gggttgctct ggaaaactca tttgcaccac tgctgtgcct tggaatgcta gttggagtaa   1380
taaatctctg gaacagattt ggaatcacac gacctggatg gagtgggaca gagaaattaa   1440 caattcacaca agcttaatac actccttaat tgaagaatcg caaaaccagc aagaaaagaa   1500
tgaacaagaa ttattggaat tagataaatg ggcaagtttg tggaattggt ttaacataac   1560
aaattggctg tggtatataa aattattcat aatgatagta ggaggcttgg taggtttaag   1620
aatagttttt gctgtacttt ctatagtgaa tagagttagg cagggatatt caccattatc   1680
gtttcagacc cacctcccaa ccccgagggg acccgacagg cccgaaggaa tagaagaaga   1740
aggtggagag agagacagag acagatccat tcgattagtg aacggatctc gacggtatcg   1800 gttaacttttt aaaagaaaag gggggattgg ggggtacagt gcaggggaaa gaatagtaga   1860
cataatagca acagacatac aaactaaaga attacaaaaa caaattacaa aaattcaaaa   1920
ttttatcgat aagctgcatg ctgttggggt tcaaatttga gccccagctg ttagccctct   1980
gcaaagaaaa aaaaaaaaaa aaagaacaa agggcctaga tttcccttct gagccccacc   2040
ctaagatgaa gcctcttctt tcaagggagt ggggttgggg tggaggcgga tcctgtcagc   2100
tttgctctct ctgtggctgg cagtttctcc aaagggtaac aggtgtcagc tggctgagcc   2160
taggctgaac cctgagacat gctacctctg tcttctcatg gctggaggca gcctttgtaa   2220
gtcacagaaa gtagctgagg ggctctggaa aaaagacagc cagggtggag gtagattggt   2280
gcatgcagct tctgcagccc cgcgtgctag agatttaagc ctgattctgc ttaactttt   2340 cccttgactt tggcattttc actttgacat gttccctgag agcctggggg gtggggaacc   2400
agctccagct ggtgacgttt ggggccggcc caggcctagg gtgtggagga gccttgccat   2460
cgggcttcct gtctctcttc atttaagcac gactctgcag gtcgagatct aagtaagctt   2520
ttgaggggat gagggaagga gggtgggcac ggttccccg atgtgggtgt ctgaggcgaa   2580
gaagaggatg gcgagggttg cagccaccaa ccacaagagt tccttagagg ggtcacagtc   2640
tctaggaagt ttataggaag ctagtcagca gtagagaggg tgaacgcggt ggggcacatc   2700
ccgcggctgg gcttgagtgg gctgcttggg ggttatgggg agaagataaa agtgcctgtg   2760
ggaccacaga ctctcgctgt ggtggagctg ggccctctta ccctcccaag cctcgcccct   2820
catcccatcc ctgggggcca ggggtgaggg cggcaggaac ctcaaggctc tgagaaagtg   2880
cgtggtgtgt gttgccattt tggtctcttc tctttctcag tctctctttg cctcactttg   2940
gatctatgct ctgtgcatct gtcttgcttc tcagaatttc ttcttttcct ctttttttgt   3000
actacccggg atccaccggt cgccaccatg gtgagcaagg gcgaggagct gttcaccggg   3060
gtggtgccca tcctggtcga gctggacggc gacgtaaacg gccacaagtt cagcgtgtcc   3120
ggcgagggcg agggcgatgc cacctacggc aagctgaccc tgaagttcat ctgcaccacc   3180
ggcaagctgc ccgtgccctg gcccaccctc gtgaccaccc tgacctacgg cgtgcagtgc   3240
ttcagccgct accccgacca catgaagcag cacgacttct tcaagtccgc catgcccgaa   3300
ggctacgtcc aggagcgcac catcttcttc aaggacgacg gcaactacaa gacccgcgcc   3360
gaggtgaagt tcgagggcga caccctggtg aaccgcatcg agctgaaggg catcgacttc   3420
aaggaggacg gcaacatcct ggggcacaag ctggagtaca actacaacag ccacaacgtc   3480
```

```
tatatcatgg ccgacaagca gaagaacggc atcaaggtga acttcaagat ccgccacaac   3540
atcgaggacg gcagcgtgca gctcgccgac cactaccagc agaacacccc catcggcgac   3600
ggccccgtgc tgctgcccga caaccactac ctgagcaccc agtccgccct gagcaaagac   3660
cccaacgaga agcgcgatca catggtcctg ctggagttcg tgaccgccgc cgggatcact   3720
ctcggcatgg acgagctgta caagtaaagc tcgagcgaca atcaacctct ggattacaaa   3780
atttgtgaaa gattgactgg tattcttaac tatgttgctc cttttacgct atgtggatac   3840
gctgctttaa tgcctttgta tcatgctatt gcttcccgta tggctttcat tttctcctcc   3900
ttgtataaat cctggttgct gtctctttat gaggagttgt ggcccgttgt caggcaacgt   3960
ggcgtggtgt gcactgtgtt tgctgacgca acccccactg gttggggcat tgccaccacc   4020
tgtcagctcc tttccgggac tttcgctttc cccctcccta ttgccacggc ggaactcatc   4080
gccgcctgcc ttgcccgctg ctggacaggg gctcggctgt tgggcactga caattccgtg   4140
gtgttgtcgg ggaagctgac gtcctttcca tggctgctcg cctgtgttgc cacctggatt   4200
ctgcgcggga cgtccttctg ctacgtccct tcggccctca atccagcgga ccttccttcc   4260
cgcggcctgc tgccggctct gcggcctctt ccgcgtcttc gccttcgccc tcagacgagt   4320
cggatctccc tttgggccgc ctccccgcct ggaattcgag ctcggtacct ttaagaccaa   4380
tgacttacaa ggcagctgta gatcttagcc actttttaaa agaaaagggg ggactggaag   4440
ggctaattca ctcccaacga agacaagatc tgcttttttgc ttgtactggg tctctctggt   4500
tagaccagat ctgagcctgg gagctctctg gctaactagg gaacccactg cttaagcctc   4560
aataaagctt gccttgagtg cttcaagtag tgtgtgcccg tctgttgtgt gactctggta   4620
actagagatc cctcagaccc ttttagt                                        4647
```

```
<210> SEQ ID NO 6
<211> LENGTH: 5030
<212> TYPE: DNA
<213> ORGANISM: Artificial Sequence
<220> FEATURE:
<223> OTHER INFORMATION: Description of Artificial Sequence: Synthetic
      lentiviral vector containing a viral HA coding
      sequence

<400> SEQUENCE: 6
```

```
ttaatgtagt cttatgcaat actcttgtag tcttgcaaca tggtaacgat gagttagcaa     60
catgccttac aaggagagaa aaagcaccgt gcatgccgat tggtggaagt aaggtggtac    120
gatcgtgcct tattaggaag gcaacagacg ggtctgacat ggattggacg aaccactgaa    180
ttgccgcatt gcagagatat tgtatttaag tgcctagctc gatacaataa acgggtctct    240
ctggttagac cagatctgag cctgggagct ctctggctaa ctagggaacc cactgcttaa    300
gcctcaataa agcttgcctt gagtgcttca agtagtgtgt gcccgtctgt tgtgtgactc    360
tggtaactag agatccctca gaccctttta gtcagtgtgg aaaatctcta gcagtggcgc    420
ccgaacaggg acctgaaagc gaaagggaaa ccagagctct ctcgacgcag gactcggctt    480
gctgaagcgc gcacggcaag aggcgagggg cggcgactgg tgagtacgcc aaaaattttg    540
actagcggag gctagaagga gagagatggg tgcgagagcg tcagtattaa gcgggggaga    600
attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
```

```
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcct caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcggtt   1800
aacttttaaa agaaaagggg ggattggggg gtacagtgca ggggaaagaa tagtagacat   1860
aatagcaaca gacatacaaa ctaaagaatt acaaaaacaa attacaaaaa ttcaaaattt   1920
tatcgatcac gagactagcc tcgagaagct tgatatcgaa ttcccacggg gttggggttg   1980
cgccttttcc aaggcagccc tgggtttgcg cagggacgcg gctgctctgg gcgtggttcc   2040
gggaaacgca gcggcgccga ccctgggtct cgcacattct tcacgtccgt tcgcagcgtc   2100
acccggatct tcgccgctac ccttgtgggc ccccgcgga cgcttcctgc tccgcccta    2160
agtcgggaag gttccttgcg gttcgcggcg tgccggacgt gacaaacgga agccgcacgt   2220
ctcactagta ccctcgcaga cggacagcgc caggagcaa tggcagcgcg ccgaccgcga   2280
tgggctgtgg ccaatagcgg ctgctcagcg gggcgcgccg agagcagcgg ccgggaaggg   2340
gcggtgcggg aggcggggtg tggggcggta gtgtgggccc tgttcctgcc cgcgcggtgt   2400
tccgcattct gcaagcctcc ggagcgcacg tcggcagtcg gctccctcgt tgaccgaatc   2460
accgacctct ctccccaggg ggatccaccg gtatgaaggc aaacctactg gtcctgttat   2520
gtgcacttgc agctgcagat gcagacacaa tatgtatagg ctaccatgcg aacaattcaa   2580
ccgcacactgt tgacacagta ctcgagaaga atgtgacagt gacacactct gttaacctgc   2640
tcgaagacag ccacaacgga aaactatgta gattaaaagg aatagcccca ctacaattgg   2700
ggaaatgtaa catcgccgga tggctcttgg gaaacccaga atgcgaccca ctgcttccag   2760
tgagatcatg gtcctacatt gtagaaacac caaactctga gaatggaata tgttatccag   2820
gagatttcat cgactatgag gagctgaggg agcaattgag ctcagtgtca tcattcgaaa   2880
gattcgaaat atttcccaaa gaaagctcat ggcccaacca caacacaaac ggagtaacgg   2940
cagcatgctc ccatgagggg aaaagcagtt tttacagaaa tttgctatgg ctgacggaga   3000
aggagggctc atacccaaag ctgaaaaatt cttatgtgaa caaaaagggg aaagaagtcc   3060
ttgtactgtg gggtattcat cacccggcta acagtaagga acaacagaat ctctatcaga   3120
atgaaaatgc ttatgtctct gtagtgactt caaattataa caggagattt acccccggaaa   3180
tagcagaaag acccaaagta agagatcaag ctgggaggat gaactattac tggaccttgc   3240
```

```
taaaacccgg agacacaata atatttgagg caaatggaaa tctaatagca ccaatgtatg    3300
ctttcgcact gagtagaggc tttgggtccg gcatcatcac ctcaaacgca tcaatgcatg    3360
agtgtaacac gaagtgtcaa acaccctgg gagctataaa cagcagtctc ccttaccaga     3420
atatacaccc agtcacaata ggagagtgcc caaaatacgt caggagtgcc aaattgagga    3480
tggttacagg actaaggaac attccgtcca ttcaatccag aggcctattt ggagccattg    3540
ccggttttat tgaagggga tggactggaa tgatagatgg atggtatggt tatcatcatc     3600
agaatgaaca gggatcaggc tatgcagcgg atcaaaaaag cacacaaaat gccattaacg    3660
ggattacaaa caaggtgaac actgttatcg agaaaatgaa cattcaattc acagctgtgg    3720
gtaaagaatt caacaaatta gaaaaaagga tggaaaattt aaataaaaaa gttgatgatg    3780
gatttctgga catttggaca tataatgcag aattgttagt tctactggaa aatgaaagga    3840
ctctggattt ccatgactca aatgtgaaga tctgtatga gaaagtaaaa agccaattaa     3900
agaataatgc caaagaaatc ggaaatggat gttttgagtt ctaccacaag tgtgacaatg    3960
aatgcatgga aagtgtaaga aatgggactt atgattatcc caaatattca gaagagtcaa    4020
agttgaacag ggaaaaggta gatggagtga aattggaatc aatggggatc tatcagattc    4080
tggcgatcta ctcaactgtc gccagttcac tgtgagtcga caatcaacct ctggattaca    4140
aaatttgtga agattgact ggtattctta actatgttgc tccttttacg ctatgtggat      4200
acgctgcttt aatgcctttg tatcatgcta ttgcttcccg tatggctttc atttctcct     4260
ccttgtataa atcctggttg ctgtctcttt atgaggagtt gtggcccgtt gtcaggcaac    4320
gtggcgtggt gtgcactgtg tttgctgacg caacccccac tggttgggc attgccacca    4380
cctgtcagct ccttccggg actttcgctt tccccctccc tattgccacg gcggaactca    4440
tcgccgcctg ccttgcccgc tgctggacag gggctcggct gttgggcact gacaattccg    4500
tggtgttgtc ggggaagctg acgtcctttc catggctgct cgcctgtgtt gccacctgga   4560
ttctgcgcgg gacgtccttc tgctacgtcc cttcggccct caatccagcg gaccttcctt   4620
cccgcggcct gctgccggct ctgcggcctc ttccgcgtct tcgccttcgc cctcagacga   4680
gtcggatctc ccttgggcc gcctccccgc ctggaattcg agctcggtac ctttaagacc    4740
aatgacttac aaggcagctg tagatcttag ccacttttta aaagaaaagg ggggactgga   4800
agggctaatt cactcccaac gaagacaaga tctgcttttt gcttgtactg ggtctctctg   4860
gttagaccag atctgagcct gggagctctc tggctaacta gggaacccac tgcttaagcc   4920
tcaataaagc ttgccttgag tgcttcaagt agtgtgtgcc cgtctgttgt gtgactctgg   4980
taactagaga tccctcagac ccttttagtc agtgtggaaa atctctagca               5030
```

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Phe Glu Arg Phe Glu Ile Phe Pro Lys
1               5                   10

TREATING IMMUNODEFICIENCIES BY INTRATHYMIC INJECTION OF NUCLEOTIDE SEQUENCES

FIELD OF THE INVENTION

The invention relates to the use of viral vectors for the preparation of dugs for the prevention or treatment of genetic immunodeficiencies, acquired immunodeficiencies, autoimmune diseases, or for the induction of immune tolerance of the organism to self or non-self gene products, cells or tissues.

BACKGROUND OF THE INVENTION

The thymus is a bilobate organ derived from embryonic endoderm and mesoderm differentiation and is located just above the heart (reviewed in [1a]). It is the primary organ for maturation of T cells. This process involves the interaction between developing thymocytes and thymic stromal cells. Thymic stromal cells which forms the thymic architecture, have been classified according to their anatomical localization. They encompass a very diverse array of cell types, including cortical and medullar epithelial cells, fibroblasts, macrophages and dendritic cells (reviewed in [2a]). Stromal cells control the differentiation of haematopoietic precursors derived from the liver or the bone marrow into T lymphocytes: T-cell differentiation is defined by the acquisition of maturation markers such as CD4, CD8 and the T-cell receptor complex (TCR), which conditions the reactivity of immature thymocytes with thymic stromal cells. The early thymocyte progenitors entering the thymus do not express T-cell-specific molecules, such as CD3, the alpha or beta-chain of the TCR, or the CD4 and CD8 molecules. These $CD4^-CD8^-$cells, referred to as double-negative (DN) cells, then become $CD4^+ CD8^+$, the so-called double-positive (DP) stage, and then progressively acquire TCR molecules. The final maturation of T-cells involves the selective loss of either the CD4 or the CD8 molecules to generate fully mature single-positive (SP) cells with cytotoxic/suppressor or helper/regulator function, respectively.

During this process, the TCR-mediated positive and negative selection of T cells ensures the selection of a diverse TCR repertoire able to react with foreign peptide presented by autologous major histocompatibility complex (MHC) molecules, but tolerant to self-antigens. This property renders the thymus an attractive site for manipulation of T-cell tolerance. To date, results on tolerance induction via direct manipulation of the thymus have been scarce (reviewed in [3a]). However, previous studies using intrathymic (IT) injection of pancreatic islet cells [4a], soluble antigens [5a] or adenoviral vectors [6a, 7a] have shown that induction of tolerance to foreign antigens in non-immunosuppressed animals is feasible. Since the production and maturation of thymocytes may be a life-long process, a major drawback to the utilisation of soluble antigens or adenoviruses is their short-term expression in the thymus [8a]. Indeed, modulation of the selection process should stop upon the disappearance of the antigen, which might be a problem for long-term tolerance induction.

Due to their ability to infect resting cells and to stably integrate into the genome, lentiviral vectors represent powerful new tools for long-term expression of a given transgene in vivo [9a]. Lentiviral vectors have been used successfully in vivo to infect hepatocytes and muscle cells [10a], antigen-presenting cells [11a, 12a], as well as cells of the central nervous system [13a].

The inventors postulate that lentiviral vectors might be better suited than adenoviral vectors for long-term IT expression of a foreign gene. They therefore investigated the pattern of infection of a ubiquitous lentiviral vector after IT injection.

Young adult mice were injected in the thymus with lentiviral vectors expressing eGFP or the hemaglutinin of the Influenza virus under the control of the ubiquitous phospho glycerite kinase promoter. Thymi were examined 5 to 90 days thereafter directly under a UV-light microscope and by flow cytometry. Intrathymic injection of lentiviral vectors predominantly results in infection of stromal cells that could be detected for at least 3 months. Importantly, hemaglutinin expression by thymic stromal cells mediated negative selection of thymocytes expressing the cognate T-cell receptor. In addition and despite the low multiplicity of infection, transduced thymocytes were also detected, even 30 days after injection.

SUMMARY OF THE INVENTION

Thus, the present invention relies on the demonstration made by the Inventors that thymic stromal cells are massively and persistently infected, and that developing thymocytes also exhibit a significant level of infection. Moreover, the Inventors show that IT injection of a lentiviral vector encoding the cognate antigen in TCR-transgenic (Tg) mice leads to negative selection of developing thymocytes.

These results demonstrate that intrathymic delivery of a viral vector, such as a lentiviral vector, is an efficient means for stable expression of a foreign gene in the thymus.

Thus, the main goal of the present invention is to provide new tools for induction of tolerance to a specific antigen and for gene therapy of severe combined immunodeficiencies, using gene delivery by intrathymic administration.

The invention relates to the use of viral vectors able to stably integrate into the genome of thymic stromal cells, or of intrathymic lymphocytes or lymphocytes precursors, for the manufacture of a medicine intended for the prevention or treatment of genetic immunodeficiencies, acquired immunodeficiencies, or for the induction of immune tolerance of the organism to self or non-self gene products, cells or tissues, or for the prevention or treatment of autoimmune diseases.

The invention relates more particularly to the use of viral vectors as defined above, characterized in that they are chosen among retroviruses, lentiviruses, spumaviruses, or adeno-associated viruses.

The invention concerns more particularly the use of viral vectors as defined above, characterized in that they are lentiviral vectors corresponding to sequences derived from the human immunodeficiency virus type-1.

Lentiviral vectors which can be used in the present invention are or derived from the lentiviral vectors already, for example in the review article of C. Delenda, in The Journal of Gene Medicine, 2004; 6: S125-S138.

The invention relates more particularly to the use as defined above of lentiviral vectors comprising the U3 region of the Rous sarcoma virus, R-U 5 region of the 3' long terminal repeat (LTR), part of gag, central polypurine tract, R-U5 region of the 5' LTR from HIV type-1, but which do not comprise the U3 region of the 3' LTR, half of gag, pol, nef, vpr, vpu, env, U3 region of the 5' LTR from said HIV type-1.

The invention also relates to the use as defined above, of viral vectors containing a predetermined recombinant nucleotide sequence for the induction of immune tolerance of the organism to self or non-self gene products, cells or tissues, or for the prevention or treatment of genetic immunodeficiencies, acquired immunodeficiencies, or autoimmune diseases, said predetermined recombinant nucleotide sequence being under the control of elements directing its expression in eukaryotic cells.

The invention relates more particularly to the use as defined above, of lentiviral vectors wherein the predetermined recombinant nucleotide sequence is inserted between the central polypurine tract and the 3' LTR.

The invention also relates to the use of viral vectors as defined above, for the manufacture of a medicine for the transformation of thymic stromal cells in the frame of the induction of immune tolerance of the organism to self or non-self gene products, cells or tissues, and for prevention or treatment of autoimmune diseases, and/or for the transformation of intrathymic lymphocytes or lymphocytes precursors, in the frame of the prevention or treatment of genetic immunodeficiencies, or acquired immunodeficiencies.

The invention relates more particularly to the use of viral vectors as defined above, for the manufacture of a medicine intended for intrathymic administration.

The invention also concerns more particularly the use of viral vectors as defined above, for the manufacture of a medicine intended for intrathymic administration for the transformation of thymic stromal cells in the frame of the induction of immune tolerance of the organism to self or non-self gene products, cells or tissues, and for the prevention or treatment of autoimmune diseases.

In this respect, the invention relates more particularly to the use of viral vectors as defined above, for the manufacture of a medicine intended for intrathymic administration for the transformation of thymic stromal cells in the frame of the prevention or the treatment of autoimmune diseases, such as myasthenia gravis, multiple sclerosis, rheumatoid arthritis, Lupus, colitis, inflammatory muscular diseases, inflammatory occular diseases, or type-1 diabetes.

The invention concerns more particularly the use of viral vectors as defined above, for the manufacture of a medicine intended for intrathymic administration for the transformation of thymic stromal cells, said viral vectors containing predetermined recombinant nucleotide sequences selected from:
- myelin auto-antigen coding sequences, in the frame of the prevention or the treatment of myasthenia gravis,
- acetylcholine receptor coding sequences, in the frame of the prevention or the treatment of multiple sclerosis,
- or insulin coding sequences, in the frame of the prevention or the treatment of type-1 diabetes.

The invention also concerns more particularly the use as defined above of the ubiquitous lentiviral vector containing a mammalian Insulin coding sequence such as the vector pRRL.sin. cppt.PGK.Ins2.GTX.eGFP.pre corresponding to the following sequence SEQ ID NO:1:

```
SEQ ID NO: 1:
ttaatgtagtcttatgcaatactcttgtagtcttgcaacatggtaacgatgagttagcaacatgccttacaagga gagaaaaagcaccgtgcatgccgattggtggaagtaaggtggtacgatcgtgccttattaggaaggcaacagacg ggtctgacatggattggacgaaccactgaattgccgcattgcagagatattgtatttaagtgcctagctcgatac aataaacgggtctctctggttagaccagatctgagcctgggagctctctggctaactagggaacccactgcttaa gcctcaataaagcttgccttgagtgcttcaagtagtgtgtgcccgtctgttgtgtgactctggtaactagagatc cctcagaccctttagtcagtgtggaaaatctctagcagtggcgcccgaacagggacctgaaagcgaaagggaaa ccagagctctctcgacgcaggactcggcttgctgaagcgcgcacggcaagaggcgaggggcggcgactggtgagt acgccaaaaattttgactagcggaggctagaaggagagagatgggtgcgagagcgtcagtattaagcgggggaga attagatcgcgatgggaaaaaattcggttaaggccagggggaaagaaaaaatataaattaaaacatatagtatgg gcaagcagggagctagaacgattcgcagttaatcctggcctgttagaaacatcagaaggctgtagacaaatactg ggacagctacaaccatcccttcagacaggatcagaagaacttagatcattatataatacagtagcaaccctctat tgtgtgcatcaaaggatagagataaaagacaccaaggaagctttagacaagatagaggaagagcaaaacaaaagt aagaccaccgcacagcaagcggccgctgatcttcagacctggaggaggagatatgagggacaattggagaagtga attatataaatataaagtagtaaaaattgaaccattaggagtagcacccaccaaggcaaagaagaagagtggtgca gagagaaaaagagcagtgggaataggagctttgttccttgggttcttgggagcagcaggaagcactatgggcgc agcctcaatgacgctgacggtacaggccagacaattattgtctggtatagtgcagcagcagaacaatttgctgag ggctattgaggcgcaacagcatctgttgcaactcacagtctggggcatcaagcagctccaggcaagaatcctggc tgtggaaagataccctaaaggatcaacagctcctggggatttggggttgctctggaaaactcatttgcaccactgc tgtgccttggaatgctagttggagtaataaatctctggaacagatttggaatcacacgacctggatggagtggga cagagaaattaacaattacacaagcttaatacactccttaattgaagaatcgcaaaaccagcaagaaaagaatga acaagaattattggaattagataaatgggcaagtttgtggaattggtttaacataacaaattggctgtggtatat aaaattattcataatgatagtaggaggcttggtaggtttaagaatagttttgctgtactttctatagtgaatag agttaggcagggatattcaccattatcgtttcagacccacctcccaaccccgaggggacccgacaggcccgaagg aatagaagaagaaggtggagagagagacagagacagatccattcgattagtgaacggatctcgacggtatcggtt
```

-continued

```
aacttttaaaagaaaaggggggattgggggggtacagtgcaggggaaagaatagtagacataatagcaacagacat
acaaactaaagaattacaaaaacaaattacaaaaattcaaaattttatcgatcacgagactagcctcgagaagct
tgatatcgaattcccacggggttgggggttgcgccttttccaaggcagccctgggtttgcgcagggacgcggctgc
tctgggcgtggttccgggaaacgcagcggcgccgaccctgggtctcgcacattcttcacgtccgttcgcagcgtc
acccggatcttcgccgctaccttgtgggccccggcgacgcttcctgctccgcccctaagtcgggaaggttcc
ttgcggttcgcggcgtgccggacgtgacaaacggaagccgcacgtctcactagtaccctcgcagacggacagcgc
cagggagcaatggcagcgcgccgaccgcgatgggctgtggccaatagcggctgctcagcggggcgcgccgagagc
agcggccgggaaggggcggtgcgggaggcggggtgtggggcggtagtgtgggccctgttcctgcccgcgcggtgt
tccgcattctgcaagcctccggagcgcacgtcggcagtcggctccctcgttgaccgaatcaccgacctctctccc
caggggggatcctagacaacatggccctgtggatgcgcttcctgcccctgctggccctgctcttcctctgggagtc
ccacccacccaggcttttgtcaagcagcacctttgtggttccacctggtggaggctctctacctggtgtgtgg
ggagcgtggcttcttctacacacccatgtcccgccgtgaagtggaggacccacaagtggcacaactggagctggg
tggaggcccgggagcaggtgaccttcagaccttggcactggaggtggcccagcagaagcgtggcattgtagatca
gtgctgcaccagcatctgctccctctaccagctggagaactactgcaactagacactagtccggcgggtttctga
catccggcgggtttctgacatccggcgggtttctgacatccggcgggttttctgacatccggcgggtgaattcttc
tgacatccggcgggtttctgacatccggcgggtttctgacatccggcgggtttctgacatccggcgggtttctga
catccggcgggtgactcacaaccccagaaacagacatccatggtgagcaagggcgaggagctgttcaccggggtg
gtgcccatcctggtcgagctggacggcgacgtaaacggccacaagttcagcgtgtccggcgagggcgagggcgat
gccacctacggcaagctgaccctgaagttcatctgcaccaccggcaagctgcccgtgccctggcccaccctcgtg
accaccctgacctacggcgtgcagtgcttcagccgctaccccgaccacatgaagcagcacgacttcttcaagtcc
gccatgcccgaaggctacgtccaggagcgcaccatcttcttcaaggacgacggcaactacaagacccgcgccgag
gtgaagttcgagggcgacaccctggtgaaccgcatcgagctgaagggcatcgacttcaaggaggacggcaacatc
ctggggcacaagctggagtacaactacaacagccacaacgtctatatcatggccgacaagcagaagaacggcatc
aaggtgaacttcaagatccgccacaacatcgaggacggcagcgtgcagctcgccgaccactaccagcagaacacc
cccatcggcgacggccccgtgctgctgcccgacaaccactacctgagcacccagtccgccctgagcaaagacccc
aacgagaagcgcgatcacatggtcctgctggagttcgtgaccgccgccgggatcactctcggcatggacgagctg
tacaagtaaagcgtcttcgaagtcggatccgtcgacaatcaacctctggattacaaaatttgtgaaagattgact
ggtattcttaactatgttgctccttttacgctatgtggatacgctgctttaatgcctttgtatcatgctattgct
tcccgtatggctttcattttctcctccttgtataaatcctggttgctgtctctttatgaggagttgtggcccgtt
gtcaggcaacgtggcgtggtgtgcactgtgtttgctgacgcaaccccactggttggggcattgccaccacctgt
cagctcctttccgggactttcgctttccccctccctattgccacggcggaactcatcgccgctgccttgcccgc
tgctggacaggggctcggctgttgggcactgacaattccgtggtgttgtcggggaagctgacgtcctttccatgg
ctgctcgcctgtgttgccacctggattctgcgcgggacgtccttctgctacgtcccttcggccctcaatccagcg
gaccttccttcccgcggcctgctgccggctctgcggcctcttccgcgtcttcgccttcgccctcagacgagtcgg
atctccctttgggccgcctccccgcctggaattcgagctcggtacctttaagaccaatgacttacaaggcagctg
tagatcttagccactttttaaaagaaaaggggggactggaagggctaattcactcccaacgaagacaagatctgc
ttttttgcttgtactgggtctctctggttagaccagatctgagcctgggagctctctggctaactagggaacccac
tgcttaagcctcaataaagcttgccttgagtgcttcaagtagtgtgtgcccgtctgttgtgtgactctggtaact
agagatccctcagaccctttagtcagtgtggaaaatctctagca
```

The invention also relates more particularly to the use of viral vectors as defined above, for the manufacture of a medicine intended for intrathymic administration for the transformation of thymic stromal cells in the frame of the prevention or the treatment of graft rejection, such as solid organ, cell or tissue allogeneic transplant rejection, hematopoietic stein cell transplant rejection, or rejection of therapeutic transgene or gene corrected products.

In this respect, the invention concerns more particularly the use of viral vectors as defined above, for the manufacture of a medicine intended for intrathymic administration for the transformation of thymic stromal cells, said viral vectors containing predetermined recombinant nucleotide sequences selected from alloantigen coding sequences, such as molecules from human major histocompatibility complex like the leukocyte antigen A2, human factor VIII, human factor IX, dystrophin, erythropoietin, in the frame of the prevention or the treatment of rejections mentioned above.

The invention also concerns more particularly the use of viral vectors as defined above, for the manufacture of a medicine intended for intrathymic administration for the transformation of intrathymic lymphocytes or lymphocytes precursors in the frame of the treatment of immune defects such as genetic immunodeficiencies and acquired immunodeficiencies.

The invention also relates more particularly to the use of viral vectors as defined above, for the treatment of genetic immunodeficiencies selected from severe combined immunodeficiencies (SCID), such as ADA-deficiency (adenosine deaminase), X-SCID (X linked SCID), ZAP-70 deficiency, Rag ½ deficiency, Jak3 deficiency, IL7RA deficiency or CD3 deficiencies.

The invention concerns more particularly the use of viral vectors as defined above, for the manufacture of a medicine intended for intrathymic administration for the transformation of intrathymic lymphocytes or lymphocytes precursors, said viral vectors containing predetermined recombinant nucleotide sequences selected from:

the ADA coding sequence, in the frame of the prevention or the treatment of ADA-deficiency, the IL2RG coding sequence, in the frame of the prevention or the treatment of X-SCID, the ZAP-70 coding sequence, in the frame of the prevention or the treatment ZAP-70 deficiency, the Rag ½ coding sequence, in the frame of the prevention or the treatment of Rag ½ deficiency, the Jak3 coding sequence, in the frame of the prevention or the treatment of Jak3 deficiency, the IL7RA coding sequence, in the frame of the prevention or the treatment of IL7RA deficiency, the CD3 delta sequence, or the CD3 epsilon sequence, in the flame of the prevention or the treatment of CD3 deficiencies.

The invention also concerns more particularly the use as defined above of the T-cell specific lentiviral vector containing a mammalian ZAP-70 coding sequence such as the vector pRRL.sin. cppt.CD4pmE.hZAP-70.IRES.eGFP.pre corresponding to the following sequence SEQ ID NO:2:

```
SEQ ID NO: 2:
ttaatgtagtcttatgcaatactcttgtagtcttgcaacatggtaacgatgagttagcaacatgccttacaagga gagaaaaagcaccgtgcatgccgattggtggaagtaaggtggtacgatcgtgccttattaggaaggcaacagacg ggtctgacatggattggacgaaccactgaattgccgcattgcagagatattgtatttaagtgcctagctcgatac aataaacgggtctctctggttagaccagatctgagcctgggagctctctggctaactagggaacccactgcttaa gcctcaataaagcttgccttgagtgcttcaagtagtgtgtgcccgtctgttgtgtgactctggtaactagagatc cctcagaccctttagtcagtgtggaaaatctctagcagtggcgcccgaacagggacctgaaagcgaaagggaaa ccagagctctctcgacgcaggactcggcttgctgaagcgcgcacggcaagaggcgaggggcggcgactggtgagt acgccaaaaattttgactagcggaggctagaaggagagagatgggtgcgagagcgtcagtattaagcgggggaga attagatcgcgatgggaaaaaattcggttaaggccaggggaaagaaaaaatataaattaaaacatatagtatgg gcaagcagggagctagaacgattcgcagttaatcctggcctgttagaaacatcagaaggctgtagacaaatactg ggacagctacaaccatcccttcagacaggatcagaagaacttagatcattatataatacagtagcaaccctctat tgtgtgcatcaaaggatagagataaaagacaccaaggaagctttagacaagatagaggaagagcaaaacaaaagt aagaccaccgcacagcaagcggccgctgatcttcagacctggaggaggagatatgagggacaattggagaagtga attatataaatataaagtagtaaaaattgaaccattaggagtagcacccaccaaggcaaagagaagagtggtgca gagagaaaaagagcagtgggaataggagctttgttccttgggttcttgggagcagcaggaagcactatgggcgc agcctcaatgacgctgacggtacaggccagacaattattgtctggtatagtgcagcagcagaacaatttgctgag ggctattgaggcgcaacagcatctgttgcaactcacagtctggggcatcaagcagctccaggcaagaatcctggc tgtggaaagatacctaaaggatcaacagctcctggggatttggggttgctctggaaaactcatttgcaccactgc tgtgccttggaatgctagttggagtaataaatctctggaacagatttggaatcacacgacctggatggagtggga cagagaaattaacaattacacaagcttaatacactccttaattgaagaatcgcaaaaccagcaagaaaagaatga acaagaattattggaattagataaatgggcaagtttgtggaattggtttaacataacaaattggctgtggtatat aaaattattcataatgatagtaggaggcttggtaggtttaagaatagttttgctgtactttctatagtgaatag agttaggcagggatattcaccattatcgtttcagacccacctcccaaccccgaggggacccgacaggcccgaagg
```

-continued aatagaagaagaaggtggagagagagacagagacagatccattcgattagtgaacggatctcgacggtatcggtt aacttttaaaagaaaaggggggattgggggtacagtgcaggggaaagaatagtagacataatagcaacagacat acaaactaaagaattacaaaaacaaattacaaaaattcaaaattttatcgataagctgcatgctgttggggttca aatttgagccccagctgttagccctctgcaaagaaaaaaaaaaaaaaaaagaacaaagggcctagatttcccttt ctgagccccaccctaagatgaagcctcttctttcaagggagtggggttggggtggaggcggatcctgtcagctttt gctctctctgtggctggcagtttctccaaagggtaacaggtgtcagctggctgagcctaggctgaaccctgagac atgctacctctgtcttctcatggctggaggcagcctttgtaagtcacagaaagtagctgaggggctctggaaaaa agacagccagggtggaggtagattggtgcatgcagcttctgcagcccgcgtgctagagatttaagcctgattct gcttaacttttttcccttgactttggcattttcactttgacatgttccctgagagcctgggggggtgggaaccagc tccagctggtgacgtttggggccggcccaggcctaggtgtggaggagccttgccatcgggcttcctgtctctct tcatttaagcacgactctgcaggtcgagatctaagtaagcttgatcatgccagaccccgcggcgcacctgcccttt cttctacggcagcatctcgcgtgccgaggccgaggagcacctgaagctggcgggcatggcggacgggctcttcct gctgcgccagtgcctgcgctcgctgggcggctatgtgctgtcgctcgtgcacgatgtgcgcttccaccactttcc catcgagcgccagctcaacggcacctacgccattgccggcggcaaagcgcactgtggaccggcagagctctgcga gttctactcgcgcgaccccgacgggctgccctgcaacctgcgcaagccgtgcaaccggccgtcgggcctcgagcc gcagccgggggtcttcgactgcctgcgagacgccatggtgcgtgactacgtgcgccagacgtggaagctggaggg cgaggccctggagcaggccatcatcagccaggccccgcaggtggagaagctcattgctacgacggcccacgagcg gatgccctggtaccacagcagcctgacgcgtgaggaggccgagcgcaaactttactctggggcgcagaccgacgg caagttcctgctgaggccgcggaaggagcagggcacatacgccctgtccctcatctatgggaagacggtgtacca ctacctcatcagccaagacaaggcgggcaagtactgcattcccgagggcaccaagtttgacacgctctggcagct ggtggagtatctgaagctgaaggcggacgggctcatctactgcctgaaggaggcctgccccaacagcagtgccag caacgcctcaggggctgctgctcccacactcccagcccacccatccacgttgactcatcctcagagacgaatcga caccctcaactcagatggatacacccctgagccagcacgcataacgtccccagacaaaccgcggccgatgcccat ggacacgagcgtgtatgagagcccctacagcgacccagaggagctcaaggacaagaagctcttcctgaagcgcga taacctcctcatagctgacattgaacttggctgcggcaactttggctcagtgcgccagggcgtgtaccgcatgcg caagaagcagatcgacgtggccatcaaggtgctgaagcagggcacggagaaggcagacacggaagagatgatgcg cgaggcgcagatcatgcaccagctggacaaccctacatcgtgcggctcattggcgtctgccaggccgaggccct catgctggtcatggagatggctgggggcgggccgctgcacaagttcctggtcggcaagagggaggagatccctgt gagcaatgtggccgagctgctgcaccaggtgtccatgggatgaagtacctggaggagaagaactttgtgcaccg tgacctggcggcccgcaacgtcctgctggttaaccggcactacgccaagatcagcgactttggcctctccaaagc actgggtgccgacgacagctactacactgcccgctcagcagggaagtggccgctcaagtggtacgcacccgaatg catcaacttccgcaagttctccagccgcagcgatgtctggagctatggggtcaccatgtgggaggccttgtccta cggccagaagccctacaagaagatgaaagggccggaggtcatggccttcatcgagcagggcaagcggatggagtg cccaccagagtgtccacccgaactgtacgcactcatgagtgactgctggatctacaagtgggaggatcgccccga cttcctgaccgtggagcagcgcatgcgagcctgttactacagcctggccagcaaggtggaagggccccaggcag cacacagaaggctgaggctgcctgtgcctgatacgtaaattccgccctctccctccccccccccctaacgttact ggccgaagccgcttggaataaggccggtgtgcgtttgtctatatgttattttccaccatattgccgtctttttggc aatgtgagggcccggaaacctggccctgtcttcttgacgagcattcctagggggtctttcccctctcgccaaagga atgcaaggtctgttgaatgtcgtgaaggaagcagttcctctggaagcttcttgaagacaaacaacgtctgtagcg acccttttgcaggcagcggaaccccccacctggcgacaggtgcctctgcggccaaaagccacgtgtataagataca -continued

```
cctgcaaaggcggcacaacccagtgccacgttgtgagttggatagttgtggaaagagtcaaatggctctcctca agcgtattcaacaagggctgaaggatgcccagaaggtaccccattgtatgggatctgatctggggcctcggtgc acatgctttacatgtgtttagtcgaggttaaaaaacgtctaggcccccgaaccacggggacgtggttttcctt gaaaaacacgatgataatatggccacaaccatggtgagcaagggcgaggagctgttcaccggggtggtgcccatc ctggtcgagctggacggcgacgtgaacggccacaagttcagcgtgtccggcgagggcgagggcgatgccacctac ggcaagctgaccctgaagttcatctgcaccaccggcaagctgcccgtgccctggcccaccctcgtgaccaccctg acctacggcgtgcagtgcttcagccgctaccccgaccacatgaagcagcacgacttcttcaagtccgccatgccc gaaggctacgtccaggagcgcaccatcttcttcaaggacgacggcaactacaagacccgcgccgaggtgaagttc gagggcgacaccctggtgaaccgcatcgagctgaagggcatcgacttcaaggaggacggcaacatcctggggcac aagctggagtacaactacaacagccacaacgtctatatcatggccgacaagcagaagaacggcatcaaggtgaac ttcaagatccgccacaacatcgaggacggcagcgtgcagctcgccgaccactaccagcagaacacccccatcggc gacggccccgtgctgctgcccgacaaccactacctgagcacccagtccgccctgagcaaagaccccaacgagaag cgcgatcacatggtcctgctggagttcgtgaccgccgcgggatcactcacggcatggacgagctgtacaagtaa agcggccgccagcacagtggtcgacggtaccgcgggcccggtcgagcgacaatcaacctctggattacaaaattt gtgaaagattgactggtattcttaactatgttgctccttttacgctatgtggatacgctgctttaatgcctttgt atcatgctattgcttcccgtatggctttcattttctcctccttgtataaatcctggttgctgtctcttatgagg agttgtggcccgttgtcaggcaacgtggcgtggtgtgcactgtgtttgctgacgcaacccccactggttggggca ttgccaccacctgtcagctccttccgggactttcgctttcccctccctattgccacggcggaactcatcgccg cctgccttgcccgctgctggacaggggctcggctgtgggcactgacaattccgtggtgttgtcggggaagctga cgtcctttccatggctgctcgcctgtgttgccacctggattctgcgcgggacgtccttctgctacgtcccttcgg ccctcaatccagcggaccttccttcccgcggcctgctgccggctctgcggcctcttccgcgtcttcgccttcgcc ctcagacgagtcggatctccctttgggccgcctcccccgcctggaattcgagctcggtaccttttaagaccaatgac ttacaaggcagctgtagatcttagccactttttaaaagaaaaggggggactggaagggctaattcactcccaacg aagacaagatctgctttttgcttgtactgggtctctctggttagaccagatctgagcctgggagctctctggcta actagggaacccactgcttaagcctcaataaagcttgccttgagtgcttcaagtagtgtgtgcccgtctgttgtg tgactctggtaactagagatccctcagaccctttagtcagtgtggaaaatctctagcag
```

The invention also relates more particularly to the use of viral vectors as defined above, for the treatment of acquired immunodeficiencies arising from HIV infection.

The invention concerns more particularly the use of viral vectors as defined above, for the manufacture of a medicine intended for intrathymic administration for the transformation of intrathymic lymphocytes or lymphocytes precursors, said viral vectors containing predetermined recombinant nucleotide sequence selected from inhibitory peptide such as membrane-bound gp41-derived fusion inhibitor, dominant negative Tat, Rev, Env sequences, or ribozymes, anti-sense HIV RNAs or siRNAs, in the frame of the treatment of acquired immunodeficiencies arising from HIV infection.

The invention relates more particularly to the use of viral vectors as defined above, for the manufacture of a medicine intended for intrathymic administration for the transformation of intrathymic lymphocytes, said viral vectors being T-cell specific lentiviral vectors, i.e. lentiviral vectors having the property of expressing a therapeutic transgene specifically in T lymphocytes.

In this respect, the invention concerns more particularly the use as mentioned above, of T-cell specific lentiviral vectors corresponding to lentiviral vectors as defined above, wherein a T-cell specific DNA sequence responsible for the T-cell specificity of the lentiviral vectors, is integrated, said T-cell specific DNA sequence being advantageously chosen among sequences from the human or murine CD4 gene, such as from the CD4 gene regulatory sequences corresponding to:
the minimal proximal CD4 promoter and the murine enhancer, and having the following sequence:
SEQ ID NO:3: CD4pmE (murine Enhancer minimal CD4 promoter):

```
tgttggggttcaaatttgagccccagctgttagccctctgcaaagaaaaaaaaaaaaaaaaagaacaaagggcc tagatttcccttctgagccccaccctaagatgaagcctcttctttcaagggagtgggggttggggtggaggcggat cctgtcagctttgctctctctgtggctggcagtttctccaaagggtaacaggtgtcagctggctgagcctaggct
```

-continued

```
gaaccctgagacatgctacctctgtcttctcatggctggaggcagcctttgtaagtcacagaaagtagctgaggg gctctggaaaaaagacagccagggtggaggtagattggtgcatgcagcttctgcagccccgcgtgctagagattt aagcctgattctgcttaacttttccccttgactttggcattttcactttgacatgttccctgagagcctgggggg tggggaaccagctccagctggtgacgtttggggccggcccaggcctagggtgtggaggagccttgccatcgggct tcctgtctctcttcatttaagcacgactctgcag
``` or the minimal proximal CD4 promoter, the murine enhancer and the human silencer.

The invention relates more particularly to the use of T-cell specific lentiviral vectors as defined above, wherein the T-cell specific DNA sequence is inserted between the central polypurine tract and the 3' LTR.

The invention concerns more particularly the use of T-cell specific lentiviral vectors as defined above, such as:

pRRL.sin.PPT.CD4pmE.eGFP.pre deprived of the eGFP coding sequence, corresponding to the following sequence SEQ ID NO:4:

```
AGCTTAATGTAGTCTTATGCAATACTCTTGTAGTCTTGCAACATGGTAACGATGAGTTAGCAACATGCCTTACAA
GGAGAGAAAAAGCACCGTGCATGCCGATTGGTGGAAGTAAGGTGGTACGATCGTGCCTTATTAGGAAGGCAACAG
ACGGGTCTGACATGGATTGGACGAACCACTGAATTGCCGCATTGCAGAGATATTGTATTTAAGTGCCTAGCTCGA
TACAATAAACGGGTCTCTCTGGTTAGACCAGATCTGAGCCTGGGAGCTCTCTGGCTAACTAGGGAACCCACTGCT
TAAGCCTCAATAAAGCTTGCCTTGAGTGCTTCAAGTAGTGTGTGCCCGTCTGTTGTGTGACTCTGGTAACTAGAG
ATCCCTCAGACCCTTTTAGTCAGTGTGGAAAATCTCTAGCAGTGGCGCCCGAACAGGGACCTGAAAGCGAAAGGG
AAACCAGAGCTCTCTCGACGCAGGACTCGGCTTGCTGAAGCGCGCACGGCAAGAGGCGAGGGCGGCGACTGGTG
AGTACGCCAAAAATTTTGACTAGCGGAGGCTAGAAGGAGAGAGATGGGTGCGAGAGCGTCAGTATTAAGCGGGGG
AGAATTAGATCGCGATGGGAAAAAATTCGGTTAAGGCCAGGGGGAAAGAAAAAATATAAATTAAAACATATAGTA
TGGGCAAGCAGGGAGCTAGAACGATTCGCAGTTAATCCTGGCCTGTTAGAAACATCAGAAGGCTGTAGACAAATA
CTGGGACAGCTACAACCATCCCTTCAGACAGGATCAGAAGAACTTAGATCATTATATAATACAGTAGCAACCCTC
TATTGTGTGCATCAAAGGATAGAGATAAAAGACACCAAGGAAGCTTTAGACAAGATAGAGGAAGAGCAAAACAAA
AGTAAGACCACCGCACAGCAAGCGGCCGCTGATCTTCAGACCTGGAGGAGGAGATATGAGGGACAATTGGAGAAG
TGAATTATATAAATATAAAGTAGTAAAAATTGAACCATTAGGAGTAGCACCCACCAAGGCAAAGAGAAGAGTGGT
GCAGAGAGAAAAAGAGCAGTGGGAATAGGAGCTTTGTTCCTTGGGTTCTTGGGAGCAGCAGGAAGCACTATGGG
CGCAGCCTCAATGACGCTGACGGTACAGGCCAGACAATTATTGTCTGGTATAGTGCAGCAGCAGAACAATTTGCT
GAGGGCTATTGAGGCGCAACAGCATCTGTTGCAACTCACAGTCTGGGGCATCAAGCAGCTCCAGGCAAGAATCCT
GGCTGTGGAAAGATACCTAAAGGATCAACAGCTCCTGGGGATTTGGGGTTGCTCTGGAAAACTCATTTGCACCAC
TGCTGTGCCTTGGAATGCTAGTTGGAGTAATAAATCTCTGGAACAGATTTGGAATCACACGACCTGGATGGAGTG
GGACAGAGAAATTAACAATTACACAAGCTTAATACACTCCTTAATTGAAGAATCGCAAAACCAGCAAGAAAAGAA
TGAACAAGAATTATTGGAATTAGATAAATGGGCAAGTTTGTGGAATTGGTTTAACATAACAAATTGGCTGTGGTA
TATAAAATTATTCATAATGATAGTAGGAGGCTTGGTAGGTTTAAGAATAGTTTTTGCTGTACTTTCTATAGTGAA
TAGAGTTAGGCAGGGATATTCACCATTATCGTTTCAGACCCACCTCCCAACCCCGAGGGGACCCGACAGGCCCGA
AGGAATAGAAGAAGAAGGTGGAGAGAGAGACAGAGACAGATCCATTCGATTAGTGAACGGATCTCGACGGTATCG
GTTAACTTTTAAAAGAAAAGGGGGGATTGGGGGGTACAGTGCAGGGGAAAGAATAGTAGACATAATAGCAACAGA
CATACAAACTAAAGAATTACAAAAACAAATTACAAAAATTCAAAATTTTATCGATAAGCTGCATGCTGTTGGGGT
TCAAATTTGAGCCCCAGCTGTTAGCCCTCTGCAAAGAAAAAAAAAAAAAAAAAAGAACAAAGGGCCTAGATTTCC
CTTCTGAGCCCCACCCTAAGATGAAGCCTCTTCTTTCAAGGGAGTGGGGTTGGGGTGGAGGCGGATCCTGTCAGC
TTTGCTCTCTCTGTGGCTGGCAGTTTCTCCAAAGGGTAACAGGTGTCAGCTGGCTGAGCCTAGGCTGAACCCTGA
GACATGCTACCTCTGTCTTCTCATGGCTGGAGGCAGCCTTTGTAAGTCACAGAAAGTAGCTGAGGGGCTCTGGAA
```

-continued

```
AAAAGACAGCCAGGGTGGAGGTAGATTGGTGCATGCAGCTTCTGCAGCCCCGCGTGCTAGAGATTTAAGCCTGAT
TCTGCTTAACTTTTTCCCTTGACTTTGGCATTTTCACTTTGACATGTTCCCTGAGAGCCTGGGGGGTGGGGAACC
AGCTCCAGCTGGTGACGTTTGGGGCCGGCCCAGGCCTAGGGTGTGGAGGAGCCTTGCCATCGGGCTTCCTGTCTC
TCTTCATTTAAGCACGACTCTGCAGGTCGAGATCTAAGTAAGCTTGATATCGAATTCTGCAGTCGACGGTACCGC
GGGCCCGGGATCCACCGGTCGCCACCATGGTGAGCAAGGGCGAGGAGCTGTTCACCGGGGTGGTGCCCATCCTGG
TCGAGCTGGACGGCGACGTAAACGGCCACAAGTTCAGCGTGTCCGGCGAGGGCGAGGGCGATGCCACCTACGGCA
AGCTGACCCTGAAGTTCATCTGCACCACCGGCAAGCTGCCCGTGCCCTGGCCCACCCTCGTGACCACCCTGACCT
ACGGCGTGCAGTGCTTCAGCCGCTACCCCGACCACATGAAGCAGCACGACTTCTTCAAGTCCGCCATGCCCGAAG
GCTACGTCCAGGAGCGCACCATCTTCTTCAAGGACGACGGCAACTACAAGACCCGCGCCGAGGTGAAGTTCGAGG
GCGACACCCTGGTGAACCGCATCGAGCTGAAGGGCATCGACTTCAAGGAGGACGGCAACATCCTGGGGCACAAGC
TGGAGTACAACTACAACAGCCACAACGTCTATATCATGGCCGACAAGCAGAAGAACGGCATCAAGGTGAACTTCA
AGATCCGCCACAACATCGAGGACGGCAGCGTGCAGCTCGCCGACCACTACCAGCAGAACACCCCCATCGGCGACG
GCCCCGTGCTGCTGCCCGACAACCACTACCTGAGCACCCAGTCCGCCCTGAGCAAAGACCCCAACGAGAAGCGCG
ATCACATGGTCCTGCTGGAGTTCGTGACCGCCGCGGGATCACTCTCGGCATGGACGAGCTGTACAAGTAAAGGC
GGCCTCGAGCGACAATCAACCTCTGGATTACAAAATTTGTGAAAGATTGACTGGTATTCTTAACTATGTTGCTCC
TTTTACGCTATGTGGATACGCTGCTTTAATGCCTTTGTATCATGCTATTGCTTCCCGTATGGCTTTCATTTTCTC
CTCCTTGTATAAATCCTGGTTGCTGTCTCTTTATGAGGAGTTGTGGCCCGTTGTCAGGCAACGTGGCGTGGTGTG
CACTGTGTTTGCTGACGCAACCCCCACTGGTTGGGGCATTGCCACCACCTGTCAGCTCCTTTCCGGGACTTTCGC
TTTCCCCCTCCCTATTGCCACGGCGGAACTCATCGCCGCCTGCCTTGCCCGCTGCTGGACAGGGGCTCGGCTGTT
GGGCACTGACAATTCCGTGGTGTTGTCGGGGAAGCTGACGTCCTTTCCATGGCTGCTCGCCTGTGTTGCCACCTG
GATTCTGCGCGGGACGTCCTTCTGCTACGTCCCTTCGGCCCTCAATCCAGCGGACCTTCCTTCCCGCGGCCTGCT
GCCGGCTCTGCGGCCTCTTCCGCGTCTTCGCCTTCGCCCTCAGACGAGTCGGATCTCCCTTTGGGCCGCCTCCCC
GCCTGGAATTCGAGCTCGGTACCTTTAAGACCAATGACTTACAAGGCAGCTGTAGATCTTAGCCACTTTTTAAAA
GAAAAGGGGGGACTGGAAGGGCTAATTCACTCCCAACGAAGACAAGATCTGCTTTTTGCTTGTACTGGGTCTCTC
TGGTTAGACCAGATCTGAGCCTGGGAGCTCTCTGGCTAACTAGGGAACCCACTGCTTAAGCCTCAATAAAGCTTG
CCTTGAGTGCTTCAAGTAGTGTGTGCCCGTCTGTTGTGTGACTCTGGTAACTAGAGATCCCTCAGACCCTTTTAG
TCAGTGTGGAAAATCTCTAG
``` pRRL.sin.PPT.CD4pmE.Sil.eGFP.pre deprived of the eGFP coding sequence, corresponding to the following sequence SEQ ID NO:5:

```
AGCTTAATGTAGTCTTATGCAATACTCTTGTAGTCTTGCAACATGGTAACGATGAGTTAGCAACATGCCTTACAA
GGAGAGAAAAGCACCGTGCATGCCGATTGGTGGAAGTAAGGTGGTACGATCGTGCCTTATTAGGAAGGCAACAG
ACGGGTCTGACATGGATTGGACGAACCACTGAATTGCCGCATTGCAGAGATATTGTATTTAAGTGCCTAGCTCGA
TACAATAAACGGGTCTCTCTGGTTAGACCAGATCTGAGCCTGGGAGCTCTCTGGCTAACTAGGGAACCCACTGCT
TAAGCCTCAATAAAGCTTGCCTTGAGTGCTTCAAGTAGTGTGTGCCCGTCTGTTGTGTGACTCTGGTAACTAGAG
ATCCCTCAGACCCTTTTAGTCAGTGTGGAAAATCTCTAGCAGTGGCGCCCGAACAGGGACCTGAAAGCGAAAGGG
AAACCAGAGCTCTCTCGACGCAGGACTCGGCTTGCTGAAGCGCGCACGGCAAGAGGCGAGGGGCGGCGACTGGTG
AGTACGCCAAAAATTTTGACTAGCGGAGGCTAGAAGGAGAGAGATGGGTGCGAGAGCGTCAGTATTAAGCGGGGG
AGAATTAGATCGCGATGGGAAAAAATTCGGTTAAGGCCAGGGGGAAAGAAAAAATATAAATTAAAACATATAGTA
TGGGCAAGCAGGGAGCTAGAACGATTCGCAGTTAATCCTGGCCTGTTAGAAACATCAGAAGGCTGTAGACAAATA
```

-continued

```
CTGGGACAGCTACAACCATCCCTTCAGACAGGATCAGAAGAACTTAGATCATTATATAATACAGTAGCAACCCTC

TATTGTGTGCATCAAAGGATAGAGATAAAAGACACCAAGGAAGCTTTAGACAAGATAGAGGAAGAGCAAAACAAA

AGTAAGACCACCGCACAGCAAGCGGCCGCTGATCTTCAGACCTGGAGGAGGAGATATGAGGGACAATTGGAGAAG

TGAATTATATAAATATAAAGTAGTAAAAATTGAACCATTAGGAGTAGCACCCACCAAGGCAAAGAGAAGAGTGGT

GCAGAGAGAAAAAAGAGCAGTGGGAATAGGAGCTTTGTTCCTTGGGTTCTTGGGAGCAGCAGGAAGCACTATGGG

CGCAGCCTCAATGACGCTGACGGTACAGGCCAGACAATTATTGTCTGGTATAGTGCAGCAGCAGAACAATTTGCT

GAGGGCTATTGAGGCGCAACAGCATCTGTTGCAACTCACAGTCTGGGGCATCAAGCAGCTCCAGGCAAGAATCCT

GGCTGTGGAAAGATACCTAAAGGATCAACAGCTCCTGGGGATTTGGGGTTGCTCTGGAAAACTCATTTGCACCAC

TGCTGTGCCTTGGAATGCTAGTTGGAGTAATAAATCTCTGGAACAGATTTGGAATCACACGACCTGGATGGAGTG

GGACAGAGAAATTAACAATTACACAAGCTTAATACACTCCTTAATTGAAGAATCGCAAAACCAGCAAGAAAAGAA

TGAACAAGAATTATTGGAATTAGATAAATGGGCAAGTTTGTGGAATTGGTTTAACATAACAAATTGGCTGTGGTA

TATAAAATTATTCATAATGATAGTAGGAGGCTTGGTAGGTTTAAGAATAGTTTTTGCTGTACTTTCTATAGTGAA

TAGAGTTAGGCAGGGATATTCACCATTATCGTTTCAGACCCACCTCCCAACCCCGAGGGGACCCGACAGGCCCGA

AGGAATAGAAGAAGAAGGTGGAGAGAGAGACAGAGACAGATCCATTCGATTAGTGAACGGATCTCGACGGTATCG

GTTAACTTTTAAAGAAAAGGGGGGATTGGGGGGTACAGTGCAGGGGAAAGAATAGTAGACATAATAGCAACAGA

CATACAAACTAAAGAATTACAAAAACAAATTACAAAAATTCAAAATTTTATCGATAAGCTGCATGCTGTTGGGGT

TCAAATTTGAGCCCCAGCTGTTAGCCCTCTGCAAAGAAAAAAAAAAAAAAAAAAAGAACAAAGGGCCTAGATTTCC

CTTCTGAGCCCCACCCTAAGATGAAGCCTCTTCTTTCAAGGGAGTGGGGTTGGGGTGGAGGCGGATCCTGTCAGC

TTTGCTCTCTCTGTGGCTGGCAGTTTCTCCAAAGGGTAACAGGTGTCAGCTGGCTGAGCCTAGGCTGAACCCTGA

GACATGCTACCTCTGTCTTCTCATGGCTGGAGGCAGCCTTTGTAAGTCACAGAAAGTAGCTGAGGGGCTCTGGAA

AAAAGACAGCCAGGGTGGAGGTAGATTGGTGCATGCAGCTTCTGCAGCCCCGCGTGCTAGAGATTTAAGCCTGAT

TCTGCTTAACTTTTTCCCTTGACTTTGGCATTTTCACTTTGACATGTTCCCTGAGAGCCTGGGGGGTGGGAACC

AGCTCCAGCTGGTGACGTTTGGGGCCGGCCCAGGCCTAGGGTGTGGAGGAGCCTTGCCATCGGGCTTCCTGTCTC

TCTTCATTTAAGCACGACTCTGCAGGTCGAGATCTAAGTAAGCTTTTGAGGGGATGAGGGAAGGAGGGTGGGCAC

GGTTCCCCCGATGTGGGTGTCTGAGGCGAAGAAGAGGATGGCGGAGGTTGCAGCCACCAACCACAAGAGTTCCTT

AGAGGGGTCACAGTCTCTAGGAAGTTTATAGGAAGCTAGTCAGCAGTAGAGAGGGTGAACGCGGTGGGGCACATC

CCGCGGCTGGGCTTGAGTGGGCTGCTTGGGGGTTATGGGAGAAGATAAAAGTGCCTGTGGGACCACAGACTCTC

GCTGTGGTGGAGCTGGGCCCTCTTACCCTCCCAAGCCTCGCCCCTCATCCCATCCCTGGGGGCCAGGGGTGAGGG

CGGCAGGAACCTCAAGGCTCTGAGAAAGTGCGTGGTGTGTGTTGCCATTTTGGTCTCTTCTCTTTCTCAGTCTCT

CTTTGCCTCACTTTGGATCTATGCTCTGTGCATCTGTCTTGCTTCTCAGAATTTCTTCTTTTCCTCTTTTTTGT

ACTACCCGGGATCCACCGGTCGCCACCATGGTGAGCAAGGGCGAGGAGCTGTTCACCGGGGTGGTGCCCATCCTG

GTCGAGCTGGACGGCGACGTAAACGGCCACAAGTTCAGCGTGTCCGGCGAGGGCGAGGGCGATGCCACCTACGGC

AAGCTGACCCTGAAGTTCATCTGCACCACCGGCAAGCTGCCCGTGCCCTGGCCCACCCTCGTGACCACCCTGACC

TACGGCGTGCAGTGCTTCAGCCGCTACCCCGACCACATGAAGCAGCACGACTTCTTCAAGTCCGCCATGCCCGAA

GGCTACGTCCAGGAGCGCACCATCTTCTTCAAGGACGACGGCAACTACAAGACCCGCGCCGAGGTGAAGTTCGAG

GGCGACACCCTGGTGAACCGCATCGAGCTGAAGGGCATCGACTTCAAGGAGGACGGCAACATCCTGGGGCACAAG

CTGGAGTACAACTACAACAGCCACAACGTCTATATCATGGCCGACAAGCAGAAGAACGGCATCAAGGTGAACTTC

AAGATCCGCCACAACATCGAGGACGGCAGCGTGCAGCTCGCCGACCACTACCAGCAGAACACCCCCATCGGCGAC

GGCCCCGTGCTGCTGCCCGACAACCACTACCTGAGCACCCAGTCCGCCCTGAGCAAAGACCCCAACGAGAAGCGC

GATCACATGGTCCTGCTGGAGTTCGTGACCGCCGCCGGGATCACTCTCGGCATGGACGAGCTGTACAAGTAAAGC
```

-continued

```
TCGAGCGACAATCAACCTCTGGATTACAAAATTTGTGAAAGATTGACTGGTATTCTTAACTATGTTGCTCCTTTT

ACGCTATGTGGATACGCTGCTTTAATGCCTTTGTATCATGCTATTGCTTCCCGTATGGCTTTCATTTTCTCCTCC

TTGTATAAATCCTGGTTGCTGTCTCTTTATGAGGAGTTGTGGCCCGTTGTCAGGCAACGTGGCGTGGTGTGCACT

GTGTTTGCTGACGCAACCCCCACTGGTTGGGGCATTGCCACCACCTGTCAGCTCCTTTCCGGGACTTTCGCTTTC

CCCCTCCCTATTGCCACGGCGGAACTCATCGCCGCCTGCCTTGCCCGCTGCTGGACAGGGGCTCGGCTGTTGGGC

ACTGACAATTCCGTGGTGTTGTCGGGGAAGCTGACGTCCTTTCCATGGCTGCTCGCCTGTGTTGCCACCTGGATT

CTGCGCGGGACGTCCTTCTGCTACGTCCCTTCGGCCCTCAATCCAGCGGACCTTCCTTCCCGCGGCCTGCTGCCG

GCTCTGCGGCCTCTTCCGCGTCTTCGCCTTCGCCCTCAGACGAGTCGGATCTCCCTTTGGGCCGCCTCCCCGCCT

GGAATTCGAGCTCGGTACCTTTAAGACCAATGACTTACAAGGCAGCTGTAGATCTTAGCCACTTTTTAAAAGAAA

AGGGGGGACTGGAAGGGCTAATTCACTCCCAACGAAGACAAGATCTGCTTTTTGCTTGTACTGGGTCTCTCTGGT

TAGACCAGATCTGAGCCTGGGAGCTCTCTGGCTAACTAGGGAACCCACTGCTTAAGCCTCAATAAAGCTTGCCTT

GAGTGCTTCAAGTAGTGTGTGCCCGTCTGTTGTGTGACTCTGGTAACTAGAGATCCCTCAGACCCTTTTAGT
```

The invention also relates to the use of viral vectors as defined above, for the manufacture of a pharmaceutical composition suitable for an intrathymic administration by injection, and wherein the dosage of said vectors is comprised between $10^5$ and $10^{11}$ infectious particles per milliliter.

The invention also concerns the lentiviral vectors as defiend above, transformed with a predetermined sequence useful for the prevention or treatment of genetic immunodeficiencies, acquired immunodeficiencies, or for the induction of immune tolerance of the organism to self or non-self gene products, cells or tissues, and for the prevention or treatment of autoimmune diseases.

In this respect the invention relates more particularly to lentiviral vectors as defined above, chosen among to the followings:

T-cell specific lentiviral vectors containing a mammalian ZAP-70 coding sequence such as pRRL.sin. cppt.CD4pmE.hZAP-70.IRES.eGFP.pre (SEQ ID NO:2)

Ubiquitous lentiviral vectors containing a viral HA coding sequence such as pRRL.sin. cppt.PGK.HA.pre corresponding to the folowing sequence represented by SEQ ID NO:6:

```
ttaatgtagtcttatgcaatactcttgtagtcttgcaacatggtaacgatgagttagcaacatgccttacaagga gagaaaaagcaccgtgcatgccgattggtggaagtaaggtggtacgatcgtgccttattaggaaggcaacagacg ggtctgacatggattggacgaaccactgaattgccgcattgcagagatattgtatttaagtgcctagctcgatac aataaacgggtctctctggttagaccagatctgagcctgggagctctctggctaactagggaacccactgcttaa gcctcaataaagcttgccttgagtgcttcaagtagtgtgtgcccgtctgttgtgtgactctggtaactagagatc cctcagaccctttagtcagtgtggaaaatctctagcagtggcgcccgaacagggacctgaaagcgaaagggaaa ccagagctctctcgacgcaggactcggcttgctgaagcgcgcacggcaagaggcgaggggcggcgactggtgagt acgccaaaaattttgactagcggaggctagaaggagagagatgggtgcgagagcgtcagtattaagcgggggaga attagatcgcgatgggaaaaaattcggttaaggccaggggggaagaaaaaatataaattaaaacatatagtatgg gcaagcagggagctagaacgattcgcagttaatcctggcctgttagaaacatcagaaggctgtagacaaatactg ggacagctacaaccatcccttcagacaggatcagaagaacttagatcattatataatacagtagcaaccctctat tgtgtgcatcaaaggatagagataaaagacaccaaggaagctttagacaagatagaggaagagcaaaacaaaagt aagaccaccgcacagcaagcggccgctgatcttcagacctggaggaggagatatgagggacaattggagaagtga attatataaatataaagtagtaaaaattgaaccattaggagtagcacccaccaaggcaaagagaagagtggtgca gagagaaaaagagcagtgggaataggagctttgttccttgggttcttgggagcagcaggaagcactatgggcgc agcctcaatgacgctgacggtacaggccagacaattattgtctggtatagtgcagcagcagaacaatttgctgag ggctattgaggcgcaacagcatctgttgcaactcacagtctggggcatcaagcagctccaggcaagaatcctggc tgtggaaagatacctaaaggatcaacagctcctggggatttggggttgctctggaaaactcatttgcaccactgc tgtgccttggaatgctagttggagtaataaatctctggaacagatttggaatcacacgacctggatggagtggga
```

-continued

```
cagagaaattaacaattacacaagcttaatacactccttaattgaagaatcgcaaaaccagcaagaaaagaatga acaagaattattggaattagataaatgggcaagtttgtggaattggtttaacataacaaattggctgtggtatat aaaattattcataatgatagtaggaggcttggtaggtttaagaatagtttttgctgtactttctatagtgaatag agttaggcagggatattcaccattatcgtttcagacccacctcccaaccccgaggggacccgacaggcccgaagg aatagaagaagaaggtggagagagagacagagacagatccattcgattagtgaacggatctcgacggtatcggtt aacttttaaaagaaaaggggggattgggggggtacagtgcaggggaaagaatagtagacataatagcaacagacat acaaactaaagaattacaaaaacaaattacaaaaattcaaaattttatcgatcacgagactagcctcgagaagct tgatatcgaattcccacggggttggggttgcgccttttccaaggcagccctgggtttgcgcagggacgcggctgc tctgggcgtggttccgggaaacgcagcggcgccgaccctgggtctcgcacattcttcacgtccgttcgcagcgtc acccggatcttcgccgctaccttgtgggcccccggcgacgcttcctgctccgcccctaagtcgggaaggttcc ttgcggttcgcggcgtgccggacgtgacaaacggaagccgcacgtctcactagtaccctcgcagacggacagcgc cagggagcaatggcagcgcgccgaccgcgatgggctgtggccaatagcggctgctcagcggggcgcgccgagagc agcggccgggaaggggcggtgcggaggcggggtgtggggcggtagtgtgggccctgttcctgcccgcgcggtgt tccgcattctgcaagcctccggagcgcacgtcggcagtcggctccctcgttgaccgaatcaccgacctctctccc caggggggatccaccggtatgaaggcaaacctactggtcctgttatgtgcacttgcagctgcagatgcagacacaa tatgtataggctaccatgcgaacaattcaaccgacactgttgacacagtactcgagaagaatgtgacagtgacac actctgttaacctgctcgaagacagccacaacggaaaactatgtagattaaaaggaatagccccactacaattgg ggaaatgtaacatcgccggatggctcttgggaaacccagaatgcgacccactgcttccagtgagatcatggtcct acattgtagaaacaccaaactctgagaatggaatatgttatccaggagatttcatcgactatgaggagctgaggg agcaattgagctcagtgtcatcattcgaaagattcgaaatatttcccaaagaaagctcatggcccaaccacaaca caaacggagtaacggcagcatgctcccatgaggggaaaagcagttttttacagaaatttgctatggctgacggaga aggagggctcatacccaaagctgaaaaattcttatgtgaacaaaaagggaaagaagtccttgtactgtggggta ttcatcacccggctaacagtaaggaacaacagaatctctatcagaatgaaaatgcttatgtctctgtagtgactt caaattataacaggagatttaccccggaaatagcagaaagacccaaagtaagagatcaagctgggaggatgaact attactggaccttgctaaaacccggagacacaataatatttgaggcaaatggaaatctaatagcaccaatgtatg ctttcgcactgagtagaggctttgggtccggcatcatcacctcaaacgcatcaatgcatgagtgtaacacgaagt gtcaaacacccctgggagctataaacagcagtctcccttaccagaatatacacccagtcacaataggagagtgcc caaaatacgtcaggagtgccaaattgaggatggttacaggactaaggaacattccgtccattcaatccagaggcc tatttggagccattgccggttttattgaaggggggatggactggaatgatagatggatggtatggttatcatcatc agaatgaacagggatcaggctatgcagcggatcaaaaaagcacacaaaatgccattaacgggattacaaacaagg tgaacactgttatcgagaaaatgaacattcaattcacagctgtgggtaaagaattcaacaaattagaaaaaagga tggaaaatttaaataaaaagttgatgatggatttctggacatttggacatataatgcagaattgttagttctac tggaaaatgaaaggactctggatttccatgactcaaatgtgaagaatctgtatgagaaagtaaaaagccaattaa agaataatgccaaagaaatcggaaatggatgttttgagttctaccacaagtgtgacaatgaatgcatggaaagtg taagaaatgggacttatgattatcccaaatattcagaagagtcaaagttgaacagggaaaaggtagatggagtga aattggaatcaatggggatctatcagattctggcgatctactcaactgtcgccagttcactgtgagtcgacaatc aacctctggattacaaaatttgtgaaagattgactggtattcttaactatgttgctccttttacgctatgtggat acgctgctttaatgcctttgtatcatgctattgcttcccgtatggctttcattttctcctccttgtataaatcct ggttgctgtctctttatgaggagttgtggcccgttgtcaggcaacgtggcgtggtgtgcactgtgtttgctgacg caaccccactggtggggcattgccaccacctgtcagctccttccgggactttcgctttcccccctccctattg ccacggcggaactcatcgccgcctgccttgcccgctgctggacaggggctcggctgttgggcactgacaattccg
```

-continued

```
tggtgttgtcggggaagctgacgtcctttccatggctgctcgcctgtgttgccacctggattctgcgcgggacgt ccttctgctacgtcccttcggccctcaatccagcggaccttccttcccgcggcctgctgccggctctgcggcctc ttccgcgtcttcgccttcgccctcagacgagtcggatctccctttgggccgcctccccgcctggaattcgagctc ggtacctttaagaccaatgacttacaaggcagctgtagatcttagccacttttaaaagaaaagggggactgga agggctaattcactcccaacgaagacaagatctgcttttgcttgtactgggtctctctggttagaccagatctg agcctgggagctctctggctaactagggaacccactgcttaagcctcaataaagcttgccttgagtgcttcaagt agtgtgtgcccgtctgttgtgtgactctggtaactagagatccctcagacccttttagtcagtgtggaaaatctc tagca
```

Ubiquitous lentiviral vectors containing a mammalian Insulin coding sequence such as pRRL.sin.cppt.PGK.Ins2.GTX.eGFP.pre (SEQ ID NO:1).

The invention relates to the transformed thymic stromal cells characterized in that they contain viral vectors containing a predetermined recombinant nucleotide sequence for the induction of immune tolerance of the organism to self or non-self gene products, cells or tissues, or for the prevention or treatment of autoimmune diseases, genetic immunodeficiencies, acquired immunodeficiencies, such as lentiviral vectors as defined above, stably integrated in their genome.

The invention also concerns the transformed Cells of the T-cell lineage, characterized in that they contain viral vectors containing a predetermined recombinant nucleotide sequence for the induction of immune tolerance of the organism to self or non-self gene products, cells or tissues, or for the prevention or treatment of autoimmune diseases, genetic immunodeficiencies, acquired immunodeficiencies, such as lentiviral vectors as defined above, stably integrated in their genome.

The invention relates to pharmaceutical compositions comprising lentiviral vectors as defined above, or transformed cells as mentioned above, in association with a suitable pharmaceutical carrier.

The invention relates more particularly to pharmaceutical compositions as defined above, suitable for an intrathymic administration by injection.

The invention concerns more particularly the pharmaceutical compositions as defined above, wherein the dosage of said lentiviral vectors is comprised between $10^5$ and $10^{11}$ infectious particles per milliliter.

DETAILED DESCRIPTION OF THE INVENTION

The invention also relates to gene therapy methods comprising the administration, via intrathymic route, of viral vectors as defined above containing a predetermined recombinant nucleotide sequence under the control of elements directing its expression in eukaryotic cells, to a patient in need thereof, in the frame of the prevention or treatment of genetic immunodeficiencies, acquired immunodeficiencies, or for the induction of immune tolerance of the organism to self or non-self gene products, cells or tissues, or for the prevention or treatment of autoimmune diseases, as mentioned above.

Total thymocytes were stained with anti-CD4, anti-CD8 and anti-CD3 monoclonal antibodies. Upper panels: saline-injected control mice (CTRL) and LvPGK-GFP-injected mice at two different time points after injection (D5 and D30) are shown. Lower panels: The profile of CD4/CD8 expression is shown within gated eGFP$^+$ cells.

Figure 11:
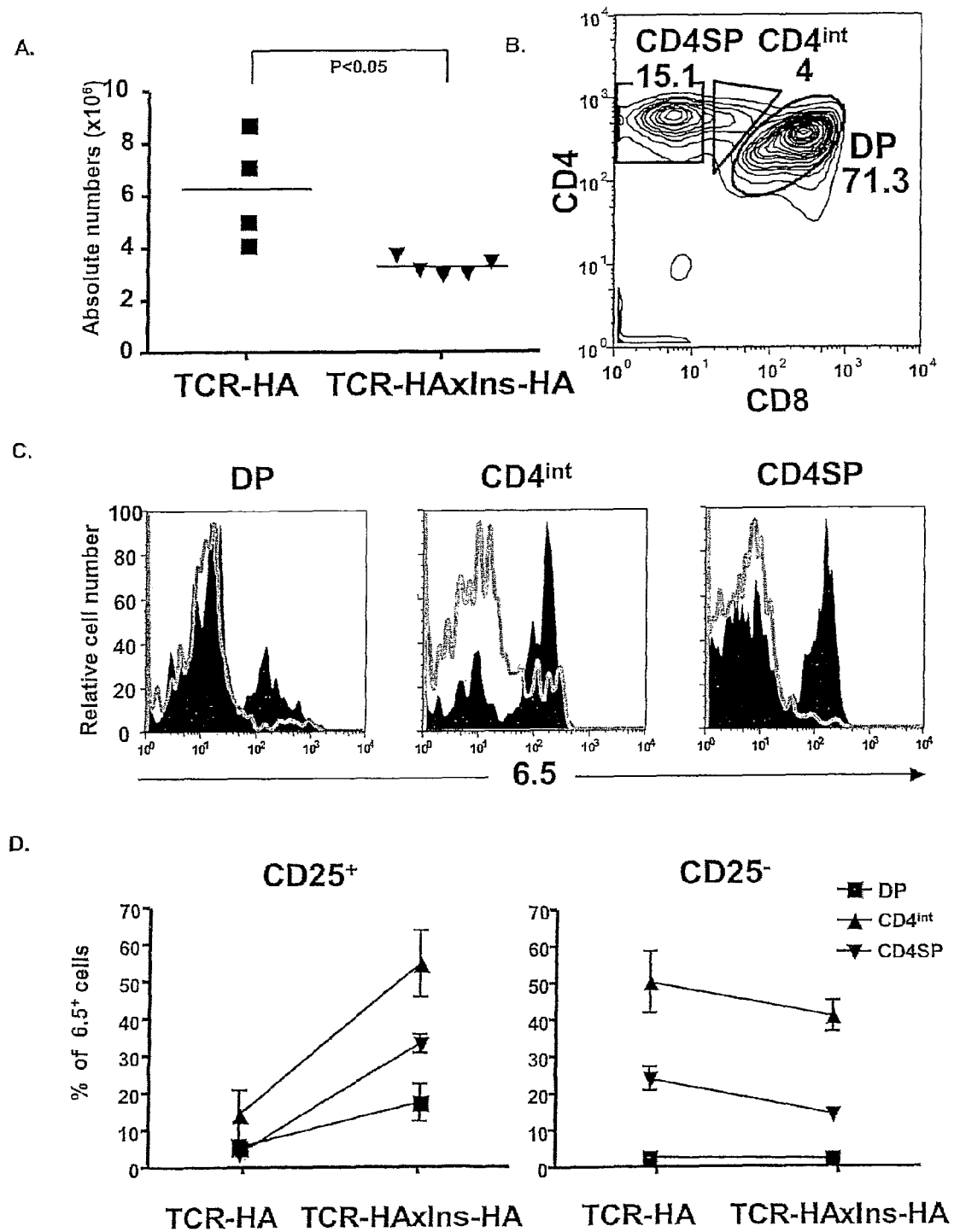

FIG. 11. HA-specific thymocyte differentiation in TCR-HA and TCR-HAxIns-HA transgenic mice. (A) Absolute numbers of HA-specific (6.5$^+$) cells in the thymus of fourteen-week-old TCR-HA (v) and TCR-HAxIns-HA (τ) transgenic mice. Each dot represents a single mouse. The two mean values are statistically different (p<0.05). (B) Gating of thymocyte subsets based on CD4 and CD8 expression in TCR-HA transgenic mice. Indicated are the frequencies of the respective population in percentages of total thymocytes. (C) Overlaid expression of the transgenic TCR (6.5$^+$) in CD25$^+$ cells of the indicated phenotypes in the thymus of TCR-HA (gray lines) and TCR-HAxIns-HA (solid lines) transgenic mice. (D) Frequencies (percentages±SD) of 6.5$^+$ cells in CD25$^+$ and CD25$^-$ cells within subsets defined in 1B (DP=CD4$^+$CD8$^+$; CD4$^{int}$=CD4$^{+CD}$8$^{lo}$; CD4SP=CD4$^+$CD8$^-$ cells).

Figure 12:
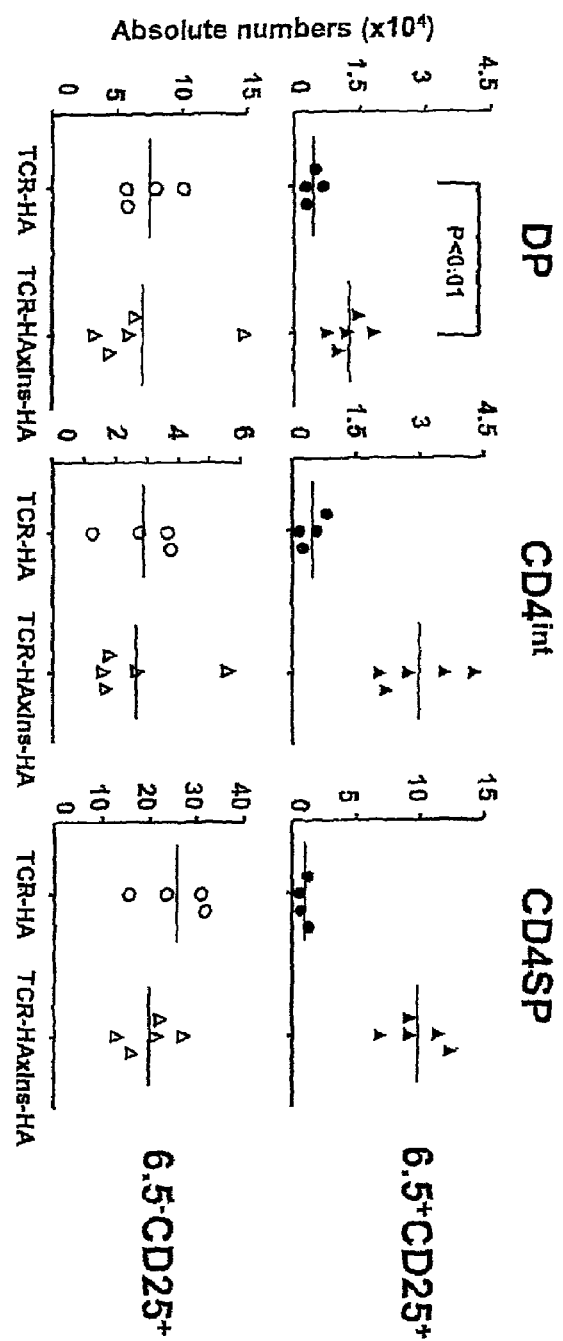

FIG. 12. Absolute numbers of CD25$^+$ cells in thymocyte subsets of TCR-HA and TCR-HAxIns-HA transgenic mice. Upper panels: absolute numbers of 6.5$^+$CD25$^+$ cells in TCR-HA (λ) and TCR-HAxIns-HA (σ) transgenic mice for the indicated subset. Lower panels: absolute numbers of 6.5$^-$CD25$^+$ cells in TCR-HA (μ) and TCR-HAxIns-HA (Δ) transgenic mice for the indicated subset.

Figure 13:
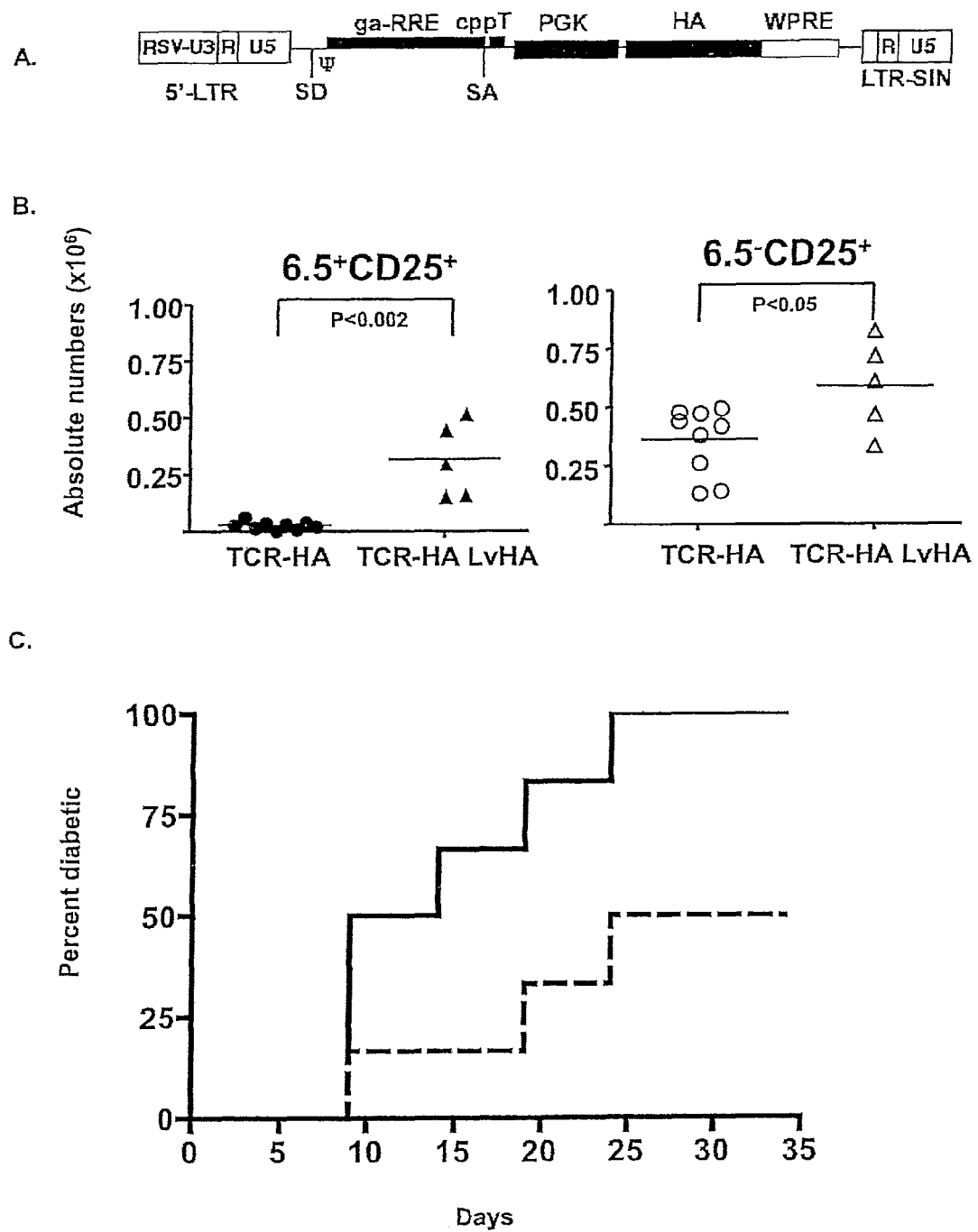

FIG. 13. De novo generation of regulatory T cells upon intrathymic injection of HA-encoding lentiviral vector in TCR-HA transgenic mice. (A) Schematic representation of the HA-encoding lentiviral vector. (B) Absolute numbers of 6.5$^+$CD25$^+$ (closed symbols) and 6.5$^-$CD25$^+$ (open symbols) CD4SP thymocytes in TCR-HA transgenic mice injected with GFP-expressing (TCR-HA) or HA-encoding lentiviral vectors (TCR-HA LvHA) (C) Percentages of diabetic Ins-HA mice upon co-transfer of purified CD25$^+$ peripheral T cells from TCR-HA transgenic mice injected in the thymus with GFP-expressing (solid line) or HA-expressing (dashed line) lentiviral vectors 10-days earlier.

Figure 14:
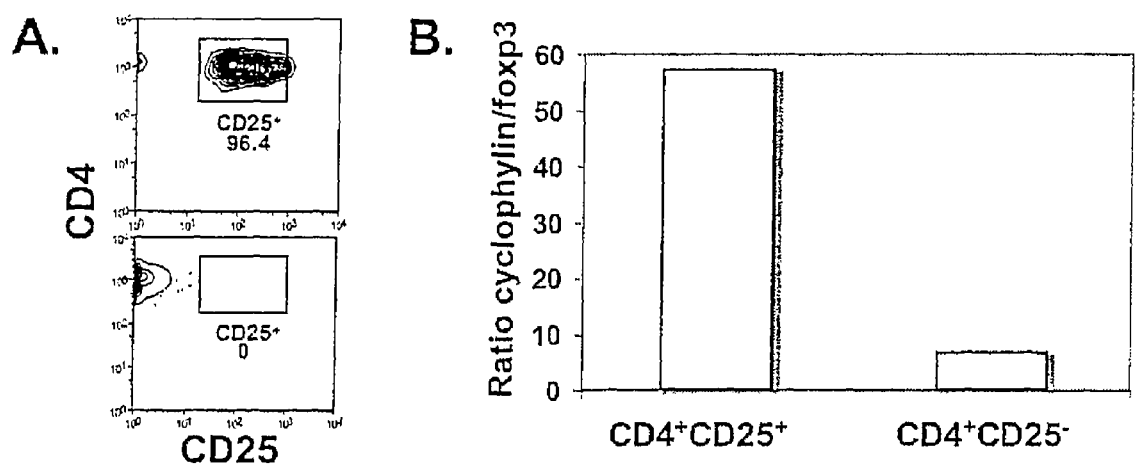

FIG. 14. Semi-quantitative assessment of foxp3 mRNA in sorted CD4$^+$CD25$^+$ and CD4$^+$CD25$^-$ thymocyte from a TCR-HaxIns-HA mouse. (A) Purity of sorted CD4$^+$CD25$^+$ (upper panel) and CD4$^+$CD25$^-$ thymocyte (lower panel) after cell sorting. (B) Optical densities of the PCR bands were measured using the Image software (NIH) in the indicated thymocyte subset. Ratio of housekeeping cyclophylin mRNA over foxp3 mRNA in these arbitary units is represented.

DETAILED DESCRIPTION OF THE INVENTION

The present invention will be further illustrated by the following examples of transformation of thymic stromal cells, or of intrathymic lymphocytes or lymphocytes precursors, with vectors of the invention as described above.

I) In Vivo Correction of ZAP-70 Immunodeficiency by Intrathymic Gene Transfer

1) Abstract

Severe combined immunodeficiency (SCID) patients have been successfully treated by administration of ex vivo gene-corrected stem cells. However, despite its proven efficacy, such a treatment carries specific risks and difficulties. The inventors hypothesized that some of these drawbacks may be overcome by in situ gene correction of T lymphoid progenitors in the thymus. Indeed, in vivo intrathymic transfer of a gene providing a selective advantage for transduced prothymocytes should result in the generation of functional T lymphocyte progeny allowing long-term immune reconstitution. The inventors assessed the feasibility of this approach in a murine model of ZAP-70-deficient SCID. A T cell-specific ZAP-70-expressing lentiviral vector was injected into thymi of adult ZAP-70$^{-/-}$ mice, without prior conditioning. This resulted in the long-term differentiation of mature TCRαβ+ thymocytes, indicating that the vector had integrated into progenitor cells. Moreover, peripheral ZAP-70-expressing T cells demonstrated a partially diversified receptor repertoire and were responsive to allo-antigens in vitro and in vivo. Improved treatment efficacy was achieved in infant ZAP-70$^{-/-}$ mice where the thymus is larger and a higher percentage of prothymocytes are in cycle. Thus, intrathymic injection of a lentiviral vector represents a simplified and potentially safer alternative to ex-vivo gene-modified hematopoietic stem cell transplantation for gene therapy of T cell inmmodeficiencies.

The abbreviations used hereafter are the followings: adenosine deaminase, ADA; bone marrow transplantation, BMT; human leukocyte antigen, HLA; hematopoietic stem cell, HSC; Intrathymic, IT; Murine Leukemia Virus, MLV; severe combined immunodeficiency, SCID; transducing units, TU; wild type, WT.

2) Introduction

Severe combined immunodeficiency (SCID) is a heterogeneous group of genetic disorders that is almost universally fatal in infancy, due to the advent of opportunistic infections. SCID can be treated by allogeneic stem cell transplantation, but the majority of patients do not have histocompatible donors. In the absence of histocompatible donors, SCID patients sometimes receive an HSC transplant from HLA-haploidentical donors. Although recent modifications of this protocol have increased survival to levels approaching 75%, there are significant short-term and long-term complications and the emergence of significant numbers of circulating naïve T cells often requires more than 150 days (1-3). Alternatively, SCID represents a unique favorable setting for gene therapies strategies as the gene-corrected lymphocytes should have a selective advantage. Indeed, such an approach has already been shown to be beneficial in several ADA-deficient and γc-deficient SCID patients (4-7). The extensive ability of T progenitors to undergo massive expansion translates into the possibility that only a few corrected progenitor cells can reconstitute the T cell compartment, as highlighted by <<experiments of nature>>. Specifically, several individuals with inherited mutations that are known to result in SCID (X-SCID and ADA-deficiency) have been found to be relatively healthy, with relatively normal T cell numbers (8-11). In each of these patients, this was likely due to a reversion mutation in a single hematopoietic progenitor/stem cell as such an event is statistically improbable (8-10). These <<natural gene therapy experiments>> strongly suggest that gene correction of a single progenitor cell, if capable of proliferation, differentiation, and migration, can potentially eliminate the critical symptoms associated with SCID.

Based on these premises, clinical gene therapy trials for SCID disorders have thus far relied on ex vivo gene transfer into hematopoietic stem (HSC)/progenitor cells (CD34+) using non-specific retroviral vectors. Despite its proven efficacy (4, 6, 7, 12, 13), such an approach carries specific risks and difficulties (14). First, as gene transfer with murine leukemia virus (MLV)-based retroviral vectors cannot occur in the absence of mitosis, this approach requires the ex vivo culture of CD34+ cells in the presence of a cocktail of cytokines. This is a cumbersome manipulation that can affect the long-term functionality of these cells. Second, the ectopic expression of the therapeutic gene in all stem cell progeny could generate serious side effects, notably when the transgene participates in signal transduction pathways. Finally, oncoretroviral insertion per se, by modifying the expression of cellular genes, can participate to leukemogenesis (14, 15).

The inventors hypothesized that some of these drawbacks could be overcome by in situ gene correction of T lymphoid progenitors in the thymus using T cell-specific lentiviral vectors. This hypothesis was supported by the following observations: (i) Lentiviral vectors have resulted in efficient in vivo gene transfer in hepatocytes, antigen-presenting cells, muscle cells, as well as cells in the central nervous system (16-21); (ii) Early T lymphoid progenitors (ETP) in the thymus appear to sustain production of T lineage progeny for longer periods of time than the common lymphoid progenitors (CLP) found in the BM (23). Thus, the inventors reasoned that IT injection of a T cell-specific lentiviral vector encoding a gene that provides a selective advantage for transduced prothymocytes might result in the generation of functional T lymphocyte progeny with subsequent long-term immune reconstitution.

The feasibility of this approach was assessed in a murine model of ZAP-70 deficiency. ZAP-70 is a 70Kd protein tyrosine kinase (PTK) that is recruited to the T cell receptor (TCR) following its stimulation (24). It is expressed at approximately equivalent levels in thymocytes, mature T cells and NK cells (25). Its absence results in a SCID phenotype with a block in T cell development, at the CD4+CD8+ thymocyte stage (26-28). To obviate the potential obstacles/risks concerning ubiquitous expression of ZAP-70, the wt gene was introduced into a T cell-specific lentiviral vector (29). Here, the inventors demonstrate that direct intrathymic injection of this ZAP-70-expressing lentiviral vector results in the reconstitution of polyclonal and functional T cells.

Figure 1:
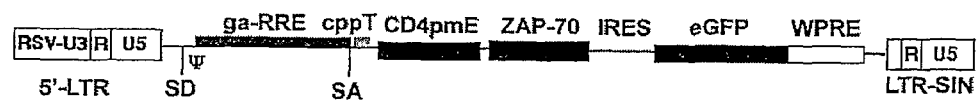
FIG. 1. Schematic representation of the pCD4 lentiviral vector encoding wild-type ZAP-70.

3) Results a) Thymocyte development in mice intrathymically injected with a ZAP-70-expressing lentiviral vector In an attempt to reconstitute T lineage cells via in situ gene transfer, the inventors injected a T cell-specific lentiviral vector encoding human ZAP-70 (pT-ZAP) directly into the thymi of 8-12 week old ZAP-70-deficient mice. In pT-ZAP, the ZAP-70/IRES/eGFP cassette is under the transcriptional control of T-cell specific regulatory sequences derived from the CD4 gene (FIG. 1). In the context of this lentiviral vector, ZAP-70 and eGFP expression are concordant (FIG. 1). Following thoracic surgery, the inventors intrathymically injected (IT) 10-20 µl of vector preparations containing 2-4× $10^7$ transducing units (TU) of pT-ZAP. It is notable that this translates into a very low overall multiplicity of infection (MOI<0.1), as determined by the ratio of infectious particles to the total overall number of thymocytes and stromal cells in the thymus. Furthermore, since the inventors shown hereafter that IT injections lead to a preferential infection of thymic stromal cells, the MOI for thymocytes is even lower.

The absence of ZAP-70 is associated with a relatively late block in T cell differentiation, at the CD4+CD8+ DP thymocyte stage (26-28) (FIG. 2a). As expected from the very low MOI used, the actual percentage of transduced thymocytes was extremely low (0.3%, FIG. 2b) and thus IT injections of pT-ZAP were not expected to dramatically alter the overall percentage of SP thymocytes as compared to the deficient animals (FIG. 2a). However, while TCRβ upregulation is blocked in ZAP-70 deficient mice, the IT-injected mice demonstrated a significant increase in TCRβ+ CD4 SP thymocytes. Moreover, analysis of eGFP+TCRβ+ cells showed that percentages of mature CD4 and CD8 single positive thymocytes were similar to that detected in wild type mice, representing greater than 80% of cells (FIG. 2b). In marked contrast, the phenotype of thymocytes within the eGFP-TCRβ+ population of pT-ZAP-injected mice, was largely immature DP cells (71%, FIG. 2b). These results indicate that ZAP-70 expression driven from pT-ZAP is capable of correcting the differentiation block in ZAP-70 deficiency.

Figure 2:
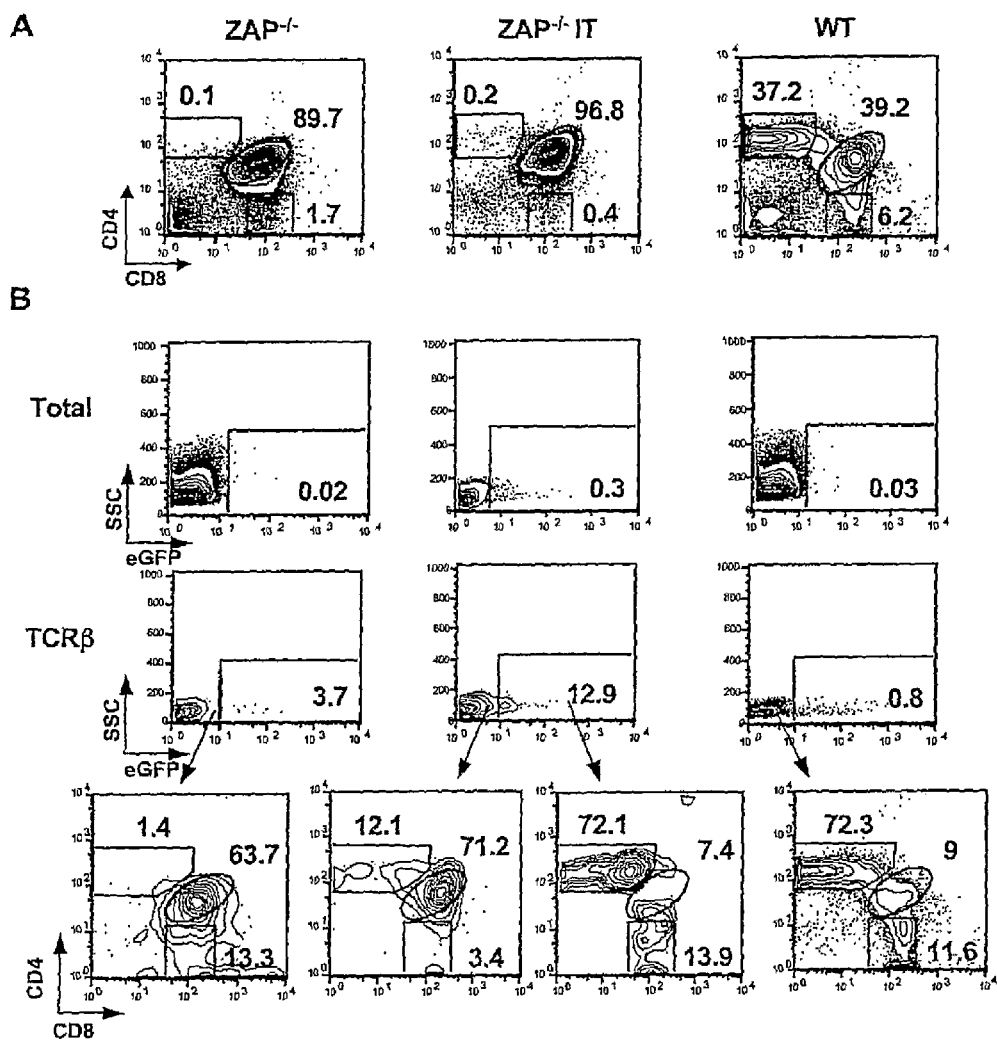
FIG. 2. Thymocyte differentiation in ZAP-70 mice following in situ injection of a ZAP-70-expressing lentiviral vector. (A) Total thymocytes were stained with Cy-conjugated αCD8 and APC-conjugated αCD4mAbs. (B) The percentages of eGFP+ cells within the entire thymus as well as within the thymocyte subset wherein TCRβ was upregulated are shown.
Figure 3:
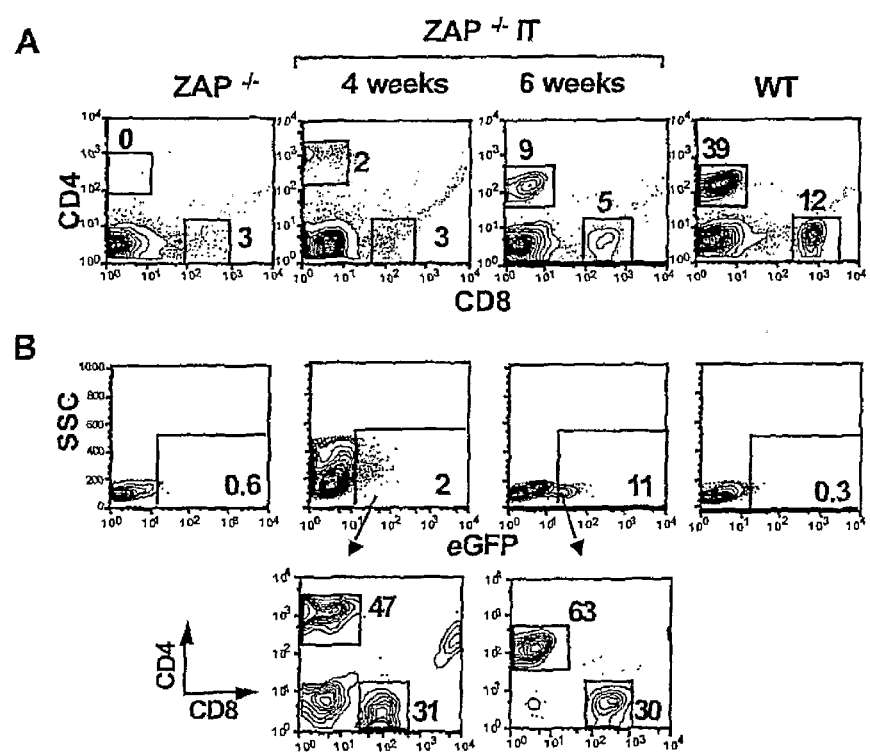
FIG. 3. Kinetics of peripheral T lymphocyte emigration following in situ thymic injection of a ZAP-70-expressing lentiviral vector. (A) The overall percentage of CD4+ and CD8+ T cells within the peripheral blood at these time points is indicated. (B) The percentages of eGFP+ cells in the peripheral blood of all animals are shown.

As differentiating thymocytes have a limited life span, i.e. DN cells can differentiate and migrate across the cortex in 15 days (30), the detection of transduced thymocytes at 7-52 weeks post-gene transfer strongly suggests that the ZAP-70 lentiviral vector was successfully integrated into progenitor cells (FIG. 2b). Notably, this modulation in thymocyte differentiation was not due to a non-specific effect of the injected virions as: i) mature thymocytes were not detected 14 weeks post injection of a control eGFP lentiviral vector (FIG. 2) and ii) neither injection of eGFP nor ZAP-70 lentiviral vectors, at the dose utilized here, modulated thymocyte differentiation immediately (72 hours) following IT injection (FIG. 3).

b) T cell development in mice intrathymically injected with a ZAP-70-expressing lentiviral vector To determine whether in vivo gene transfer in the thymus results in the appearance of mature T cells in the periphery, peripheral blood samples were analyzed for the presence of CD3+ lymphocytes, starting at 4 weeks post-thymic injection (FIG. 3a). The inventors could indeed detect such cells in $6/26$ treated adult mice. The percentage of CD3+ peripheral blood lymphocytes at 4 weeks reached 4-5%, similar to what the inventors previously observed following transplantation of wild type progenitor cells or ZAP-70$^{-/-}$ progenitor cells transduced with a ZAP-70-expressing retroviral vector (31). Notably, in reconstituted mice, the percentage of peripheral blood CD3+ lymphocytes increased with time, with 15% CD4+ or CD8+ T lymphocytes in the peripheral blood at 6 weeks (FIG. 3a). These levels are nonetheless significantly lower than that detected in WT mice. As shown in FIG. 3b, the vast majority of cells within the eGFP+ compartment were of the CD4+ or CD8+ T cell phenotype. The increment in T cell numbers continued in the intrathymically injected mice with higher percentages of T lymphocytes detected in the lymph nodes and spleen at 8 weeks post IT injection (FIG. 4a). Altogether, these data demonstrate that a correction in ZAP-70 expression by IT gene transfer results in the presence of mature T cells in the periphery.

The activation status of these T lymphocytes was determined by assessing the expression of the CD25 and CD69 activation markers. T cells from ZAP-70$^{-/-}$ mice intrathymically injected with pT-ZAP expressed the CD25 activation marker at significantly higher proportion of cells than that observed in WT mice (44±11.7% (n=5) vs. 22±4.6% (n=5), p=0.001; FIG. 4b). Expression of the CD69 activation marker was also elevated in ZAP-70-transduced T cells as compared to T cells in WT mice, indicative of T-cell activation. While both naïve and "memory phenotype" (32) T cell populations were observed in reconstituted mice, the percentage of naïve T cells (CD62L$^+$) was lower in mice intrathymically injected with pT-ZAP (FIG. 4b). Indeed, the overall percentage of peripheral T cells detected in pT-ZAP-injected mice was always lower than that observed in WT animals (Table 1). CD3+ lymph node T cells in the pT-ZAP-injected mice reached 26% whereas those in WT mice averaged approximately 60% (Table 1). Of note, the level of eGFP expression in the CD3+ T cells varied widely, from 14-66%. As T cell levels in ZAP-70$^{-/-}$ mice generally do not exceed 4%, it is extremely likely that the vast majority of T cells detected in the pT-ZAP-injected mice differentiated due to the presence of the ZAP-70 transgene. Thus, the inability to detect eGFP in all T cells is either due to some discordance between ZAP-70 and eGFP expression in vivo in the context of the upstream IRES (FIG. 1, Table 1) or to low downregulated levels of eGFP not detected by FACS.

c) ZAP-70 expression and diversity of T cells developing in mice intrathymically injected with a ZAP-70-expressing lentiviral vector.

Figure 5:
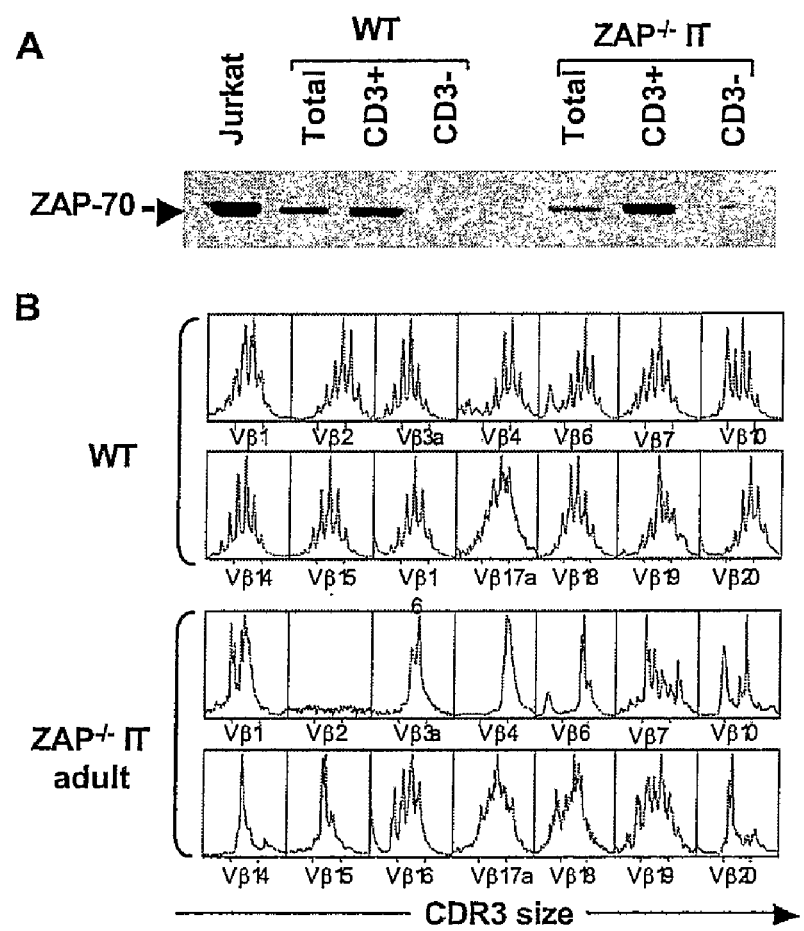
FIG. 5. ZAP-70 expression and diversity in T lymphocytes reconstituted by intrathymic injection of the pT-ZAP lentiviral vector. (A) ZAP-70 levels in total splenocytes from WT and IT-reconstituted ZAP-70 mice as well as in sorted CD3+ and CD3− populations were assessed in western blots using an αZAP-70 mAb. (B) The TCRBV repertoire was assessed by a comparison of T cell receptor CDR3 size distribution (Immunoscope profiles) of lymph node cells obtained from WT and IT-reconstituted adult ZAP-70$^{-/-}$ mice.

The inventors next assessed the level of ZAP-70 expressed in peripheral T lymphocytes, as well as the diversity of their TCR repertoire (FIG. 5). Levels of lentiviral-encoded ZAP-70 were similar to that of the endogenous protein in WT mice. The ectopic expression of the ZAP-70 transgene was further studied by sorting CD3+ cells and CD3– cells from wild type mice and ZAP-70$^{-/-}$ mice reconstituted by intrathymic injection of pT-ZAP. Importantly, ectopic ZAP-70 expression was detected almost exclusively in the CD3+ T cell compartment following its expression from the pT-ZAP lentiviral vector (FIG. 5a). Thus, the CD4 promoter appears to drive expression of ZAP-70 in T cells to levels similar to that of the endogenous promoter.

The inventors then investigated the relative usage of each T cell receptor β chain hypervariable region (TCRBV) within the global T cell population by flow cytometry and the immunoscope/spectratype method (33, 34). Using a combination of these two methods, The inventors established both the frequencies of BV-expressing cells and their repertoire diversity. The Immunoscope method is based on an RT-PCR of the hypervariable complementarity determining region 3 (CDR3), allowing the lengths of the mRNA encoding each β chain of the TCR to be analyzed. In a normal setting, each single peak is composed of multiple differently rearranged sequences. A Gaussian distribution of the CDR3 lengths is thus indicative of an extremely diverse and non-biased T cell population.

The CDR3 length profiles of T cells from the ZAP-70-IT reconstituted mice had a Gaussian distribution for an average of 26% of the 14 BV families analyzed (with a range of 0 to 75%), with the remaining BV families appearing mono or oliogoclonal. This is in contrast with WT mice where a Gaussian distribution was found for all the TCRBV families analyzed (FIG. 5b). Flow cytometry analyses of TCRBV expression in 6 reconstituted mice also showed a diverse although not normal repertoire in both CD4 and CD8 T cell populations, with BV representation varying for each ZAP-70-IT reconstituted mice. The inventors found that on average, 60% of the 11 BV families analyzed were detected by flow cytometry (with a range of 30 to 100%) and 77% by the Immunoscope method (with a range of 50 to 100%). This difference is likely due to the higher sensitivity of the Immunoscope method as compared to flow cytometry. The results thus show that the T-cell repertoire of pT-ZAP-injected mice was fairly diverse in terms of BV usage, but was perturbed with respect to both frequencies and clonality.

d) Function of T cells developing in mice intrathymically injected with a ZAP-70-expressing lentiviral vector.

The functionality of the T lymphocytes that developed in IT-injected ZAP-70$^{-/-}$ mice were assessed in several manners, including by their ability to respond to ex vivo T cell receptor stimulation (FIG. 6a). Notably, ZAP-70 plays a critical role in the activation of mature T lymphocytes. In the absence of the WT protein, early as well as late biological responses, such as proliferation, are defective (35). In the absence of stimulation, neither WT nor pT-ZAP transduced T cells significantly proliferated, showing that ectopic expression of ZAP-70 did not modulate the basal proliferative status of corrected T cells. Following a 3 day stimulation with either concanavalin A or α-CD3/IL-2, a significant percentage of both WT and pT-ZAP transduced T cells had undergone up to 4 divisions. In contrast, no division was induced in splenocytes isolated from control ZAP-70-deficient mice. Thus, pT-ZAP-transduced T cells, like WT T cells, are capable of responding to a TCR-specific stimulus.

To assess whether these pT-ZAP-transduced T cells were capable of responding to an immune stimulation in vivo, mice were grafted with both syngeneic (C57BL/6) and fully mismatched allogeneic (BALB/c) skin grafts on the two sides of the back. Control mice included untreated ZAP-70-deficient mice (n=3) and wild type C57BL/6 mice (n=2), transplanted with the same skin grafts. As expected, the untreated ZAP-70-deficient mice, who do not develop T cells, rejected neither the sygeneic nor the allogeneic grafts. In the control C57BL/6 mice, allograft rejection was acute, with signs of necrosis appearing from day 12 onward while syngeneic grafts were maintained. In the pT-ZAP-injected mice, signs of rejection were observed in two of the three mice between days 21 and 30. Importantly, the two mice who presented with erythema and thickening of the allogeneic graft had higher percentages of CD3+ peripheral T cells (16% and 19% splenic T cells, respectively) than the mouse without evidence of rejection (7%). To more precisely analyze the grafts, they were biopsied between days 30-40 and histological analyses were performed on paraffin sections. In the syngeneic and allogeneic sections transplanted on the pT-ZAP-injected mice, there was evidence of fibroblast hyperplasia. However, only in allogeneic sections was lymphocyte infiltration prevalent in the superficial dermis and epidermal layers (in the 2 of 3 mice with clinical evidence of rejection, FIG. 6b). Moreover, the T lymphocytes from the IT-injected mice proliferated in response to these allo-antigens, as observed in a mixed lymphocyte reaction. Lymph node T cells from wild type (C57BL/6) and skin-grafted pT-ZAP-reconstituted mice proliferated in response to allogeneic BALB/c antigens (FIG. 6c). Thus, allogeneic immune stimulation of pT-ZAP-transduced T cells was induced by the presence of a mismatched skin graft.

e) T cell reconstitution efficiency is significantly enhanced upon intrathymic injection of a ZAP-70-expressing lentiviral vector into infant mice The ensemble of the data presented above demonstrates that intrathymic injection of a lentiviral vector encoding ZAP-70 can result in the restoration of T cell differentiation in the thymus and periphery of ZAP-70-deficient mice. Nevertheless, the inventors were only able to detect significant T cell reconstitution in 6 of 26 adult ZAP-70$^{-/-}$ mice intrathymically injected with the pT-ZAP vector (23%). The inventors believe that this relatively low efficacy is in large part due to (i) technical issues related to injection of the virion suspension into the small thymus of adult mice and (ii) the low MOI used. Moreover, insufficient ZAP-70 transgene expression in the thymus, and/or an insufficient population of thymocyte progenitors that are susceptible to lentiviral transduction may also play a role.

To attempt to circumvent these problems, the inventors injected the pT-ZAP lentiviral vector into the thymi of young mice (10-14 days). As in human infants, the thymi of ZAP-70-deficient infant mice is significantly larger than that of adults. Moreover, the inventors found that a higher percentage of prothymocytes in the thymi of ZAP-70-deficient infants were "blast-like" as assessed by their FSC/SSC profiles and in cycle (Ki-67+), as compared to their adult counterparts (FIG. 7a). As the inventors and others have shown that cycling T cells are significantly more susceptible to lentiviral transduction than the quiescent population (36), prothymocytes of young mice would also be expected to be more susceptible to gene transfer. In line with this hypothesis, the inventors found that a higher percentage of the Ki-67$^+$ thymocytes in infants were of an immature DN phenotype (25% vs. 14%, FIG. 7b).

Since performing thoracic surgery on 10-14 day old mice is technically challenging, the inventors developed a "blind" approach whereby the virion suspension was injected directly through the skin into the thoracic cavity immediately above the sternum. This approach resulted in appropriately targeted intrathymic injection, as assessed using injected dyes (unpublished observations). Following intrathymic injection of pT-ZAP into these infant thymi, T cell reconstitution was detected in 75% of injected animals (15 of 20), with percentages of CD3+ T cells in lymph nodes and spleens similar to that observed in successfully treated adult mice (FIG. 5C and Table 1). Thus, direct in vivo injection of the ZAP-70-expressing lentiviral vector into infant thymi results in a significantly improved success rate of T cell reconstitution.

4) Discussion

Figure 4:
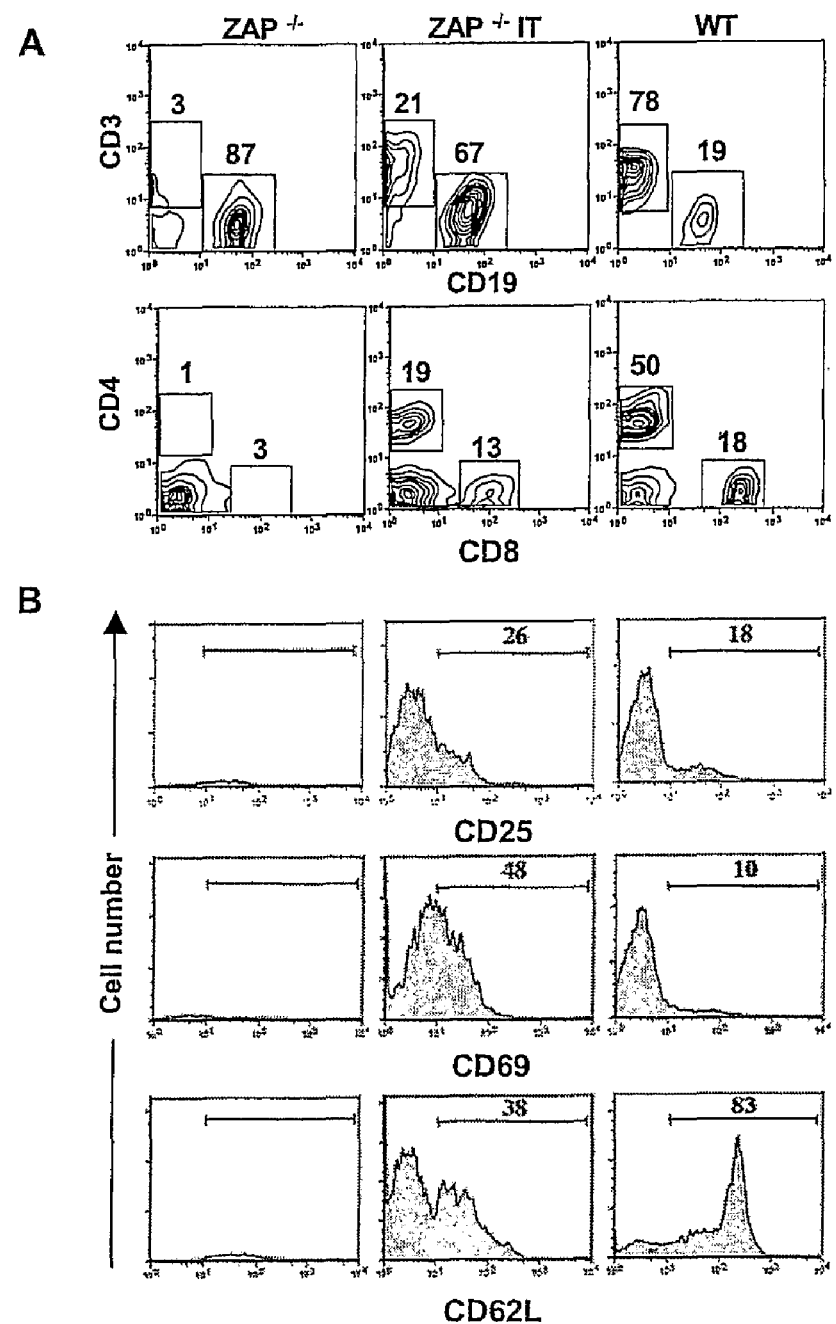
FIG. 4. T lymphocyte reconstitution in ZAP-70$^{-/-}$ mice following in situ injection of a ZAP-70-expressing lentiviral vector. (A) The percentages of CD4, CD8, CD3 and CD19 cells are indicated. (B) The activation status of the T cell population was determined.

Altogether, these data demonstrate that direct injection of a T cell-specific lentiviral vector into thymi of ZAP-70-deficient mice allows long-term T cell reconstitution and transgene expression in peripheral T lymphocytes. The efficacy of this treatment is in large part due to the context of SCID where the transgene confers a strong selective advantage (4-7). Importantly, this selective advantage is fully exploited by intrathymic injection since the inventors fail to observe T-cell reconstitution upon IV injection of the pT-ZAP vector.

a) Transduction of early T cell progenitors by intrathymic lentiviral vector injections Upon intrathymic gene transfer, it would have been possible that the peripheral T lymphocytes in pT-ZAP-treated mice arose from the expansion of a clonal or oligoclonal population of mature thymocytes derived from DP thymocytes transduced after beta chain rearrangement. The results argue against this hypothesis. Indeed, the inventors previously reported that transduced DN cells, which contain the immature T-cell progenitors, can be detected shortly after IT lentiviral injections of a non-specific (21) or a T cell specific lentiviral vector (FIG. 3). Moreover, gene-modified thymocytes could be detected for significant time periods, albeit at small numbers and in a low percentage of animals (<25%). In one pT-ZAP-injected animal who was maintained for one year, immature DN and DP thymocytes expressing eGFP (0.5%) were still detected (FIG. 4). Nevertheless, it is not clear whether this is due to the maintenance of progenitor cells in the thymus or more likely, to the recirculation of transduced progenitors into the thymus. The second hypothesis is supported by the inventor's finding that transduced lineage-negative progenitor cells can be detected in the bone marrow at >8 weeks following injection of pT-ZAP into the thymus (unpublished observations). Thus, it will be important to assess the "history" of thymic progenitors and determine whether a subpopulation of these cells can emigrate from the thymus and then reenter at later time points.

b) T cell diversity and function

The Immunoscope method is based on an RT-PCR of the hypervariable complementarity determining region 3 (CDR3), allowing the lengths of the mRNA encoding each β chain of the TCR to be analyzed. In a normal setting, each single peak is composed of multiple differently rearranged sequences. The detection of single peaks for some BV families is indicative of the expansion of single clones that would be preferentially amplified by PCR, and as such, may prevent the detection of other CDR3 products that may nevertheless be present.

The level and diversity of the pT-ZAP-reconstituted peripheral T cells is sufficient to provide the ZAP-70 immunodeficient mice with functional T-cells that respond to mitogenic stimulation in vitro, and mount in viva immune responses to skin allografts. Upon improvement of the methodology, it will be important to assess the immune responses to nominal antigen and/or infectious challenges. However, it is important to note that the TCRBV profiles detected in the IT-treated ZAP$^{-/-}$ animals is reminiscent of that of a X-SCID patient whose T cells developed from a reverse mutation in a single T cell precursor (9), resulting in a fairly good clinical condition (37). Thus, the rescue of few progenitor/stem cells can promote the differentiation of T cells with a partially diversified TCR repertoire, sufficient to provide individuals with protection from infection and a good clinical outcome.

c) Potential safety advantages of in situ gene therapy for SCID

It is noteworthy that in mice injected with the vector utilized here wherein eGFP was driven from a minimal CD4 promoter, eGFP expression was not detected in thymic stroma or liver which were the main targets transduced following IT injection using ubiquitous lentiviral vectors. In general, this is a major advantage of lentiviral vectors wherein lineage specificity can be obtained, contributing to the overall safety of the approach. Another advantage of our approach is that gene transfer was obtained in the absence of prior conditioning. Indeed, the vast majority of studies transplanting gene-modified HSC into murine SCID models were performed in lethally irradiated mice (31, 38, 39). Moreover, in human patients with ADA deficiency, a high level of immune reconstitution following injection of ex vivo gene-corrected HSC has been shown to require pre-transplantation chemotherapy (6). Importantly, in ZAP-70-deficient mice, T cell reconstitution by HSC corrected ex vivo with a ZAP-70 retroviral vector does not occur in the absence of conditioning. Altogether though, the IT injection of T cell specific lentiviral vectors without pre-conditioning represents a safety improvement for SCID gene therapy.

The inventors show that a higher frequency of reconstitution was obtained in infant as compared to adult mice, further highlighting the interest of our approach in ZAP-70 deficient children. In view of a potential clinical application, the inventors recently assessed this approach in macaques, performing direct intrathymic injection under ultrasound guidance, and determined it to be a simple and feasible technical gesture. The overall efficacy of this approach will be significantly improved in a clinical setting. Indeed, intrathymic gene transfer of lentiviral vectors is not optimal when applied to mice: (i) at similar MOIs and at equivalent levels of activation, murine T-cells are less susceptible to lentiviral infection than human T-cells (unpublished observations in ref. 37); and (ii) the small size of the mouse thymus allows neither the injection of large quantities of vectors nor repeat injections. Likewise, while the translation of gene therapy from mice to larger animals or even humans has generally resulted in decreased efficiencies, this would not be the case in this setting.

5) Methods

Lentiviral construction and virus production. The plasmid pGM1 encoding for a T-cell specific lentiviral vector expressing eGFP has been previously described (29). To obtain a T-cell specific lentiviral vector encoding ZAP-70 and eGFP, a ZAP-70-IRES-eGFP cassette (40) was inserted into the pGM1 plasmid deleted for the original eGFP coding sequences. The ensuing T-cell specific lentiviral vector pRRLSIN.PPT.CD4pmE.ZAP-70-IRES-eGFPpre is hereafter referred to as pT-ZAP. Precise cloning details are available upon request. Virions were produced by transient calcium phosphate co-transfection of 293T cells with the vector plasmid, an encapsidation plasmid lacking Vif, Vpr, Vpu and Nef accessory HIV-1 proteins (p8.91), and a vesicular stomatitis virus-G protein (VSV-G) envelope expression plasmid (pH-CMV-G) (41). Viral titers, expressed as transducing units (TU), were determined by assessing transductions of Jurkat T cells with serial dilutions of virion preparations. Expression of ZAP-70 and eGFP from this cassette is proportional as assessed in vitro, using the Jurkat T cells line.

Mice and intrathymic injections. ZAP-70$^{-/-}$ mice were bred and maintained under pathogen-free conditions. Intrathymic injections were performed at either 2-3 weeks of age (infant mice) or 6-9 weeks of age (adult mice). In the former case, virions, in a total volume of 10 uls, were injected directly through the skin into the thoracic cavity immediately above the sternum, using a 0.3 ml 28 gauge 8 mm insulin syringe. Adult mice were anesthetized with 40 mg/kg of pentobarbital. Mid-incision of the lower neck was performed to gain access to the trachea. Incision of the sternum was performed on the first two ribs and virions were injected into the visualized thymus. All experiments were approved by the local animal facility Institutional Review Board.

Immunophenotyping, proliferation and flow cytometry analyses. ZAP-70$^{-/-}$ mice were killed and dissected 6-18 weeks post-injection. Controls were obtained from age-matched 129/Sv mice. Cells from lymph nodes, spleen or thymus were stained with the indicated conjugated antibodies (Pharmingen). For proliferation analyses, splenocytes were resuspended at a concentration of $2.5 \times 10^6$ cells/ml and labeled with the fluorochrome 5-carboxyfluorescein diacetate succinimidyl ester (CFSE; Molecular Probes) as described (42). Cells were cultured as indicated in RPMI supplemented with 10% FCS and 10 μM β-mercaptoethanol in the presence of a soluble α-CD3 mAb (1 μg/ml, Pharmingen) or concanavalin A (1 μg/ml). Alternatively, a mixed lymphocyte reaction was performed by culturing lymph node cells ($5 \times 10^5$/well) in IL-2-supplemented media (50 U/ml) in the presence or absence of allogeneic Balb/c splenocytes ($5 \times 10^5$/well). All acquisitions were performed on a FACS-Calibur (Becton Dickinson) and analyses were performed with CellQuest (Becton Dickinson) or FlowJo (Tree Star) software.

Skin transplantation. Skin grafts were performed on anesthetized wild type (C57/Bl6) and ZAP-70-deficient mice as well as on ZAP-70-deficient mice with reconstituted T cells 3 months following IT injection of pT-ZAP-70. Full thickness skin grafts (0.5 cm$^2$) were prepared from the base of both syngeneic C57/Bl6 and allogeneic BalbC donor tails. Graft beds were prepared on the right and left lateral backs of recipient mice. Skin gratis from both C57/Bl6 and BalbC mice were attached to the backs of each mouse with interrupted sutures of silk thread and graft appearance was monitored 3 times a week. Paraffin sections were prepared following formalin fixation of biopsied grafts. Sections were stained with hematoxylin and eosin.

TCR CDR3 size analyses. Total RNA was prepared using RNAble (Furobio, Les Ulis, France). Five μg of RNA was reverse transcribed using oligo(dT) primers (Pharmacia Biotech) and M-MLV reverse transcriptase (Gibco BRL). cDNAs were amplified (cycles 1 min. 94° C., 1 min 60° C., 2 min. 72° C.) using 2.5 U of the AmpliTaq polymerase (Roche) in a 50 μl reaction mixture with one of 14 TCRBV subfamily-specific primers and a Cβ primer recognizing the constant regions Cβ1 and Cβ2 of the beta chain of the TCR. The final concentration was 0.5 μM for each primer, 0.2 mM dNTPs, 2 mM MgCl2 in 1× PCR Buffer (Roche). Two μl of each PCR was further processed in a run-off reaction (10 cycles 1 min. 94° C., 1 min 60° C., 2 min. 72° C.) using 0.2 μM of a ROX-labeled Cβ primer (Proligo France, Paris, France) and 2.5 U of the AmpliTaq polymerase (Roche). Each run-off product was denaturated and loaded on a gel for fluorescence analysis using an Applied Biosystem 377 sequencer (PerkinElmer). To obtain the CDR3 length profiles depicted in FIG. 6, raw data were analysed using the Immunoscope software (Loginserm, Paris, France). The TCRBV nomenclature proposed by Arden et al. was used in this study (43).

TABLE 1

Percentages of CD3+ lymphocytes in ZAP-70$^{-/-}$ mice following in situ thymic injection of a ZAP-70-expressing lentiviral vector. ZAP-70$^{-/-}$ mice were injected with the ZAP-70-expressing lentiviral vector at the indicated ages and analyzed at 12-52 weeks post injection as noted. The percentages of CD3+ T cells in the lymph nodes of sacrificed animals as well as the percentages of the eGFP+ cells within the CD3+ populations were determined by flow cytometry. Note that presented analyses of IT-injected mice are limited to those mice showing T cell reconstitution for whom lymph node analyses were performed. The percentages of T cells in control ZAP-70$^{-/-}$ and WT mice are shown.

| Mouse | Age at injection (weeks) | Time post-injection (weeks) | % CD3 T cells | % EGFP + T cells |
|---|---|---|---|---|
| ZAP$^{-/-}$ 1 | / | / | 3 | 1 |
| ZAP$^{-/-}$ 2 | / | / | 4 | 2 |
| ZAP$^{-/-}$ 3 | / | / | 3 | <0.5 |
| ZAP$^{-/-}$ IT #5-13 | 12 | 20 | 23 | 14 |
| ZAP$^{-/-}$ IT #5-10 | 12 | 1 year | 19 | 44 |
| ZAP$^{-/-}$ IT #2-6 | 9 | 8 | 26 | 66 |
| ZAP$^{-/-}$ IT #3-2 | 9 | 10 | 13 | 35 |
| ZAP$^{-/-}$ IT #5-6 | 4 | 20 | 23 | 25 |
| ZAP$^{-/-}$ IT #4-3 | 2 | 20 | 11 | 15 |
| ZAP$^{-/-}$ IT #4-4 | 2 | 20 | 20 | 25 |
| ZAP$^{-/-}$ IT #4-5 | 2 | 20 | 16 | 41 |
| ZAP$^{-/-}$ IT #6-5 | 2 | 15 | 11 | 48 |
| ZAP$^{-/-}$ IT #7-2 | 2 | 17 | 16 | 42 |
| ZAP$^{-/-}$ IT #7-3 | 2 | 17 | 10 | 14 |
| WT 1 | / | / | 75 | <0.5 |
| WT 2 | / | / | 51 | <0.5 |
| WT 3 | / | / | 64 | <0.5 |

6) References

1. Antoine, C., Muller, S., Cant, A., Cavazzana-Calvo, M., Veys, P., Vossen, J., Fasth, A., Heilmann, C., Wulffraat, N., Seger, R., et al. 2003. Long-term survival and transplantation of haemopoietic stem cells for immunodeficiencies: report of the European experience 1968-99. Lancet 361:553-560.

2. Buckley, R. H., Schiff, S. E., Schiff, R. I., Markert, L., Williams, L. W., Roberts, J. L., Myers, L. A., and Ward, F. E. 1999. Hematopoietic stem-cell transplantation for the treatment of severe combined immunodeficiency. N Engl J Med 340:508-516.

3. Patel, D. D., Gooding, M. E., Parrott, R. E., Curtis, K. M., Haynes, B. F., and Buckley, R. H. 2000. Thymic function after hematopoietic stem-cell transplantation for the treatment of severe combined immunodeficiency. N Engl J Med 342:1325-1332.

4. Kohn, D. B., Hershfield, M. S., Carbonaro, D., Shigeoka, A., Brooks, J., Smogorzewska, E. M., Barsky, L. W., Chan, R., Burotto, F., Annett, G., et al. 1998. T lymphocytes with a normal ADA gene accumulate after transplantation of transduced autologous umbilical cord blood CD34+ cells in ADA-deficient SCID neonates. *Nat Med* 4:775-780.

5. Cavazzana-Calvo, M., Hacein-Bey, S., de Saint Basile, G., Gross, F., Yvon, E., Nusbaum, P., Selz, F., Hue, C., Certain, S., Casanova, J. L., et al. 2000. Gene therapy of human severe combined immunodeficiency (SCID)-X1 disease. *Science* 288:669-672.

6. Aiuti, A., Slavin, S., Aker, M., Ficara, F., Deola, S., Mortellaro, A., Morecki, S., Andolfi, G., Tabucchi, A., Carlucci, F., et al. 2002. Correction of ADA-SCID by stem cell gene therapy combined with nonmyeloablative conditioning. *Science* 296:2410-2413.

7. Gaspar, H. B., Parsley, K. L., Howe, S., King, D., Gilmour, K. C., Sinclair, J., Brouns, G., Schmidt, M., Von Kalle, C., Barington, T., et al. 2004. Gene therapy of X-linked severe combined immunodeficiency by use of a pseudotyped gammaretroviral vector. *Lancet* 364:2181-2187.

8. Hirschhorn, R., Yang, D. R., Puck, J. M., Huie, M. L., Jiang, C. K., and Kurlandsky, L. E. 1996. Spontaneous in vivo reversion to normal of an inherited mutation in a patient with adenosine deaminase deficiency. *Nat Genet* 13:290-295.

9. Bousso, P., Wahn, V., Douagi, I., Horneff, G., Pannetier, C., Le Deist, F., Zepp, F., Niehues, T., Kourilsky, P., Fischer, A., et al. 2000. Diversity, functionality, and stability of the T cell repertoire derived in vivo from a single human T cell precursor. *Proc Natl Acad Sci USA* 97:274-278.

10. Stephan, V., Wahn, V., Le Deist, F., Dirksen, U., Broker, B., Muller-Fleckenstein, I., Horneff, G., Schroten, H., Fischer, A., and de Saint Basile, G. 1996. Atypical X-linked severe combined immunodeficiency due to possible spontaneous reversion of the genetic defect in T cells. *N Engl J Med* 335:1563-1567.

11. Ariga, T., Oda, N., Yamaguchi, K., Kawamura, N., Kikuta, H., Taniuchi, S., Kobayashi, Y., Terada, K., Ikeda, H., Hershfield, M. S., et al. 2001. T-cell lines from 2 patients with adenosine deaminase (ADA) deficiency showed the restoration of ADA activity resulted from the reversion of an inherited mutation. *Blood* 97:2896-2899.

12. Cavazzana-calvo, M., Hacein-Bey, S., De Saint Basile, G., Gross, F., Nusbaum, P., Yvon, E., Casanova, G. L., Le Deist, F., and Fisher, A. 1999. Correction of SCID-XI disease phenotype following gc gene transfer by a retroviral vector into CD34+ cells in two children. *Abstract in Blood, A. S. H.* 94 sup 1:367a.

13. Fischer, A., Hacein-Bey, S., and Cavazzana-Calvo, M. 2002. Gene therapy of severe combined immunodeficiencies. *Nat Rev Immunol* 2:615-621.

14. Hacein-Bey-Abina, S., von Kalle, C., Schmidt, M., Le Deist, F., Wulffraat, N., McIntyre, E., Radford, I., Villeval, J. L., Fraser, C. C., Cavazzana-Calvo, M., et al. 2003. A serious adverse event after successful gene therapy for X-linked severe combined immunodeficiency. *N Engl J Med* 348:255-256.

15. Li, Z., Dullmann, J., Schiedlmeier, B., Schmidt, M., von Kalle, C., Meyer, J., Forster, M., Stocking, C., Wahlers, A., Frank, O., et al. 2002. Murine leukemia induced by retroviral gene marking. *Science* 296:497.

16. Esslinger, C., Chapatte, L., Finke, D., Miconnet, I., Guillaume, P., Levy, F., and MacDonald, H. R. 2003. In vivo administration of a lentiviral vaccine targets DCs and induces efficient CD8(+) T cell responses. *J Clin Invest* 111:1673-1681.

17. VandenDriessche, T., Thorrez, L., Naldini, L., Follenzi, A., Moons, L., Berneman, Z., Cotten, D., and Chuah, M. K. 2002. Lentiviral vectors containing the human immunodeficiency virus type-1 central polypurine tract can efficiently transduce nondividing hepatocytes and antigen-presenting cells in vivo. *Blood* 100:813-822.

18. Yanay, O., Barry, S. C., Katen, L. J., Brzezinski, M., Flint, L. Y., Christensen, J., Liggitt, D., Dale, D. C., and Osborne, W. R. 2003. Treatment of canine cyclic neutropenia by lentivirus-mediated G-CSF delivery. *Blood* 102:2046-2052. Epub 2003 May 2015.

19. Palmowski, M., Salio, M., Dunbar, R. P., and Cerundolo, V. 2002. The use of HLA class I tetramers to design a vaccination strategy for melanoma patients. *Immunol Rev* 188:155-161.

20. Kobinger, G. P., Louboutin, J. P., Barton, E. R., Sweeney, H. L., and Wilson, J. M. 2003. Correction of the dystrophic phenotype by in vivo targeting of muscle progenitor cells. *Hum Gene Ther* 14:1441-1449.

21. Baekelandt, V., Eggermont, K., Michiels, M., Nuttin, B., and Debyser, Z. 2003. Optimized lentiviral vector production and purification procedure prevents immune response after transduction of mouse brain. *Gene Ther* 10:1933-1940.

23. Allman, D., Sambandam, A., Kim, S., Miller, J. P., Pagan, A., Well, D., Meraz, A., and Bhandoola, A. 2003. Thymopoiesis independent of common lymphoid progenitors. *Nat Immunol* 4:168-174.

24. Chan, A. C., Iwashima, M., Turck, C. W., and Weiss, A. 1992. ZAP-70: a 70 kd protein-tyrosine kinase that associates with the TCR zeta chain. *Cell* 71:649-662.

25. Chan, A. C., van Oers, N. S., Tran, A., Turka, L., Law, C. L., Ryan, J. C., Clark, E. A., and Weiss, A. 1994. Differential expression of ZAP-70 and Syk protein tyrosine kinases, and the role of this family of protein tyrosine kinases in TCR signaling. *J Immunol* 152:4758-4766.

26. Negishi, I., Motoyama, N., Nakayama, K., Senju, S., Hatakeyama, S., Zhang, Q., Chan, A. C., and Loh, D. Y. 1995. Essential role for ZAP-70 in both positive and negative selection of thymocytes. *Nature* 376:435-438.

27. Wiest, D. L., Ashe, J. M., Howcroft, T. K., Lee, H. M., Kemper, D. M., Negishi, I., Singer, D. S., Singer, A., and Abe, R. 1997. A spontaneously arising mutation in the DLAARN motif of murine ZAP-70 abrogates kinase activity and arrests thymocyte development. *Immunity* 6:663-671.

28. Kadlecek, T. A., van Oers, N. S., Lefrancois, L., Olson, S., Finlay, D., Chu, D. H., Connolly, K., Killeen, N., and Weiss, A. 1998. Differential requirements for ZAP-70 in TCR signaling and T cell development. *J Immunol* 161:4688-4694.

29. Marodon, G., Mouly, E., Blair, E. J., Frisen, C., Lemoine, F. M., and Klatzmann, D. 2003. Specific transgene expression in human and mouse CD4+ cells using lentiviral vectors with regulatory sequences from the CD4 gene. *Blood* 101:3416-3423.

30. Porritt, H. E., Gordon, K., and Petrie, H. T. 2003. Kinetics of steady-state differentiation and mapping of intrathymic-signaling environments by stem cell transplantation in nonirradiated mice. *J Exp Med* 198:957-962.

31. Otsu, M., Steinberg, M., Ferrand, C., Merida, P., Rebouissou, C., Tiberghien, P., Taylor, N., Candotti, F., and Noraz, N. 2002. Reconstitution of lymphoid development and function in ZAP-70-deficient mice following gene transfer into bone marrow cells. *Blood* 100:1248-1256.

32. Bellier, B., Thomas-Vaslin, V., Saron, M. F., and Klatzmann, D. 2003. Turning immunological memory into amnesia by depletion of dividing T cells. *Proc Natl Acad Sci USA* 100:15017-15022. Epub 12003 Nov 15021.

33. Puisieux, I., Bain, C., Merrouche, Y., Malacher, P., Kourilsky, P., Even, J., and Favrot, M. 1996. Restriction of the T-cell repertoire in tumor-infiltrating lymphocytes from nine patients with renal-cell carcinoma. Relevance of the CDR3 length analysis for the identification of in situ clonal T-cell expansions. *Int J Cancer* 66:201-208.

34. Pannetier, C., Even, J., and Kourilsky, P. 1995. T-cell repertoire diversity and clonal expansions in normal and clinical samples. *Immunol Today* 16:176-181.

35. Williams, B. L., Schreiber, K. L., Zhang, W., Wange, R. L., Samelson, L. E., Leibson, P. J., and Abraham, R. T. 1998. Genetic evidence for differential coupling of Syk family kinases to the T-cell receptor: reconstitution studies in a ZAP-70-deficient Jurkat T-cell line. *Mol Cell Biol* 18:1388-1399.

36. Unutmaz, D., KewalRamani, V. N., Marmon, S., and Littman, D. R. 1999. Cytokine signals are sufficient for HIV-1 infection of resting human T lymphocytes. *J Exp Med* 189:1735-1746.

37. Hirschhorn, R. 2003. In vivo reversion to normal of inherited mutations in humans. *J Med Genet* 40:721-728.

38. Lo, M., Bloom, M. L., Imada, K., Berg, M., Bollenbacher, J. M., Bloom, E. T., Kelsall, B. L., and Leonard, W. J. 1999. Restoration of lymphoid populations in a murine model of X-linked severe combined immunodeficiency by a gene-therapy approach. *Blood* 94:3027-3036.

39. Otsu, M., Anderson, S. M., Bodine, D. M., Puck, J. M., O'Shea, J. J., and Candotti, F. 2000. Lymphoid development and function in X-linked severe combined immunodeficiency mice after stem cell gene therapy. *Mol Ther* 1:145-153.

40. Steinberg, M., Swainson, L., Schwarz, K., Boyer, M., Friedrich, W., Yssel, H., Taylor, N., and Noraz, N. 2000. Retrovirus-mediated transduction of primary ZAP-70-deficient human T cells results in the selective growth advantage of gene-corrected cells: implications for gene therapy. *Gene Ther* 7:1392-1400.

41. Yee, J. K., Miyanohara, A., LaPorte, P., Bouie, K., Burns, J. C., and Friedmann, T. 1994. A general method for the generation of high-titer, pantropic retroviral vectors: highly efficient infection of primary hepatocytes. *Proc Natl Acad Sci USA* 91:9564-9568.

42. Dardalhon, V., Jaleco, S., Kinet, S., Herpers, B., Steinberg, M., Ferrand, C., Froger, D., Leveau, C., Tiberghien, P., Charneau, P., et al. 2001. IL-7 differentially regulates cell cycle progression and HIV-1-based vector infection in neonatal and adult CD4+ T cells. *Proc Natl Acad Sci USA* 98:9277-9282.

43. Arden, B., Clark, S. P., Kabelitz, D., and Mak, T. W. 1995. Human T-cell receptor variable gene segment families. *Immunogenetics* 42:455-500.

7) Figure Legends

FIG. 1. Schematic representation of the pCD4 lentiviral vector encoding wild-type ZAP-70. The relative positions of the elements contained within the pCD4 lentiviral vector are indicated. 5' LTR, long terminal repeat (LTR); SD, splice donor; SA, splice acceptor; Ψ, packaging signal; GA-RRE, truncated gag sequence with the rev responsive element; cppT, central polypurine tract of HIV; CD4pmE, human CD4 minimal promoter/murine enhancer cassette (590 bp); ZAP-70 cDNA; IRES, internal ribosome entry site; eGFP, enhanced green fluorescent protein cDNA; WPRE, post-transcriptional cis-acting regulatory element of the woodchuck hepatitis virus (587 bp); and LTR-SIN, self inactivating 3' LTR (deleted of 400 bp in the U3 region).

FIG. 2. Thymocyte differentiation in ZAP-70$^{-/-}$ mice following in situ injection of a ZAP-70-expressing lentiviral vector. A ZAP-70-expressing lentiviral vector (pT-ZAP) was injected intrathymically into 8-12 week old ZAP-70$^{-/-}$ mice and thymocytes were harvested from euthanized animals 7-13 weeks later. (A) Total thymocytes were stained with Cy-conjugated α☐CD8 and APC-conjugated α☐CD4 mAbs. The percentages of double positive and CD4+ and CD8+ single positive (SP) thymocytes in WT (C57/Bl6), ZAP-70$^{-/-}$, and in vivo-reconstituted mice are indicated in each dot plot. (B) The percentages of eGFP+ cells within the entire thymus as well as within the thymocyte subset wherein TCRβ was upregulated are shown. The CD4/CD8 distributions of TCR-upregulated thymocytes within the EGFP– population of ZAP-70$^{-/-}$ and WT mice are shown. Additionally, the CD4/CD8 distributions within the EGFP– and EGFP+ TCRβ-upregulated populations in a ZAP-70$^{-/-}$ mice injected with the pT-ZAP lentivector are compared. The IT-injected mouse was sacrificed at 8 weeks post treatment and results are representative of data obtained from 6 mice FIG. 3. Kinetics of peripheral T lymphocyte emigration following in situ thymic injection of a ZAP-70-expressing lentiviral vector. (A) The presence of CD4+ and CD8+ T lymphocytes in the peripheral blood of ZAP-70$^{-/-}$ mice was monitored by flow cytometry at 4 and 6 weeks post intrathymic injection of the pT-ZAP lentiviral vector. The overall percentage of CD4+ and CD8+ T cells within the peripheral blood at these time points is indicated. Analyses of representative ZAP-70$^{-/-}$ and WT mice are also shown. (B) The percentages of eGFP+ cells in the peripheral blood of all animals are shown. The CD4/CD8 phenotypes of the eGFP+ cells isolated from the pT-ZAP-injected mice at 4 and 6 weeks were evaluated by specifically gating on this population.

FIG. 4. T lymphocyte reconstitution in ZAP-70$^{-/-}$ mice following in situ injection of a ZAP-70-expressing lentiviral vector. Lymph nodes were collected from WT, ZAP-70$^{-/-}$, and ZAP-70$^{-/-}$ mice intrathymically injected with the pT-ZAP lentiviral vector (ZAP-70$^{-/-}$ IT). (A) The percentages of CD4, CD8, CD3 and CD19 cells are indicated. (B) The activation status of the T cell population was determined using PE-conjugated α☐CD25 and α☐CD69 mAbs and the relative percentages of naïve and memory T cells were monitored with a mAb recognizing CD62L (CD62L+ and CD62L–, respectively). The percentages of positively stained cells are indicated in each histogram. The representative IT-reconstituted mice presented here was sacrificed at 8 weeks post injection.

FIG. 5. ZAP-70 expression and diversity in T lymphocytes reconstituted by intrathymic injection of the pT-ZAP lentiviral vector. (A) ZAP-70 levels in total splenocytes from WT and IT-reconstituted ZAP-70 mice as well as in sorted CD3+ and CD3– populations were assessed in western blots using an αZAP-70 mAb. (B) The TCRBV repertoire was assessed by a comparison of T cell receptor CDR3 size distribution (Immunoscope profiles) of lymph node cells obtained from WT and IT-reconstituted adult ZAP-70$^{-/-}$ mice. PCR products were generated by reverse transcription with different TCRBV subfamily-specific primers and 1 constant β consensus primer (Cβ), followed by a run-off reaction with a fluorescent Cβ primer. The graphs represent fluorescence intensity in arbitrary units (y axis) plotted against CDR3 size (x axis). Representative results showing the size distributions within 14 TCRBV families are shown.

Figure 6:
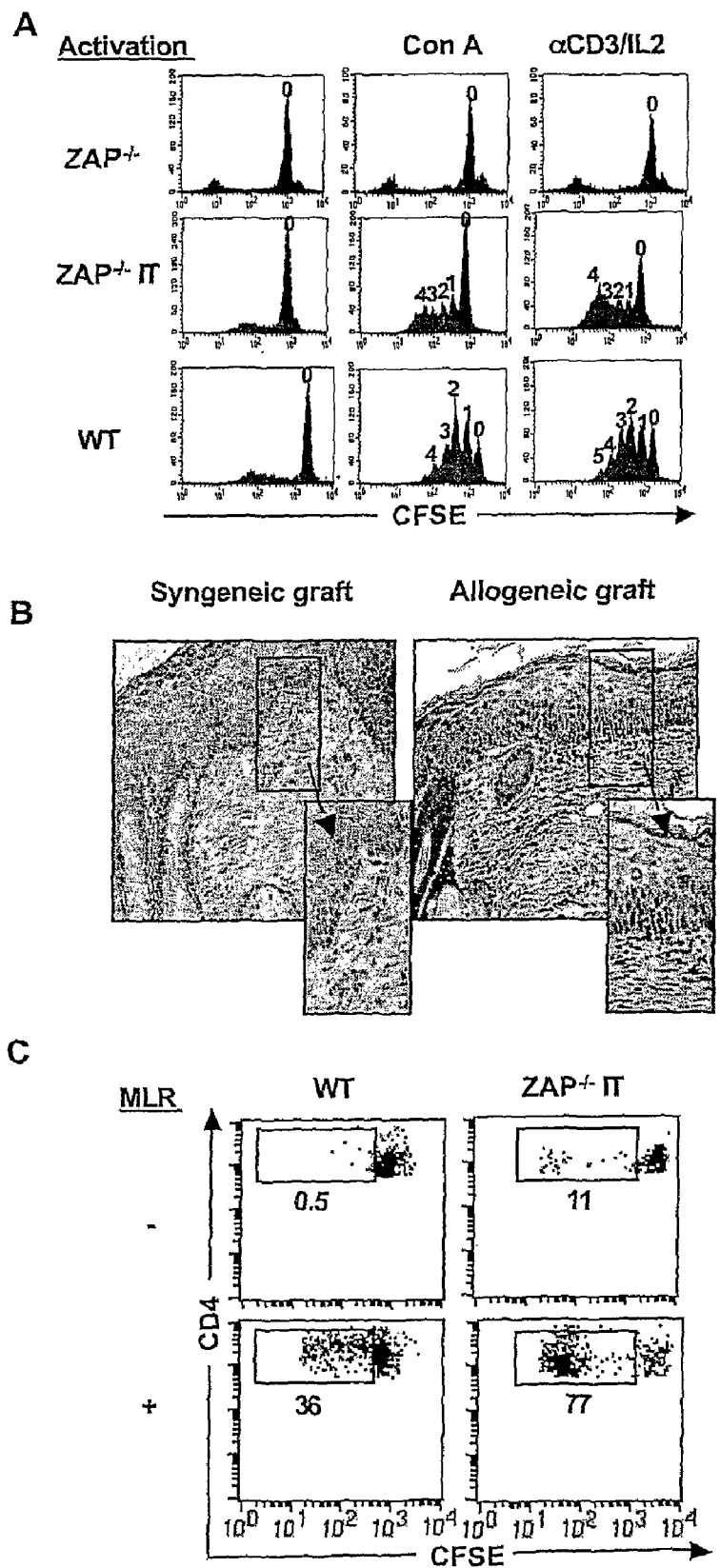
FIG. 6. In vitro and in vivo responsiveness of T lymphocytes reconstituted by intrathymic injection of pT-ZAP. (A) Splenocytes from ZAP-70$^{-/-}$, WT and IT-reconstituted ZAP-70$^{-/-}$ mice were labeled with the fluorescent dye CFSE and cultured in vitro in the presence of concanavalin A or αCD3/IL-2 for 3 days and cells were analyzed for CFSE intensity by flow cytometry. (B) Histological sections of syngeneic (C57/Bl6) and allogeneic (BalbC) skin sections, which had both been grafted on the same IT-reconstituted ZAP-70 mouse, were stained with hematoxylin and eosin. (C) Lymph node cells from a WT (C57/Bl6) and IT-reconstituted ZAP-70 mouse were stained with an αCD4 mAb and the percentages of CD4+ cells that divided, as assessed by a loss of CFSE intensity, are indicated in each dot blot.

FIG. 6. In vitro and in vivo responsiveness of T lymphocytes reconstituted by intrathymic injection of pT-ZAP. (A) Splenocytes from ZAP-70$^{-/-}$, WT and IT-reconstituted ZAP-70$^{-/-}$ mice were labeled with the fluorescent dye CFSE and cultured in vitro in the presence of concanavalin A or αCD3/IL-2 for 3 days and cells were analyzed for CFSE intensity by flow cytometry. The numbers shown above the peaks indicate the number of cell divisions. The IT-reconstituted ZAP-70 mice was sacrificed at 8 weeks post injection. (B) Histological sections of syngeneic (C57/Bl6) and allogeneic (BalbC) skin sections, which had both been grafted on the same IT-reconstituted ZAP-70 mouse, were stained with hematoxylin and eosin. The presence of lymphocytes (detected as dark purple staining) infiltrating the epidermis is shown in the enlarged inset. The IT-reconstituted mouse was injected 14 weeks prior to skin grafting and skin histology was performed 30 days later. A magnification of 20× is shown. (C) Lymph node cells from a WT (C57/Bl6) and IT-reconstituted ZAP-70 mouse (pre-grafted as described above; sacrificed at 6 weeks post-graft) were labeled with CFSE and cultured in the absence (−) or presence (+) of allogeneic BalbC splenocytes (MLR; mixed lymphocyte reaction). After 3 days, cells were stained with an αCD4 mAb and the percentages of CD4+ cells that divided, as assessed by a loss of CFSE intensity, are indicated in each dot blot.

Figure 7:
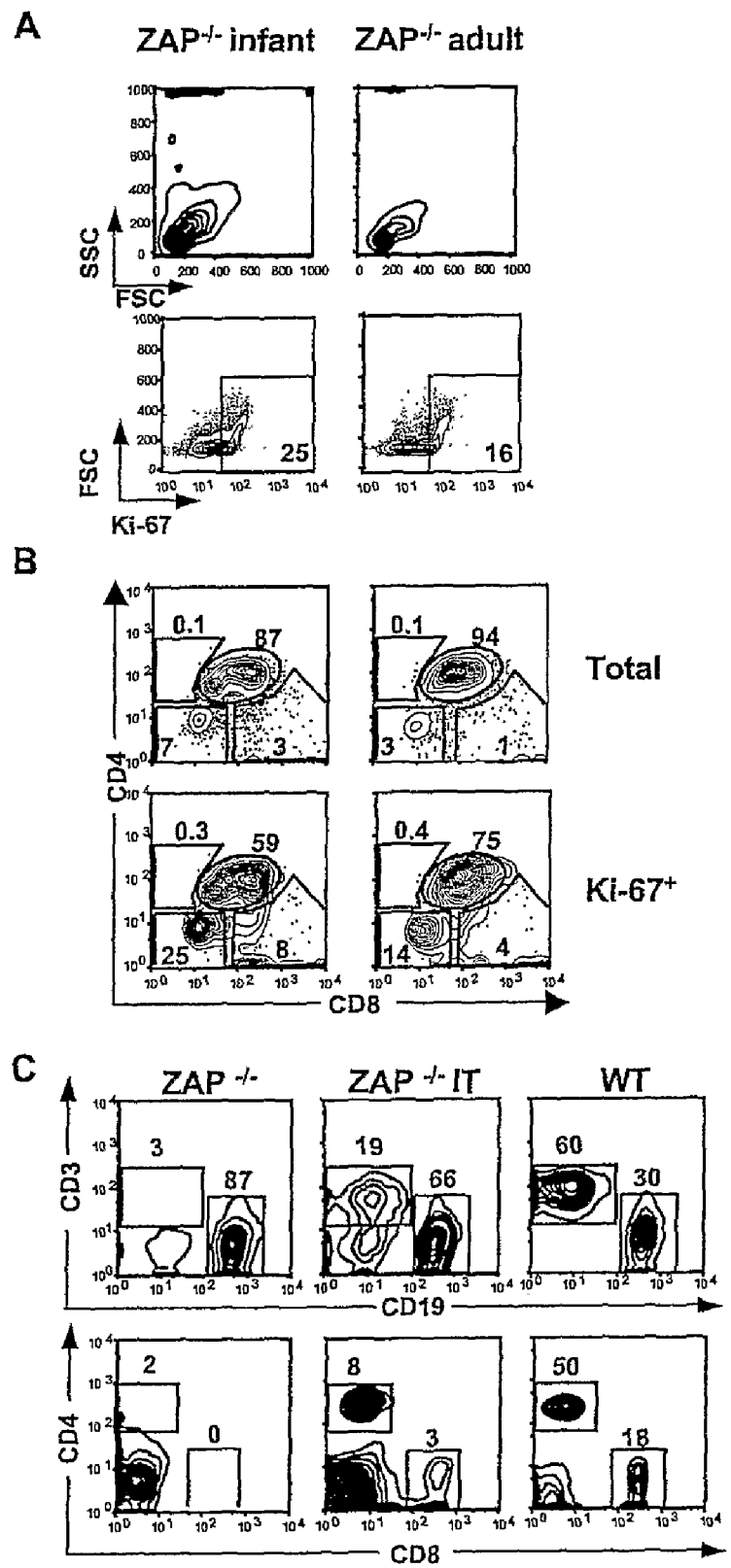
FIG. 7—Enhanced T cell reconstitution efficiency following intrathymic injection of a ZAP-70-expressing lentiviral vector in infant mice. (A) The forward angle (FSC) and side angle (SSC) light scatters profiles of thymi from a 2 week old (infant) and adult ZAP-70 KO mouse are shown. (B) T cell reconstitution in the lymph node of a ZAP-70 KO infant mouse intrathymically injected with the pT-ZAP lentiviral vector was monitored by flow cytometry and is representative of 9/10 IT-treated infant mice.

FIG. 7. Enhanced T cell reconstitution efficiency following intrathymic injection of a ZAP-70-expressing lentiviral vector in infant mice. (A) The forward angle (FSC) and side angle (SSC) light scatters profiles of thymi from a 2 week old (infant) and adult ZAP-70 KO mouse are shown. Cell cycle entry of total thymocytes from an infant and adult ZAP-70 KO mouse was monitored by assessing intracellular expression of the Ki-67 antigen using a fluorochrome-conjugated mAb. The CD4/CD8 distribution within the fractions of Ki67+ thymocytes is shown. (B) T cell reconstitution in the lymph node of a ZAP-70 KO infant mouse intrathymicaily injected with the pT-ZAP lentiviral vector was monitored by flow cytometry and is representative of 9/10 IT-treated infant mice.

Figure 8:
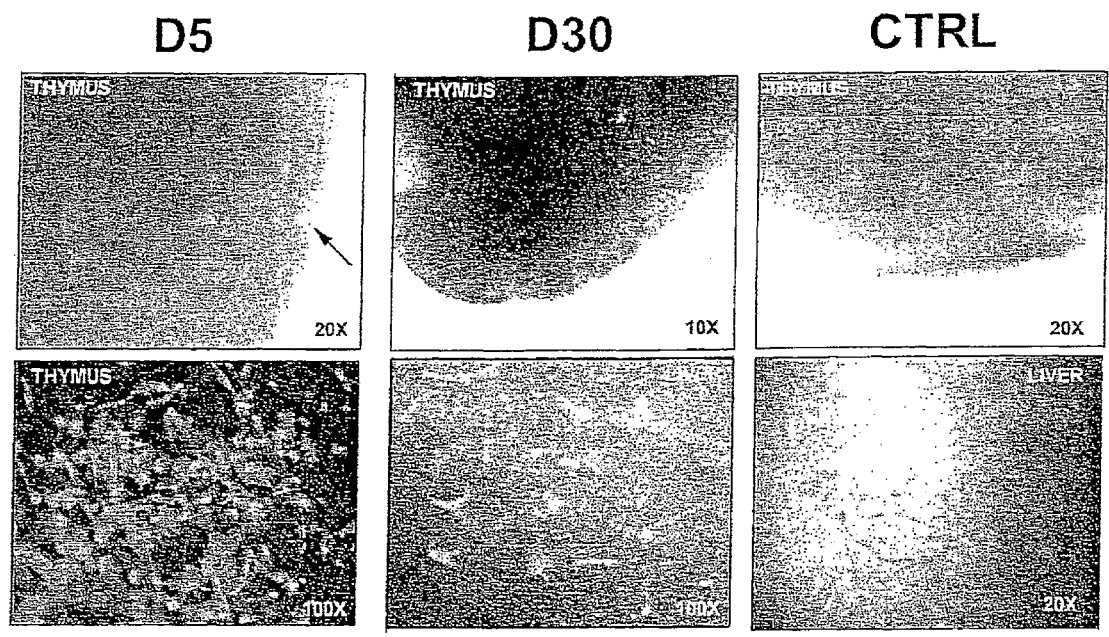
FIG. 8—In vivo expression of eGFP after intrathymic injection of the LvPGK-GFP vector. D5: day 5 post-injection. D30: day 30 post-injection. CTRL: control mice injected IT with PBS.
Figure 10:
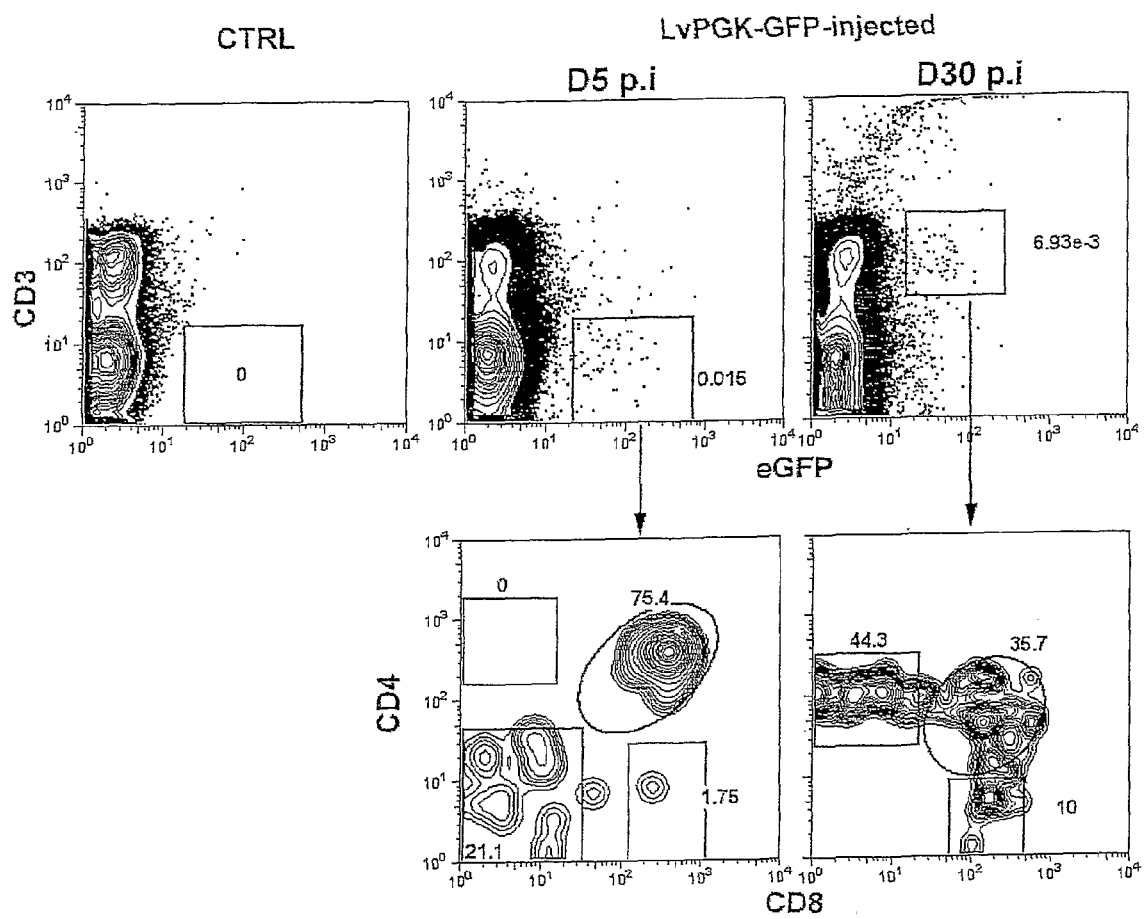
FIG. 10—eGFP expression in developing thymocytes.

II) In Situ Transduction of Stromal Cells and Thymocytes Upon Intrathymic Injection of Lentiviral Vector 1) Results a) Intrathymic injection of lentiviral vectors results in the efficient and persistent infection of thymic stromal cells The inventors used a concentrated viral stock of the LvPGK-GFP vector ($2.10^9$ $TU_{143B}$/ml) to inject between $7 \times 10^7$ to $1.2 \times 10^8$ infectious units in the thymus of normal C57Bl/6 mice. Infected cells could readily be detected at day 5 post-injection by direct examination of the thymi under a UV microscope (FIG. 8). Of note, transduced cells could still be observed at 1 (FIG. 8) and 3 months (data not shown) post injection. Most of the transduced cells had a fibroblastic morphology. To monitor a possible passage of the vector through the bloodstream, the inventors checked for the presence of transduced cells in the liver, which is the primary target organ after intravenous injection of lentiviral vectors [14a]. The inventors indeed observed numerous eGFP+ cells in the liver (FIG. 8), suggesting a significant leak into the circulation upon IT injection of up to 30 µl of the vector. Nevertheless, the results demonstrate efficient and persistent infection of thymic stromal cells upon IT injection of a lentiviral vector.

b) Induction of negative selection after intrathymic injection of lentiviral vectors The inventors next wanted to investigate whether thymic stromal cells infected with a lentiviral vector would be able to mediate negative selection of developing thymocytes. The inventors thus injected a lentiviral vector encoding the HA of the Influenza virus, or eGFP as a control, into the thymus of SFE-Tg mice expressing a TCR specific for a HA protein peptide and for which a clonotypic antibody recognizing the transgenic TCR (clone 6.5) is available [15a]. Six days after injection, the inventors analyzed the thymocytes by flow cytometry after thymi dilacerations. The frequency of $6.5^+$ cells within CD4SP and CD8SP thymocytes is shown in FIG. 9A for a representative experiment. Intrathymic injection of the LvPGK-HA vector resulted in a diminution in the frequencies of $6.5^+$ cells within CD4SP by a factor of 2 and by a factor of 5 in CD8SP cells with an almost complete disappearance of $6.5^{hi}$ cells in the latter subset. Of note is that the intensity of TCR transgenic expression was reduced in CD4SP cells (FIG. 9A). Overall, the inventors observed a 3.5-fold decrease in the total numbers of thymocytes expressing the specific TCR in mice injected with the LvPGK-HA vector compared to the LvPGK-GFP vector (FIG. 9B). Our results altogether demonstrate that within a week after intra thymic injection of the LvPGK-HA vector, infected thymic stromal cells efficiently mediated negative selection of HA-specific thymocytes.

c) Intrathymic injection of lentiviral vectors results in low level infection of immature thymocytes The inventors next investigated whether developing T-cells would be infected upon IT injection of the lentiviral vector. Five days post-injection of the LvPGK-GFP vector into the thymus of a normal mouse, very few eGFP+ cells could be detected by flow cytometry within the thymocytes obtained from dilacerated thymi (FIG. 10). Most of these cells were CD3− cells, and belonged to the DN and DP subsets, showing that infected cells were mostly immature. Interestingly, at day 30 post-injection, the inventors observed more mature eGFP+ cells that expressed CD3 and that belonged to the subsets of CD4SP and CD8SP for more than half of them. This result indicates that infection per se did not interfere with the normal process of T-cell development. Moreover, the inventors observed a similar repartition of CD4/CD8-expressing cells in non-infected eGFP− cells. Collectively, these results show that immature thymocytes can be infected by in situ lentiviral infection. However, the inventors were unable to clearly detect infected T-cells in the spleen of injected mice, likely due to their small representation within the pool of mature lymphocytes in the absence of a selective advantage for the transduced thymocytes.

2) Discussion

The inventors report herein that IT injection of a lentiviral vector results in the predominant infection of thymic stromal cells, and to a low level infection of thymocyte progenitors. Significant infection of liver cells was also detected. This observation is reminiscent of what was observed by DeMatteo et al. with adenoviral vectors [7a]. Together with the fact that liver cells are main targets of IV-injected lentiviral or adenoviral vectors, this suggest that a significant leak into the circulation does occur upon IT injection of viral vectors. Our in situ analysis shows that thymic epithelial cells represent the vast majority of infected cells. Whatever the proportion of cortical, medullar epithelial cells, or thymic dendritic cells that are transduced, the inventors show here that this results in an antigen presentation that efficiently mediates negative selection of specific thymocytes. This is not due to the injection of a "crude" preparation of viral supernatant that could have non-specifically affected T cell differentiation. Indeed, the inventors injected 10 times lower amounts of p24 from the LvPGK-HA vector than of the LvPGK-GFP vectors, suggesting that negative selection of HA-specific thymocytes was a direct effect of HA expression by thymic stromal cells. This is further supported by the analysis of the frequencies of $6.5^+$ thymocytes which shows deletion of $6.5^{hi}$ cells within CD8SP cells, an MHC class-II restricted population in these TCR-transgenic mice [15a]. Down modulation of the transgenic TCR and deletion was observed within CD4SP cells. This is reminiscent of the results obtained recently by Trani et al. which showed that intra thymic delivery of increasing dose of the HA peptide in SFE TCR-Tg mice resulted in the down regulation of the transgenic TCR [16a]. Therefore, deletion and/or receptor down regulation may act in concert in the negative selection of HA-specific CD4SP cells SFE transgenic mice.

A very low infection of developing thymocytes was detected. This is not surprising as (i) the multiplicity of infection (ratio of number of infectious units over number of total cells in the thymus) was estimated to be lower than 0.4 and (ii) lentiviral transduction of murine T cells is far less efficient than of human T cells [17a]. Since the actual volume that can be injected in a mouse thymus is however limited, the inventors used the highest MOI achievable with the concentrated vectors. It should be stressed though that at day 5 after injection, the infected cells represented immature thymocytes not expressing CD3 molecules. At later time points, infection was detected in more mature thymocytes. This result may have important implications for in vivo gene therapy of severe combined immunodeficiencies (SCID) affecting T-cell development (reviewed in [18a]). Indeed, most of these diseases are due to monogenic mutations and concerns immature thymocytes, such as in the $T^-B^+NK^-$ deficiencies linked to the common cytokine receptor gamma-c [19a], or to the ZAP-70 protein tyrosine kinase [20a]. These results open the possibility of correcting these developmental blocks through IT delivery of a lentiviral vector expressing a functional molecule. For this particular application, it would be important to avoid transgene expression in the thymic stroma. The use of the recently described T-cell specific lentiviral vector represent an attractive possibility towards this end [21a]. Given the tremendous proliferative potential of T cells and the selective advantage that will be provided by the transgene, even a low number of transduced cells should result in a significant T cell reconstitution. This is best exemplified by a unique case of X-linked severe combined immunodeficiency in which a reverse mutation occurred in a single early T cell precursor. It was determined that at least 1,000 T cell clones with unique T cell receptor-beta sequences were generated from this precursor and that this diversity seems to be stable over time and provides protection from infections in vivo [22a]. Furthermore, these results show that intra thymic delivery of the ZAP-70 gene by mean of a T-cell specific lentiviral vector in ZAP-70-deficient mice results in the restoration of T-cell development (see above). The presently described approach represents an alternative to gene therapy protocols using cumbersome haematopoietic stem cell manipulation ex vivo prior to their reinfusion in vivo.

3) Conclusions

Results presented herein have important implications for the experimental or therapeutic manipulation of the immune system, and notably for tolerance induction and the correction of SCID.

4) Methods

Mice and intrathymic surgery. C57Bl/6 mice at 6 weeks of age were used at 8 to 10 weeks-old. SFE TCR-Tg mice [15a] were bred in our own animal facility and were used at 6 to 10 weeks-old. Intrathymic surgery was performed after anesthetic treatment of animals with 40 mg/kg of Pentobarbital (Sanofi-Synthelabo, Gentilly, France). Mid-incision of the lower neck was performed to gain access to the trachea. Incision of the sternum was performed on the first two ribs and gently pulled aside to view the thymus. A single injection of 10 to 30 µl was performed using 0.3 ml Terumo insulin syringes (VWR, Fontenay-sous-bois, France).

Lentiviral vector construction, production, concentration and quantification. The plasmid encoding the lentiviral vector pRRLsin.PPT.hPGK.GFPpre (LvPGK-GFP) has been described elsewhere [23a]. To construct the plasmid encoding the hemaglutinin (HA) protein of the Influenza virus, BamHI and SalI restriction sites at the 5' and 3' ends, respectively, were added to the cDNA of the HA protein of Influenza virus (H1N1) in the pCIneoHA plasmid (provided by Genethon, Evry, France) by PCR using the Taq polymerase (Invitrogen, Cergy-Pontoise, France). Total PCR products were cloned into the TA vector (Invitrogen), checked for sequence integrity and digested with BamHI/SalI. The plasmid pRRLsin-.PPT.hPGK.GFPpre was digested with BamHI/SalI (New England Biolabs, Beverly, Mass., USA) to remove eGFP. After ligation, the plasmid pRRLsin.PPT.hPGK.HApre, hereafter referred to as LvPGK-HA, was obtained. To produce lentiviral vectors, a total of $4.10^6$ 293T-cells were co-transfected with the transfer vector, the packaging and the envelope plasmids in 10-cm dishes using the calcium phosphate method as described [21a] in DMEM supplemented with serum and antibiotics (Lifetechnologies, Gaithersburg, Md., USA). Lentiviral supernatants were collected at 18, 42 and 66 hrs post co-transfection in serum-free DMEM supplemented with antibiotics and L-glutamine, and concentrated by ultrafiltration using either the Ultrafree-15 or the Centricon Plus-80 filter devices according to the manufacturer instructions (Millipore, Bedford, Mass., USA). Briefly, supernatants were applied to the filter devices and spun at 2000 g for 20 min. at 20° C. Concentrated supernatants were aliquoted and kept at −80° C. until use. Viral stocks of the LvPGK-GFP lentiviral vector were titered on 143B cells as previously described [21a]. Viral stocks of the LvPGK-GFP and LvPGK-HA vectors were also quantified using a gag p24 ELISA (Zeptometrix, Buffalo, N.Y., USA).

Microscopy and images treatment. Whole thymus or liver were excised from injected mice and placed in PBS 1× in a 6-well plate. Pictures of the whole organ were acquired using a DP-11 numeric camera coupled with the CK-40 inverted microscope equipped with a mercury lamp (Olympus France S.A, Rungis, France). Images were processed using Adobe Photoshop (Adobe Systems Inc., San Jose, Calif., USA).

Flow cytometry. Thymi were dilacerated between two frosted slides in 1× PBS supplemented with 3% Fetal Calf Serum (Lifetechnologies). Cell suspensions were numerated and $10^6$ cells were stained with the following monoclonal antibodies (Becton Dickinson Biosciences, le Pont de Claix, France): CD4-APC (allophycocyanin), CD8-CyCr (Cychrome) and either CD3 or pan beta-chain of the TCR-PE (phycoerytrin) or purified anti-clonotypic TCR for the HA peptide SFERFEIFPK presented by MHC class II I-$E^d$ (clone 6.5) ([15a]) followed by biotinylated anti-rat IgG2b and streptavidin-FITC. Data were collected on a FACScalibur (BD Biosciences) and analysed with FlowJo software (TreeStar, Ashland, Oreg., USA).

Abbreviations used are the followings: DN: double negative, DP: double positive, SP: single positive, IT: intra thymic, IV: intra venous, HA: hemaglutinin, MOI: multiplicity of infection, SCID: severe combined immunodeficiencies.

5) References

1a. Hugo, P. Boyd, R: Thymus in *Nature Encyclopedia of Life Sciences*, London: Nature Publishing Group; 2002. [doi: 10.1038/npg.els.0000526]

2a. Klein, L, Kyewski, B: Self-antigen presentation by thymic stromal cells: a subtle division of labor. *Curr Opin Immunol* 2000, 12:179-186.

3a. Naji, A: Induction of tolerance by intrathymic inoculation of alloantigen. *Curr Opin Immunol* 1996, 8:704-709.

4a. Posselt, A M, Barker, C F, Tomaszewski, J E, Markmann, J F, Choti, M A, Naji, A: Induction of donor-specific unresponsiveness by intrathymic islet transplantation. *Science* 1990, 249:1293-1295.

5a. Khoury, S J, Gallon, L, Chen, W, Betres, K, Russell, M E, Hancock, W W, Carpenter, C B, Sayegh, M H, Weiner, H L: Mechanisms of acquired thymic tolerance in experimental autoimmune encephalomyelitis: thymic dendritic-enriched cells induce specific peripheral T cell unresponsiveness in vivo. *J Exp Med* 1995, 182:357-366.

6a. Ilan, Y, Attavar, P, Takahashi, M. Davidson, A, Horwitz, M S, Guida, J, Chowdhury, N R, Chowdhury, J R: Induction of central tolerance by intrathymic inoculation of adenoviral antigens into the host thymus permits long-term gene therapy in Gunn rats. *J Clin Invest* 1996, 98:2640-2647.

7a. DeMatteo, R P, Chu, G, Ahn, M, Chang, E, Barker, C F, Markmann, J F: Long-lasting adenovirus transgene expression in mice through neonatal intrathymic tolerance induction without the use of immunosuppression. *J Virol* 1997, 71:5330-5335.

8a. Rooke, R, Waltzinger, C, Benoist, C, Mathis, D: Targeted complementation of MHC class II deficiency by intrathymic delivery of recombinant adenoviruses. *Immunity* 1997, 7:123-134.

9a. Vigna, E, Naldini, L: Lentiviral vectors: excellent tools for experimental gene transfer and promising candidates for gene therapy. *J Gene Med* 2000, 2:308-316.

10a. Kafri, T, Blomer, U, Peterson, D A, Gage, F H, Verma, I M: Sustained expression of genes delivered directly into liver and muscle by lentiviral vectors. *Nat. Genet.* 1997, 17:314-317.

11a. Esslinger, C, Chapatte, L, Finke, D, Miconnet, I, Guillaume, P, Levy, F, MacDonald, H R: In vivo administration of a lentiviral vaccine targets DCs and induces efficient CD8(+) T cell responses. *J Clin Invest* 2003, 111:1673-1681.

12a. VandenDriessche, T, Thorrez, L, Naldini, L, Follenzi, A, Moons, L, Berneman, Z, Collett, D, Chuah, M K: Lentiviral vectors containing the human immunodeficiency virus type-1 central polypurine tract can efficiently transduce nondividing hepatocytes and antigen-presenting cells in vivo. *Blood* 2002, 100:813-822.

13a. Naldini, L, Blömer, U, Gallay, P, Ory, D, Mulligan, R, Gage, F H, Verma, I M, Trono, D: In vivo gene delivery and stable transduction of nondividing cells by a lentiviral vector. *Science* 1996, 272:263-267.

14a. Pan, D, Gunther, R, Duan, W, Wendell, S. Kaemmerer, W, Kafri, T, Verma, I M, Whitley, C B: Biodistribution and toxicity studies of VSVG-pseudotyped lentiviral vector after intravenous administration in mice with the observation of in vivo transduction of bone marrow. *Mol Ther* 2002, 6:19-29.

15a. Kirberg, J, Baron, A, Jakob, S, Rolink, A, Karjalainen, K, von Boehmer, H: Thymic selection of CD8+ single positive cells with a class II major histocompatibility complex-restricted receptor. *J. Exp. Med.* 1994, 180:25-34.

16a. Trani, J, Moore, D J, Jarrett, B P, Markmann, J W, Lee, M K, Singer, A, Lian, M-M, Tran, B, Caton, A J, Markmann, J F: CD25+ Immunoregulatory CD4 T Cells Mediate Acquired Central Transplantation Tolerance. *J Immunol* 2003, 170:279-286.

17a. Unumatz, D, KewalRamani, V N, Marmon, S, Littman, D R: Cytokine signals are sufficient for HIV-1 infection of resting human T lymphocytes. *J. Exp. Med.* 1999, 189:1735-1746.

18a. Buckley, R H: Molecular Defects in Human Severe Combined Immunodeficiency and Approaches to Immune Reconstitution. *Annu Rev Immunol* 2004, 22:625-655.

19a. Noguchi, M, Yi, H, Rosenblatt, H M, Filipovich, A H, Adelstein, S, Modi, W S, McBride, O W, Leonard, W J: Interleukin-2 receptor gamma chain mutation results in X-linked severe combined immunodeficiency in humans. *Cell* 1993, 73:147-157.

20a. Arpaia, E, Shahar, M, Dadi, H, Cohen, A, Roifman, C: Defective T cell receptor signaling and CD8+ thymic selection in humans lacking ZAP-70 kinase. *Cell* 1994, 76:947-958.

21a. Marodon, G, Mouly, E, Blair, E J, Frisen, C, Lemoine, F M, Klatzmann, D: Specific transgene expression in human and mouse CD4+ cells using lentiviral vectors with regulatory sequences from the CD4 gene. *Blood* 2003, 101:3416-3423.

22a. Bousso, P, Wahn, V, Douagi, I, Horneff, G, Pannetier, C, Le Deist, F, Zepp, F, Niehues, T, Kourilsky, P, Fischer, A, et al: Diversity, functionality, and stability of the T cell repertoire derived in vivo from a single human T cell precursor. *Proc. Natl Acad Sci USA* 2000, 97:274-278.

23a. Follenzi, A, Allies, L E, Bakovic, S, Geuna, M, Naldini, L: Gene transfer by lentiviral vectors is limited by nuclear translocation and rescued by HIV-1 pol sequences. *Nat Genet* 2000, 25:217-222.

6) Figure Legends

FIG. 8—In vivo expression of eGFP after intrathymic injection of the LvPGK-GFP vector. D5: day 5 post-injection localisation of transduced cells around the injection site (arrow) under visible and UV-lights (upper picture). Fibroblast-shaped cells are predominantly transduced (UV-light only) (lower panel). D30: day 30 post-injection expression of eGFP in the thymus (visible+UV-light) (upper panel) and in the liver (UV-light only) (lower panel). CTRL: Thymus (upper panel) and liver (lower panel) pictures from control mice injected IT with PBS examined for background fluorescence under visible and UV-lights. Magnifications are indicated in the lower right corner of each picture.

Figure 9:
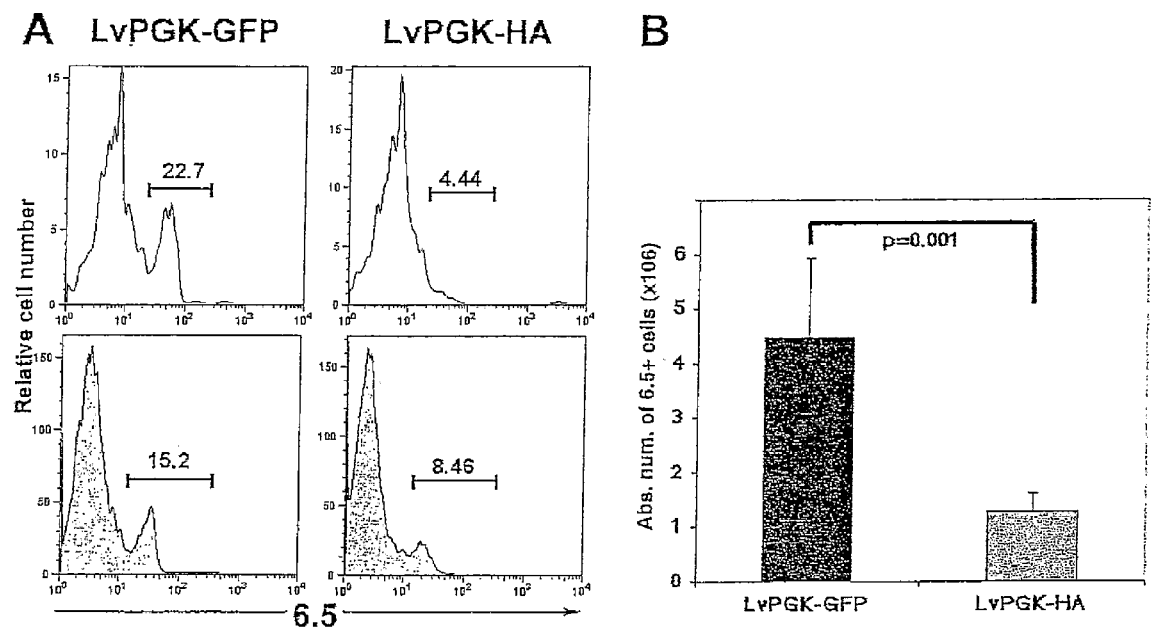
FIG. 9—Negative selection of developing thymocytes (A) TCR transgenic expression within thymic CD8SP (white) and CD4SP cells (grey). (B) Absolute counts of HA-specific thymocytes six days after intra thymic injection of LvPGK-GFP or LvPGK-HA lentiviral vectors.

FIG. 9—Negative selection of developing thymocytes (A) TCR transgenic expression within thymic CD8SP (white) and CD4SP cells (grey) identified by the anti-clonotypic monoclonal antibody 6.5 in SFE-Tg mice six days after IT injection of 40 to 60 ng p24 of the LvPGL-GFP lentiviral vector (n=2) or of 3.5 to 6 ng p24 of the LvPGK-HA vector (n=3). Shown are representative profile of two independent experiments. Numbers indicate the frequency of $6.5^+$ cells (B) Absolute counts of HA-specific thymocytes six days after intra thymic injection of LvPGK-GFP or LvPGK-HA lentiviral vectors. These figures were obtained based on the percentages of total $6.5^+$ thymocytes determined by flow cytometry as shown in (A). Statistical analysis was performed using Student's t-test.

FIG. 10—eGFP expression in developing thymocytes.

Total thymocytes were stained with anti-CD4, anti-CD8 and anti-CD3 monoclonal antibodies. Upper panels: saline-injected control mice (CTRL) and LvPGK-GFP-injected mice at two different time points after injection (D5 and D30) are shown. Lower panels: The profile of CD4/CD8 expression is shown within gated $eGFP^+$ cells.

III) Shifting the Balance of Regulatory Versus Effector T Cell Differentiation by Intrathymic Expression of the Cognate Antigen Abbreviations used hereafter are the followings: HA, hemagglutinin; HEL, hen egg lysozyme; Treg, regulatory T cells; mTEC, medullar thymic epithelial cells; PGK, phospho-glycerate kinase.

1) Abstract

Regulatory/suppressor T cells with various phenotypes and functions co-exist in the immune system. Among them, a unique subset of naturally occurring CD4$^+$CD25$^+$ regulatory T cells is generated in the thymus. Whether or not such regulatory T cells are generated through recognition of self-antigens expressed in the thymus is controversial. To address this question, the inventors analyzed thymic differentiation of T cells specific for the hemagglutinin (HA) protein of Influenza virus in HA-transgenic mice or as the result of intrathymic injection of an HA-expressing lentiviral vector. Strikingly, HA expression in the thymus led to a 10-fold enrichment in the absolute numbers of HA-specific CD4$^+$CD25$^+$ thymocytes, as compared to control mice. Furthermore, it resulted in an enrichment of functional antigen-specific regulatory T cells in the periphery. The results thus indicate that regulatory T cell differentiation is an active process instructed by thymic expression of the cognate antigen. In addition, they show that lentiviral vector mediated antigen expression represents a novel and easy means for in vivo generation of antigen-specific regulatory T cells, for research and therapeutic purposes.

2) Introduction

Several populations of T cells with regulatory/suppressive functions co-exist in the immune system. Among them, regulatory CD4$^+$ T cells expressing the α-chain of the interleukin-2 receptor (CD25) (Treg) have attracted particular interest because they have been shown to prevent, delay or cure a variety of autoimmune diseases in mice (reviewed in (1b)). Furthermore, several autoimmune diseases in humans have been linked to a qualitative and/or quantitative defect of Treg. A representative example is the IPEX syndrome, a fatal disorder caused by a genetic defect in the foxp3 transcription factor that is considered the master gene for Treg differentiation (2b, 3b). Therefore, Treg hold great promises for treating immune disorders in general and autoimmune diseases in particular.

The generation of Treg in the thymus starts during the fetal period in humans (4b) and the perinatal period in mice (5b). The regulatory function of Treg is acquired during thymic selection, as shown by the ability of isolated CD4$^+$CD25$^+$ thymocytes to suppress lymphocyte proliferation (6b). The inventors previously suggested that recognition of the cognate antigen in the thymus leads to the emergence of CD4$^+$CD25$^+$ T cells (7b). More recently, it has been shown that HA expression in the thymus led to increased frequency and/or number of HA-specific Treg in T cell receptor (TCR) transgenic mice (8b-11b). Similar observations have also been reported in ovalbumin-(12b-14b) and glucose-6-phosphate-isomerase specific TCR transgenic mice (15b). However, in TCR transgenic mice specific for the moth cytochrome c or the hen egg lysozyme (HEL) antigens, the numbers of specific Treg did not increase upon expression of the cognate antigen in the thymus despite an augmentation in their frequencies, suggesting a better survival of Treg during negative selection (16b, 17b). Therefore, the impact of thymic cognate antigen expression on Treg selection remains controversial.

To re-assess thymic Treg cell selection, the inventors used transgenic mice expressing the hemagglutinin (HA) protein of Influenza virus under control of the insulin promoter (Ins-HA) (18b), mimicking the physiological expression of insulin in the thymus by medullar thymic epithelial cells (mTEC) (19b). The inventors studied the impact of HA expression in the thymus on Treg selection by crossing these mice with TCR transgenic mice specific for the HA$_{111-119}$ peptide presented by MHC class II I-E$^d$ molecules (TCR-HA) (20b). In these mice, HA-specific T cells can be identified with the 6.5 anti-clonotypic mAb. In TCR-HAxIns-HA transgenic mice, the transgenic TCR-beta chain frequently pair with endogenous TCR-alpha chains such that HA-specific TCR-αβ chain expression is limited to only 10-20% of the CD4$^+$ T cells (21b). This is in sharp contrast with other models in which the TCR transgenic T cells can be represented at frequencies over 90%. The inventors also expressed HA in TCR-HA transgenic mice using intrathymic injection of a HA-encoding lentiviral vector (see above). These results show that the cognate antigen can instruct Treg differentiation.

3) Results and Discussion

As previously reported, 20 to 30% of TCR-HAxIns-HA double-transgenic mice developed diabetes by five weeks of age, while the others acquired lymphocyte infiltrates of the pancreatic β-islets (21b). To understand why these mice failed to develop complete immune tolerance to HA, the inventors first investigated thymic differentiation of the HA-specific T cells in non-diabetic TCR-HAxIns-HA mice. Compared to age-matched TCR-HA mice, mean numbers of HA-specific 6.5$^+$ thymocytes were unchanged, or decreased by less than two-fold, at 6 or 14 weeks of age, respectively (FIG. 11A). The deletion of HA-specific thymocytes in TCR-HAxIns-HA mice is therefore much less pronounced than that observed in similar models of transgenic mice expressing the cognate antigen under various tissue-specific promoters, such as insulin-promoter driven ovalbumin expression in DO11-10 TCR transgenic mice (11b, 13b). The persistence of HA-specific thymocytes in mice with partial but significant control of diabetes, led us to investigate the development of Treg in this setting. The inventors thus analyzed the differentiation of CD25$^+$ and CD25$^-$ 6.5$^+$ thymocytes during their transition from immature double positive (CD4$^+$CD8$^+$, DP) to mature CD4$^+$CD8$^-$ (CD4SP) T cells, through the CD4$^+$CD8$^{lo}$ (CD4$^{int}$) stage (FIG. 11B). As compared to TCR-HA transgenic mice, the frequencies of 6.5$^+$ cells in the CD25$^-$ subset were decreased at both CD4SP and CD4$^{int}$ stages in TCR-HAxIns-HA mice (FIG. 11D). In sharp contrast, the frequencies of 6.5$^+$ cells within CD25$^+$ thymocytes were amplified 3-, 4- and almost 10-fold in DP, CD4$^{int}$ and CD4SP subsets of TCR-HAxIns-HA mice, respectively (FIGS. 11C and 11D). The amplified frequencies translated into augmented cell numbers (FIG. 12). Compared to TCR-HA mice, the augmentation of 6.5$^+$CD25$^+$ cell numbers was already detected in the DP subset of TCR-HAxIns-HA mice, and was 10-fold in both CD4$^{int}$ and CD4SP thymocytes. Importantly, such an augmentation was not detected for 6.5$^-$CD25$^+$ T cells, indicating that it was indeed HA-driven (FIG. 12). Others and the inventors have shown that the majority of CD4SP CD25$^+$ thymocytes express foxp3 mRNA and have suppressive activities similar to peripheral Treg (4b, 8b, 16b). In the TCR-HAxIns-HA mice, CD4$^+$CD25$^+$ thymocytes also expressed foxp3 mRNA (FIG. 14). Thus, these results indicate that expression of HA in the thymus led to generation of increased numbers of HA-specific Treg.

The inventors reported above that thymic stromal cells could be efficiently transduced following intrathymic injection of lentiviral vectors. Thus, to further address the role of thymic cognate antigen expression on Treg differentiation, the inventors injected a HA-encoding lentiviral vector (FIG. 13A) in the thymus of TCR-HA mice. This resulted in deletion of 6.5$^+$CD25$^-$ thymocytes, which could be detected one week but not one or two months post injection (Table 2). In contrast, frequencies of HA-specific cells within CD25$^+$ CD4SP thymocytes were amplified 2- to 10-fold at one week and also at one to two months post-injection (Table 2). The amplified frequencies of 6.5$^+$CD25$^+$ cells in the CD4SP subset translated into a 10-fold increase in their numbers (FIG.

13B). Of note, the number of HA-specific CD4$^+$CD25$^+$ T cells in mice which had received the HA-expressing vector reached the absolute number of total CD4$^+$CD25$^+$ T cells in untreated mice (FIG. 13B), indicating that the cognate antigen had a major effect on the positive selection of CD4$^+$CD25$^+$ cells. There was a moderate but significant increase in the mean number of 6.5$^-$CD25$^+$ cells in HA-expressing vector treated mice (FIG. 12B). Collectively, these results show that intrathymic expression of the cognate antigen led to the augmentation in frequencies and numbers of HA-specific Treg in mice that had never previously been exposed to the antigen.

The thymic cells mediating this effect remain to be characterized. The inventors obtained a similar positive selection of HA specific Treg after transplantation of bone marrow from TCR-HA transgenic mice into irradiated TCR-HA transgenic mice injected with HA-expressing vector, indicating that these cells are radio-resistant. Since thymic cortical epithelial cells are thought to be responsible for Treg differentiation in the thymus (23b), the inventors speculate that they also contribute to Treg generation upon lentiviral vector mediated antigen expression.

The frequency of 6.5$^+$CD25$^+$ was also increased in lymph nodes of mice injected with the HA-expressing vector, as compared to control mice injected with an eGFP-expressing vector (Table 2). Because CD25$^+$ cells only represent 5-6% of total CD4$^+$ cells, the augmentation in 6.5$^+$CD25$^+$ frequencies could have resulted from the conversion of 6.5$^+$CD25$^-$ cells into activated CD25$^+$ cells. Since viral vectors can leak after intrathymic injection, this conversion could have occurred upon recognition of HA-expressing cells in the periphery. The inventors thus analyzed the suppressive activity of purified CD4$^+$CD25$^+$ cells from lentivirus vector treated mice by their ability to prevent or delay diabetes in Ins-HA transgenic mice (FIG. 13C). To induce diabetes, the inventors injected sub-lethally irradiated Ins-HA transgenic mice with CD4$^+$CD25$^-$ T cells from TCR-HA mice and then immunized the mice with HA-pulsed dendritic cells. The inventors found that peripheral CD4$^+$CD25$^+$ cells from mice that had been injected with the HA-expressing vector had a remarkably increased capacity to prevent diabetes, as compared to CD4$^+$CD25$^+$ cells from control mice (FIG. 13C). Collectively, these results indicate that intrathymic injection of a HA-encoding lentiviral vector in HA-specific TCR transgenic mice results in an enrichment of HA-specific Treg in the thymus and in the periphery.

Whether the increased frequency of Treg upon thymic expression of the cognate antigen corresponds to an increased resistance of Treg to negative selection or a true positive selection remains controversial. When antigens are expressed under control of the insulin promoter, thus presumably in mTEC, increased absolute numbers of antigen-specific Treg have been observed with HA (this report) and OVA (14b), while not with HEL (17b). The increased frequency of antigen-specific CD4$^+$CD25$^+$ in this latter case was interpreted as evidence for better resistance of Treg to negative selection. However, negative selection in the presence of the cognate antigen is much more pronounced in the HEL model (a 40-fold vs. a 2-fold reduction of HEL-specific and HA-specific thymocytes, respectively) and may mask the positive selection effect. Indeed, Treg are also susceptible to negative selection when confronted with high levels of the cognate antigen (16b, 23b). The inventors suggest that mTEC may actually mediate both negative selection of auto-reactive T cells (24b) and Treg commitment, depending on the avidity of the mTEC and developing thymocytes interaction. Since the inventors observed that the enrichment of HA-specific Treg upon thymic HA expression begins at the DP stage, this may reflect an early commitment of immature thymocytes to the Treg lineage. Altogether, these results support that the signal delivered by TCR recognition of a self-peptide-MHC class II molecule complex instructs uncommitted precursors to differentiate into the Treg lineage.

While conversion of naive CD25$^-$ cells into foxp3-expressing CD25$^+$ regulatory T cells in the periphery is possible upon continuous antigenic stimulation (25b) or homeostatic proliferation in the absence of a thymus (26b), it is not yet clear whether or not these peripherally-induced Treg will be as efficient as natural Treg in a therapeutic setting. As far as autoimmunity is concerned, it is increasingly recognized that antigen-specific Treg are very efficient to prevent or delay the deleterious effects of autoimmune responses. In vitro expansion of antigen-specific Treg has previously been shown to represent an effective means to obtain large numbers of functional Treg able to prevent and/or to cure diabetes in NOD (27b, 28b) or in Ins-HA mice. The results show that a simple intervention in the thymus is sufficient to shift the balance of T cell differentiation towards increased Treg generation and thus opens new perspectives for therapeutic intervention.

4) Materials and Methods

Mice. Six- to fourteen-week-old heterozygous transgenic mice for the hemagglutinin antigen (HA) and the insulin promoter (Ins-HA) (18b) or homozygous for a TCR specific for the HA 111-119 epitope (SFERFEIFPK) presented by I-E$^d$ molecules (20b) were backcrossed on a Balb/c background for more than ten generations and were bred in specific pathogen-free conditions according to the European Union guidelines.

Intrathymic injections. Mice were anesthetized with 30 mg/kg of Ketamine (Imalgene, Merial) and 24 mg/kg of Xylazine (Rompun, Bayer). The surgical procedure is described above. Briefly, the thymus was made visible after opening the thoracic cage and 10 to 20 µl of lentiviral stock was injected using a 300-µl syringe (Terumo).

Lentiviral vectors. Construction of the LvPGK-HA vector has been described in detail above and derives from the LvPGK-GFP vector (29b). Briefly, lentiviral vector stocks were produced by calcium phosphate transfection of three plasmids encoding the eGFP- or HA-expressing vectors, the Vesicular Stomatitis Virus envelope and the packaging proteins in 293T cells as described (30b). Supernatants were concentrated by ultrafiltration using Centricon-plus columns (Amicon) and viral titers were measured at different dilutions in 143B cell line for the eGFP-expressing vector and with a p24 ELISA (Zeptometrix, Buffalo, N.Y.) for both vectors. Only viral stocks with titers above 10$^7$ infectious particles per ml (>100 ng/ml of p24) were used for intrathymic injections.

Flow cytometry analysis. Cells from teased organs were labelled in PBS containing 3% fetal calf serum at room temperature for 15 to 30 min. in the dark under continuous agitation. The following monoclonal antibodies were used for phenotypic analysis: allophycocyanin-labelled anti-CD4 (RM4-5), fluorescein isothiocyanate-conjugated anti-CD8 (clone 53.6.7), phycoerytrin-labeled anti-CD25 (all from Pharmingen, San Diego, Calif.). Labelling with the anti-clonotypic mAb (clone 6.5) specific to TCR-HA was revealed by a biotin anti-rat IgG2b Ab and streptavidin-CyChrome (Pharmingen) or directly with a goat-anti-rat IgG labeled with PE (Caltag Laboratories, Burlingame, Calif.). Isotype-irrelevant mAbs (Pharmingen) were used as controls. At least 30,000 events were collected on a FACScalibur (Becton Dickinson, San Jose, Calif.). Data were analyzed using the FlowJo software (TreeStar Inc., Arshland, Oreg.)

Cell purification. After mechanical dissociation, cells from spleen and peripheral LN were sequentially incubated with saturating amounts of biotin-labeled anti-CD25 mAb (7D4, Pharmingen) and streptavidin microbeads (Miltenyi Biotec, Bergish Gladbach, Germany) for 30 min. on ice, followed by two rounds of LS columns for magnetic cell separation (Miltenyi Biotec), according to the manufacturer instructions. All steps were performed in PBS with 3% fetal calf serum. The purity of sorted CD4$^+$CD25$^+$ cells was 75-85%. For dendritic cell purification, spleens from Balb/c mice were digested with liberase (1.67 Wünsh U/ml, Boehringer Mannheim) and Dnase (0.1 mg/ml, Boerhinger Mannheim) diluted in LPS-low RPMI (InVitrogen, Cergy Pontoise, France) in a 37° C., 5% CO2 incubator for 30 min. to one hour. Dissociated splenocytes were filtered and washed in LPS-free 1× PBS (InVitrogen). Cells were incubated with anti-CD11c microbeads (Miltenyi Biotec) for 30 min. on ice, followed by magnetic separation using LS columns (Miltenyi Biotec). The purity of CD11c$^+$ cells was of 95%.

Diabetes induction and monitoring. $7.5.10^6$ CD25$^-$ cells from spleen and LN of TCR-HA transgenic mice were injected intravenously, with or without $5.10^5$ purified CD4$^+$CD25$^+$ cells, into 3-Gy irradiated Ins-HA transgenic mice. Then, mice were immunized by intravenous injection of splenic DC, matured after overnight culture, and pulsed with the HA$_{111-119}$ peptide. Blood glucose levels were monitored every other day using a glucometer (LifeScan Inc.). Mice were considered diabetic if two consecutive readings were above 250 mg/dl.

Statistical analysis. Two-tailed unpaired t-test with 95% confidence intervals were performed using GraphPad Prism version 4.0 for Macintosh (GraphPad Software, San Diego, Calif.). Mean values were considered statistically different if the p value was inferior to 0.05.

Online supplemental material. CD4SP thymocytes from a 14 week-old TCR-HAxIns-HA mouse were sorted as CD25$^+$ or CD25$^-$ fraction on a FACsort (Becton Dickinson) after three-color staining with CD4-PE-Cyanin5, CD8-FITC and CD25-PE (Pharmingen). Total mRNA was extracted from $5.10^4$ CD25$^+$ and $10^6$ CD25$^-$ cells using RNAble (Eurobio, France) and reverse-transcribed to cDNA using Murine Moloney leukemia Virus Reverse Transcriptase (InVitrogen) according to the manufacturer instructions. The cyclophylin cDNA was amplified from diluted CD25$^-$ sample to obtain a band of similar intensity than in the CD25$^+$ fraction. Then, foxp3 and cyclophylin cDNAs were amplified in the same PCR reaction. After agarose gel migration, the intensity of the bands were measured using the public domain NIH Image program (developed at the U.S. National Institutes of Health and available on the Internet).

5) References

1b. Sakaguchi, S. 2004. Naturally Arising CD4+ Regulatory T Cells for Immunologic Self-Tolerance and Negative Control of Immune Responses. *Annual Review of Immunology* 22:531-562.

2b. Bennett, C. L., J. Christie, F. Ramsdell, M. E. Brunkow, P. J. Ferguson, L. Whitesell, T. E. Kelly, F. T. Saulsbury, P. F. Chance, and H. D. Ochs. 2001. The immune dysregulation, polyendocrinopathy, enteropathy, X-linked syndrome (IPEX) is caused by mutations of FOXP3. *Nat Genet* 27:20-21.

3b. Hori, S., T. Nomura, and S. Sakaguchi, 2003. Control of regulatory T cell development by the transcription factor Foxp3. *Science* 299:1057-1061.

4b. Darrasse-Jèze, G., G. Marodon, M. Catala, B. Salomon, and D. Klatzmann. 2004. Ontogeny of CD4+CD25+ regulatory/suppressor T cells in the human fetus. *Blood* In press.

5b. Asano, M., M. Toda, N. Sakaguchi, and S. Sakaguchi. 1996. Autoimmune disease as a consequence of developmental abnormality of a T cell subpopulation. *J Exp Med* 184:387-396.

6b. Itoh, M., T. Takahashi, N. Sakaguchi, Y. Kuniyasu, J. Shimizu, F. Otsuka, and S. Sakaguchi. 1999. Thymus and autoimmunity: production of CD25+CD4+ naturally anergic and suppressive T cells as a key function of the thymus in maintaining immunologic self-tolerance. *J Immunol* 162:5317-5326.

7b. Marodon, G., and B. Rocha. 1994. Activation and "deletion" of self-reactive mature and immature T cells during ontoeny of Mls-1a mice: implications for neonatal tolerance induction. *Int. Immunol.* 6:1899-1904.

8b. Jordan, M. S., A. Boesteanu, A. J. Reed, A. L. Petrone, A. E. Holenbeck, M. A. Lerman, A. Naji, and A. J. Caton. 2001. Thymic selection of CD4+CD25+ regulatory T cells induced by an agonist self-peptide. *Nat Immunol* 2:301-306.

9b. Apostolou, I., A. Sarukhan, L. Klein, and H. von Boehmer. 2002. Origin of regulatory T cells with known specificity for antigen. *Nat Immunol* 3:756-763.

10b. Klein, L., K. Khazaie, and H. von Boehmer. 2003. In vivo dynamics of antigen-specific regulatory T cells not predicted from behavior in vitro. *PNAS* 100:8886-8891.

11b. Lerman, M. A., J. Larkin, III, C. Cozzo, M. S. Jordan, and A. J. Caton. 2004. CD4+CD25+ Regulatory T Cell Repertoire Formation in Response to Varying Expression of a neo-Self-Antigen. *J. Immunol.* 173:236-244.

12b. Kawahata, K., Y. Misaki, M. Yamauchi, S. Tsunekawa, K. Setoguchi, J. Miyazaki, and K. Yamamoto. 2002. Generation of CD4(+)CD25(+) regulatory T cells from autoreactive T cells simultaneously with their negative selection in the thymus and from nonautoreactive T cells by endogenous TCR expression. *J. Immunol* 168:4399-4405.

13b. Walker, L. S. K., A. Chodos, M. Eggena, H. Dooms, and A. K. Abbas. 2003. Antigen-dependent Proliferation of CD4+CD25+ Regulatory T Cells In Vivo. *J. Exp. Med.* 198:249-258.

14b. Lohr, J., B. Knoechel, E. C. Kahn, and A. K. Abbas. 2004. Role of B7 in T Cell Tolerance. *J. Immunol.* 173:5028-5035.

15b. Shih, F. F., Mandik-Nayak, B. T. Wipke, and P. M. Allen. 2004. Massive Thymic Deletion Results in Systemic Autoimmunity through Elimination of CD4+CD25+ T Regulatory Cells. *J. Exp. Med.* 199:323-335.

16b. van Santen, H.-M., C. Benoist, and D. Mathis. 2004. Number of T Reg Cells That Differentiate Does Not Increase upon Encounter of Agonist Ligand on Thymic Epithelial Cells. *J. Exp. Med.* 200:1221-1230.

17b. Liston, A., D. H. D. Gray, S. Lesage, A. L. Fletcher, J. Wilson, K. E. Webster, H. S. Scott, R. L. Boyd, L. Peltonen, and C. C. Goodnow. 2004. Gene Dosage-limiting Role of Aire in Thymic Expression, Clonal Deletion, and Organ-specific Autoimmunity. *J. Exp. Med.* 200:1015-1026.

18b. Lo, D., J. Freedman, S. Hesse, R. D. Palmiter, R. L. Brinster, and L. A. Sherman. 1992. Peripheral tolerance to an islet cell-specific hemagglutinin transgene affects both CD4+ and CD8+ T cells. *Eur J Immunol* 22:1013-1022.

19b. Derbinski, J., A. Schulte, B. Kyewski, and L. Klein. 2001. Promiscuous gene expression in medullary thymic epithelial cells mirrors the peripheral self. *Nat Immunol* 2:1032-1039.

20b. Kirberg, J., A. Baron, S. Jakob, A. Rolink, K. Karjalainen, and H. von Boehmer. 1994. Thymic selection of CD8+ single positive cells with a class II major histocompatibility complex-restricted receptor. *J. Exp. Med.* 180:25-34.

21b. Sarukhan, A., A. Lanoue, A. Franzke, N. Brousse, J. Buer, and H. von Boehmer. 1998. Changes in function of antigen-specific lymphocytes correlating with progression towards diabetes in a transgenic model. *Embo J* 17:71-80.

23b. Bensinger, S. J., A. Bandeira, M. S. Jordan, A. J. Caton, and T. M. Laufer. 2001. Major Histocompatibility Complex Class II-positive Cortical Epithelium Mediates the Selection of CD4+25+ Immunoregulatory T Cells. *J. Exp. Med.* 194:427-438.

24b. Klein, L., T. Klein, U. Ruther, and B. Kyewski. 1998. CD4 T cell tolerance to human C-reactive protein, an inducible serum protein, is mediated by medullary thymic epithelium. *J Exp Med* 188:5-16.

25b. Apostolou, I., and H. von Boehmer. 2004. In Vivo Instruction of Suppressor Commitment in Naive T Cells. *J. Exp. Med.* 199:1401-1408.

26b. Liang, S., P. Alard, Y. Zhao, S. Parnell, S. L. Clark, and M. M. Kosiewicz. 2005. Conversion of CD4+CD25− cells into CD4+CD25+ regulatory T cells in vivo requires B7 costimulation, but not the thymus. *J. Exp. Med.* 201:127-137.

27b. Tang, Q., K. J. Henriksen, M. Bi, E. B. Finger, G. Szot, J. Ye, E. L. Masteller, H. McDevitt, M. Bonyhadi, and J. A. Bluestone. 2004. In Vitro-expanded Antigen-specific Regulatory T Cells Suppress Autoimmune Diabetes. *J. Exp. Med.* 199:1455-1465.

28b. Tarbell, K. V., S. Yamazaki, K. Olson, P. Toy, and. R. M. Steinman. 2004. CD25+ CD4+ T Cells, Expanded with Dendritic Cells Presenting a Single Autoantigenic Peptide, Suppress Autoimmune Diabetes. *J. Exp. Med.* 199:1467-1477.

29b. Follenzi, A., L. E. Allies, S. Bakovic, M. Geuna, and L. Naldini. 2000. Gene transfer by lentiviral vectors is limited by nuclear translocation and rescued by HIV-1 pol sequences. *Nat Genes* 25:217-222.

30b. Marodon, G., E. Mouly, E. J. Blair, C. Frisen, F. M. Lemoine, and D. Klatzmann. 2003. Specific transgene expression in human and mouse CD4+ cells using lentiviral vectors with regulatory sequences from the CD4 gene. *Blood* 101:3416-3423.

6) Figure Legends

FIG. 11. HA-specific thymocyte differentiation in TCR-HA and TCR-HAxIns-HA transgenic mice. (A) Absolute numbers of HA-specific ($6.5^+$) cells in the thymus of fourteen-week-old TCR-HA (v) and TCR-HAxIns-HA (τ) transgenic mice. Each dot represents a single mouse. The two mean values are statistically different (p<0.05) (B) Gating of thymocyte subsets based on CD4 and CD8 expression in TCR-HA transgenic mice. Indicated are the frequencies of the respective population in percentages of total thymocytes. (C) Overlaid expression of the transgenic TCR ($6.5^+$) in $CD25^+$ cells of the indicated phenotypes in the thymus of TCR-HA (gray lines) and TCR-HAxIns-HA (solid lines) transgenic mice. (D) Frequencies (percentages±SD) of $6.5^+$ cells in $CD25^+$ and $CD25^-$ cells within subsets defined in 1B (DP=$CD4^+CD8^+$; $CD4^{int}$=$CD4^+CD8^{lo}$; CD4SP=$CD4^+CD8^-$ cells).

FIG. 12. Absolute numbers of $CD25^+$ cells in thymocyte subsets of TCR-HA and TCR-HAxIns-HA transgenic mice. Absolute numbers of cells were calculated by multiplying the total viable cell count, as determined by trypan blue exclusion, with the frequencies of cells in each successive population of interest. Each dot represents a single mouse. Upper panels: absolute numbers of $6.5^+CD25^+$ cells in TCR-HA (λ) and TCR-HAxIns-HA (σ) transgenic mice for the indicated subset. For the absolute numbers of $6.5^+CD25^+$ in the DP subset, the mean values were statistically different (p<0.01). The p values were all below 0.002 for the other subsets. Lower panels: absolute numbers of $6.5^-CD25^+$ cells in TCR-HA (μ) and TCR-HAxIns-HA (Δ) transgenic mice for the indicated subset. None of the mean values were statistically different in the three subsets analyzed.

FIG. 13. De novo generation of regulatory T cells upon intrathymic injection of HA-encoding lentiviral vector in TCR-HA transgenic mice. (A) Schematic representation of the HA-encoding lentiviral vector. RSV-U3: U3 promoter/enhancer of the Rous Sarcoma Virus; SD: splice donor; SA: splice acceptor; psi: packaging signal sequence; ga-RRE: truncated gag gene with the rev responsive element; cppT: central polypurine tract; PGK: phospho-glycerate kinase promoter; WPRE: woodchuck hepatitis virus regulatory element; LTR-SIN: self-inactivating long terminal repeat (B) Absolute numbers of $6.5^+CD25^+$ (closed symbols) and $6.5^-CD25^+$ (open symbols) CD4SP thymocytes in TCR-HA transgenic mice injected with GFP-expressing (TCR-HA) or HA-encoding lentiviral vectors (TCR-HA LvHA) (C) Percentages of diabetic Ins-HA mice upon co-transfer of purified $CD25^+$ peripheral T cells from TCR-HA transgenic mice injected in the thymus with GFP-expressing (solid line) or HA-expressing (dashed line) lentiviral vectors 10-days earlier. 100% of the mice became diabetic at day 10-11 without co-transfer of $CD4^+CD25^+$ cells (unpublished results). Data are the pooled results from six mice per group treated in two separate experiments.

FIG. 14. Semi-quantitative assessment of foxp3 mRNA in sorted $CD4^+CD25^+$ and $CD4^+CD25^-$ thymocyte from a TCR-HaxIns-HA mouse. (A) Purity of sorted $CD4^+CD25^+$ (upper panel) and $CD4^+CD25^-$ thymocyte (lower panel) after cell sorting. (B) Optical densities of the PCR bands were measured using the Image software (NIH) in the indicated thymocyte subset. Ratio of housekeeping cyclophylin mRNA over foxp3 mRNA in these arbitary units is represented.

TABLE 2

Frequencies of HA-specific CD4SP T cells from thymus and lymph nodes in TCR-HA transgenic mice injected with lentiviral vectors in the thyms.

| | THYMUS | | LYMPH NODES | |
|---|---|---|---|---|
| | $CD25^+$ | $CD25^-$ | $CD25^+$ | $CD25^-$ |
| TCR-HA LvGFP (n = 9) | 6.5 ± 2.2 | 30.7 ± 3.9 | 9.1 ± 2.5 | 14.3 ± 2.7 |
| TCR-HA LvHA (n = 3) Short term effect | 31.9 ± 6.0 | 11.0 ± 3.0 | ND | ND |
| TCR-HA+LvHA (n = 5) Long term effect | 34.7 ± 16.0 | 27.0 ± 3.9 | 15.1 ± 2.5 | 12.2 ± 2.5 |

Shown are the frequencies (percentages)±S.D of $6.5^+$ cells in $CD25^+$ and $CD25^-$ cells within CD4SP T cells in thymus and lymph nodes of TCR transgenic mice injected with eGFP-(TCR-HA LvGFP) or HA-expressing lentiviral vector (TCR-HA LvHA). Seven to ten-weeks-old mice were injected in the thymus with 15 to 25 ng of lentiviral vectors and sacrified either one week (short term effect) or one to two months (long term effect) after injection for flow cytometry analysis. Only TCR-HA LvHA mice with a minimum of a two-fold increase in the frequency of $6.5^+CD25^+$ in CD4SP cells in the thymus were included in the analysis (8 out of 10 injected). ND; not done.

The invention claimed is:

1. A method for treating genetic immunodeficiencies or acquired immunodeficiencies, comprising:

administering lentiviral vectors by in situ thymic injection to an individual having a genetic immunodeficiency or an acquired immunodeficiency, wherein the lentiviral vectors comprise a predetermined recombinant nucleotide sequence selected from the group consisting of: ADA coding sequence, IL2RG coding sequence, ZAP-70 coding sequence, Rag ½ coding sequence, Jak3 coding sequence, IL7RA coding sequence, CD3 delta sequence and CD3 epsilon sequence; and permitting said lentiviral vectors to stably integrate into a genome of thymic stromal cells, intrathymic lymphocytes or lymphocytes precursors and express the predetermined recombinant nucleotide sequence.

2. The method according to claim 1, wherein the lentiviral vectors correspond to sequences derived from human immunodeficiency virus type-1.

3. The method according to claim 1, said predetermined recombinant nucleotide sequence being under control of elements directing its expression in eukaryotic cells.

4. The method according to claim 1, comprising transforming at least one of the intrathymic lymphocytes or lymphocytes precursors in the patient.

5. The method according to claim 4, wherein the genetic immunodeficiencies are selected from the group of severe combined immunodeficiencies consisting of: ADA-deficiency, X-SCID, ZAP-70 deficiency, Rag ½ deficiency, Jak3 deficiency, IL7RA deficiency and CD3 deficiencies.

6. The method according to claim 4, wherein the lentiviral vectors are T-cell specific lentiviral vectors capable of expressing a therapeutic transgene specifically in T lymphocytes.

7. The method according to claim 1, wherein the lentiviral vectors are administered in a composition suitable for an intrathymic administration by injection, and a dosage of said lentiviral vectors is between $10^5$ and $10^{11}$ infectious particles per milliliter.

* * * * *

UNITED STATES PATENT AND TRADEMARK OFFICE
CERTIFICATE OF CORRECTION

PATENT NO.        : 8,394,777 B2
APPLICATION NO.   : 11/597892
DATED             : March 12, 2013
INVENTOR(S)       : Sitbon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1287 days.

Signed and Sealed this
First Day of September, 2015

Michelle K. Lee
*Director of the United States Patent and Trademark Office*